United States Patent
Mishra et al.

(10) Patent No.: US 9,570,688 B2
(45) Date of Patent: Feb. 14, 2017

(54) SEMICONDUCTOR MATERIALS PREPARED FROM BRIDGED BITHIAZOLE COPOLYMERS

(71) Applicants: BASF SE, Ludwigshafen (DE); POLYERA CORPORATION, Princeton, NJ (US)

(72) Inventors: Ashok Kumar Mishra, Singapore (SG); Subramanian Vaidyanathan, Basel (CH); Hiroyoshi Noguchi, Singapore (SG); Florian Doetz, Singapore (SG); Bo Zhu, Shanghai (CN); Johan Sebastian Basuki, Sydney (AU)

(73) Assignees: BASF SE, Ludwigshafen (DE); Polyera Corporation, Princeton, NJ (US)

( * ) Notice: Subject to any disclaimer, the term of this patent is extended or adjusted under 35 U.S.C. 154(b) by 0 days.

(21) Appl. No.: 14/620,755

(22) Filed: Feb. 12, 2015

(65) Prior Publication Data
US 2015/0162546 A1    Jun. 11, 2015

Related U.S. Application Data

(62) Division of application No. 13/810,819, filed as application No. PCT/EP2011/063109 on Jul. 29, 2011, now abandoned.
(Continued)

(30) Foreign Application Priority Data

Aug. 5, 2010   (EP) ..................... 10172083

(51) Int. Cl.
C08G 75/00   (2006.01)
H01L 51/00   (2006.01)
(Continued)

(52) U.S. Cl.
CPC ......... *H01L 51/0071* (2013.01); *C07D 495/04* (2013.01); *C07D 513/04* (2013.01);
(Continued)

(58) Field of Classification Search
CPC ............ H01L 51/0036; H01L 51/0043; H01L 51/0558; C08G 61/126; Y02E 10/549
(Continued)

(56) References Cited

U.S. PATENT DOCUMENTS 4,522,745 A    6/1985  Kurkov
2008/0121281 A1    5/2008  Gaudiana et al.
(Continued)

FOREIGN PATENT DOCUMENTS

EP    2 085 401    8/2009
GB    2 130 595    6/1984
(Continued)

OTHER PUBLICATIONS
Al-Hashimi et al. Org. Lett., vol. 12, No. 23, 2010.*
(Continued)

*Primary Examiner* — Shane Fang
(74) *Attorney, Agent, or Firm* — Oblon, McClelland, Maier & Neustadt, L.L.P.

(57) ABSTRACT

The present invention provides semiconducting compounds, oligomers and polymers of formula

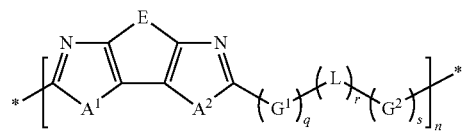

(1)

wherein
$A^1$ and $A^2$ can be the same or different and are S or Se,
E is selected from the group consisting of
(Continued)

Bottom gate bottom contact (BGBC) architecture.

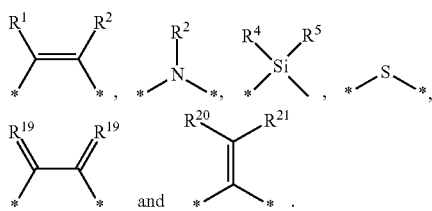

The compounds, oligomers and polymers of formula of formula (1) are suitable for use in electronic devices such as organic field effect transistors.

21 Claims, 1 Drawing Sheet

Related U.S. Application Data

(60) Provisional application No. 61/370,857, filed on Aug. 5, 2010.

(51) Int. Cl.
| | |
|---|---|
| C07D 495/04 | (2006.01) |
| C07D 513/04 | (2006.01) |
| C07D 513/14 | (2006.01) |
| C08G 61/12 | (2006.01) |
| H01L 51/05 | (2006.01) |

(52) U.S. Cl.
CPC ......... *C07D 513/14* (2013.01); *C08G 61/123* (2013.01); *C08G 61/124* (2013.01); *C08G 61/126* (2013.01); *H01L 51/0036* (2013.01); *H01L 51/0068* (2013.01); *H01L 51/0074* (2013.01); *C08G 2261/124* (2013.01); *C08G 2261/226* (2013.01); *C08G 2261/228* (2013.01); *C08G 2261/3223* (2013.01); *C08G 2261/3243* (2013.01); *C08G 2261/3246* (2013.01); *C08G 2261/3327* (2013.01); *C08G 2261/344* (2013.01); *C08G 2261/364* (2013.01); *C08G 2261/414* (2013.01); *C08G 2261/596* (2013.01); *C08G 2261/92* (2013.01); *H01L 51/0508* (2013.01); *H01L 51/0545* (2013.01)

(58) Field of Classification Search
USPC ..... 257/40, E51.005, E51.024; 528/360, 367
See application file for complete search history.

(56) References Cited

U.S. PATENT DOCUMENTS

| | | |
|---|---|---|
| 2009/0230386 A1 | 9/2009 | Yamamoto et al. |
| 2010/0301314 A1* | 12/2010 | Aso ...................... C07D 277/60 257/40 |
| 2011/0006287 A1 | 1/2011 | You et al. |
| 2011/0290324 A1 | 12/2011 | Gaudiana et al. |
| 2012/0217482 A1* | 8/2012 | Mishra ................. C08G 61/126 257/40 |

FOREIGN PATENT DOCUMENTS

| | | |
|---|---|---|
| JP | 59 15256 | 1/1984 |
| SU | 503197 A1 | 2/1976 |
| WO | 83 02368 | 7/1983 |
| WO | 2009 069687 | 6/2009 |

OTHER PUBLICATIONS

International Search Report Issued Aug. 8, 2012 in PCT/EP11/63109 Filed Jul. 29, 2011.
Avramenko et al., CA 85:151837, 1976.
Grandolini et al., CA 69:19099, 1968.

* cited by examiner

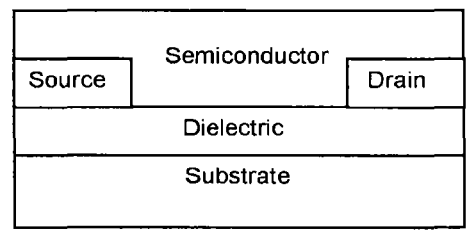
Figure 1: Bottom gate bottom contact (BGBC) architecture.

SEMICONDUCTOR MATERIALS PREPARED FROM BRIDGED BITHIAZOLE COPOLYMERS

This application is a divisional application of U.S. Ser. No. 13/810,819 filed on Jan. 17, 2013 which is a 371 application of PCT/EP2011/063109 filed on Jul. 29, 2011, which claims benefit of 61/670,857 filed on Aug. 5, 2010.

Organic semiconducting materials can be used in electronic devices such as organic photovoltaic (OPV) cells, organic field-effect transistors (OFETs) and organic light emitting diodes (OLEDs).

It is desirable that the organic semiconducting materials are compatible with liquid processing techniques such as spin coating, solution casting or printing. Liquid processing techniques are convenient from the point of processability, and can also be applied to plastic substrates. Thus, organic semiconducting materials which are compatible with liquid processing techniques allow the production of low cost, light weight and, optionally also flexible, electronic devices, which is a clear advantage of these organic semiconducting materials compared to inorganic semiconducting materials.

Furthermore, it is desirable that the organic semiconducting materials are stable, in particular towards oxidation.

When used in organic field-effect transistors (OFETs), the organic semiconducting materials should show a high charge carrier mobility and a high on/off ratio.

The use of organic semiconducting materials in electronic devices, in particular in organic field effect transistors (OFETs) is known in the art.

Fuchigami, H.; Tsumura, A.; Koezuka, H. *Appl. Phys. Lett.* 1993, 63, 1372-1374 describes the use of poly(2,5-thienylenevinylene) in field-effect transistors.

Bao, Z.; Dobadalapur, A.; Lovinger, A. J. *Appl. Phys. Lett.* 1996, 69, 4108-4110 describes the use of regioregular poly(3-hexylthiophene) in field-effect transistors.

Zhang, M.; Tsao, H. N.; Pisula, W.; Yang, C.; Mishra, A. K.; Müllen, K. *J. Am. Chem. Soc.* 2007, 129, 3472-3473 describes polymers of formula

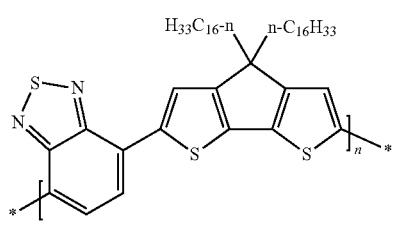

for use in organic field effect transistors (OFETs).

Xiao, S; Zhou H.; You, W. *Macromolecules* 2008, 41, 5688-5696 describes the following polymers

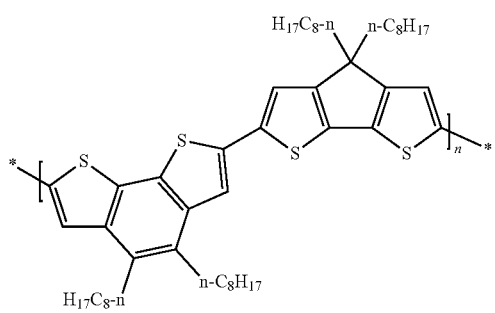

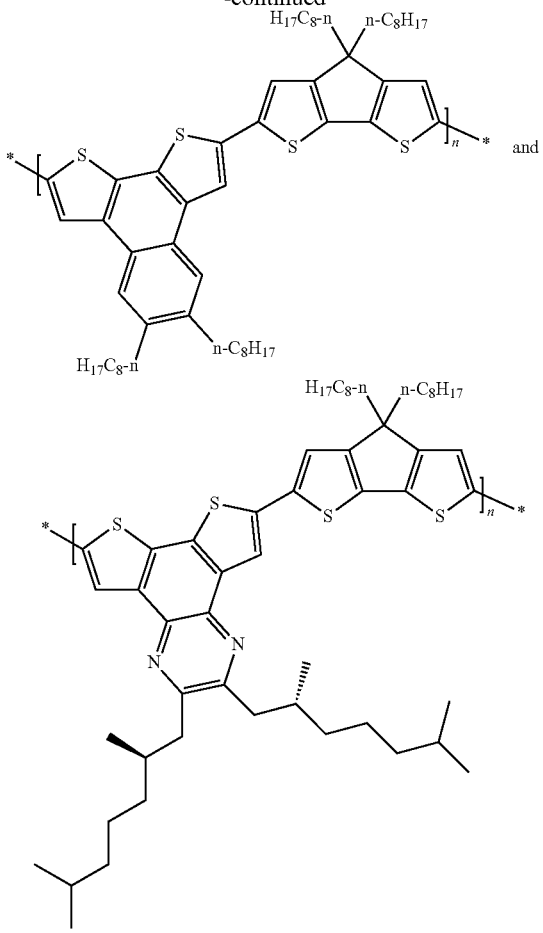

as donor materials for use in photovoltaic devices.

Scharber, M. C.; Koppe, M.; Gao, J.; Cordella, F.; Loi, M. A.; Denk, P.; Morana, M.; Egelhaaf, H.-J.; Forberich, K.; Dennler, G.; Gaudiana, R.; Waller, D.; Zhu, Z.; Shi, X.; Brabec, C. J. *Adv. Mater.* 2009, 21, 1-4 describes the following polymers

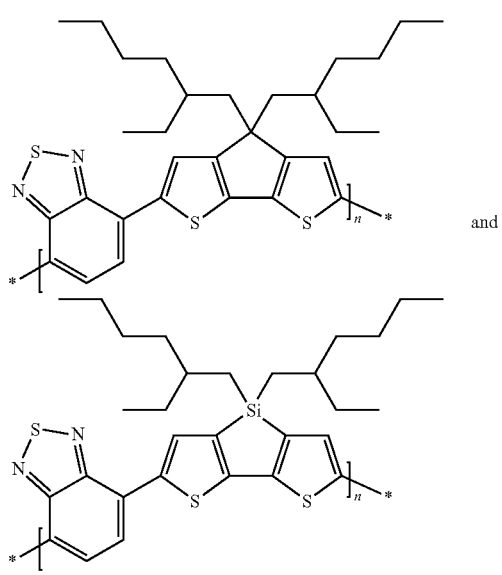

as donor materials for use in solar cells.

Rieger, R.; Beckmann, D.; Pisula, W.; Steffen, W.; Kastler, M.; Müllen K. *Adv. Mater.* 2010, 22, 83-86 describes the following polymers

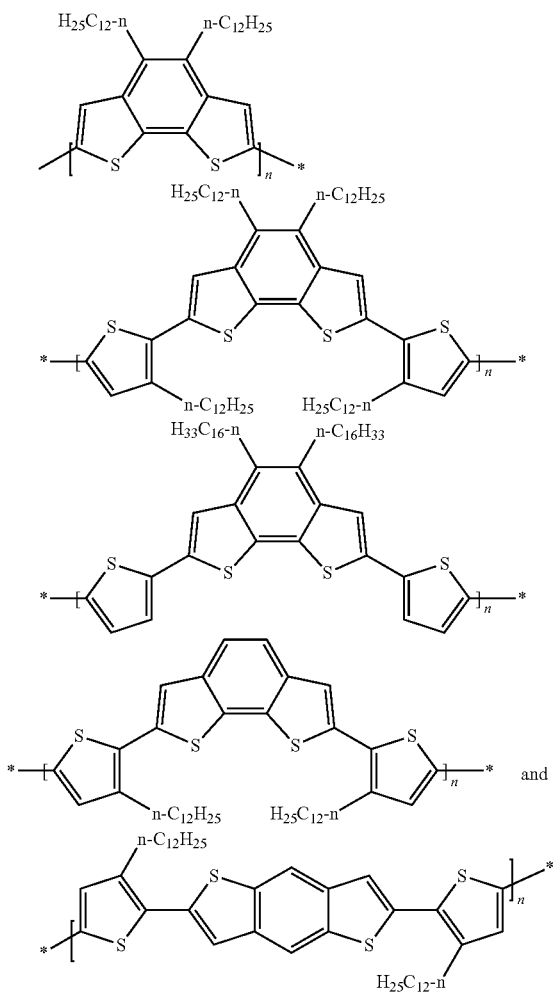

for use in organic field-effect transistor (OFET).

Kim, D. H.; Lee, B.-L-; Moon, H.; Kang, H. M.; Jeong, E. J.; Park, J.; Han, K.-M.; Lee, S.; Yoo, B. W.; Koo, B. W.; Kim, J. Y.; Lee, W. H.; Cho, K.; Becerril, H. A.; Z. Bao Z. *J. Am. Chem. Soc.* 2009, 131, 6124-6132 describes the polymer

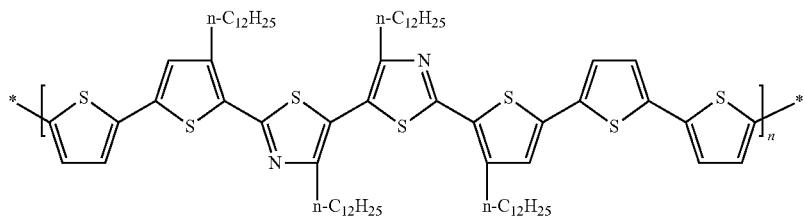

for use in organic field effect transistors (OFETs).

Osaka, I.; Sauvé, G.; Zhang, R.; Kowalewski, T.; McCullough R. D. *Adv. Mater.* 2007, 19, 4160-4165 describes the polymers

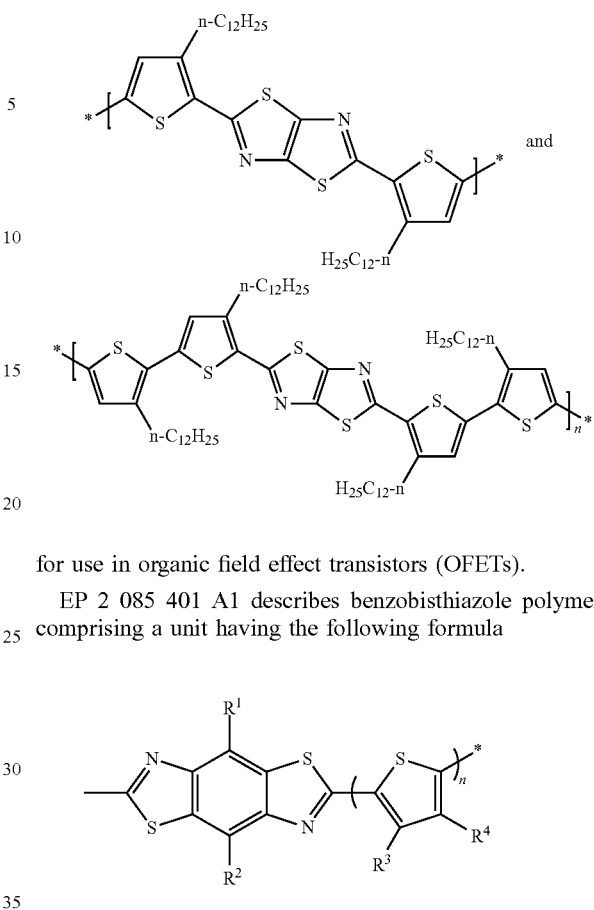

for use in organic field effect transistors (OFETs).

EP 2 085 401 A1 describes benzobisthiazole polymers comprising a unit having the following formula

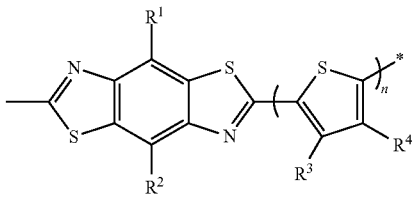

wherein each of $R^1$, $R^2$, $R^3$ and $R^4$ represents a hydrogen atom, a halogen atom, a substituted or unsubstituted alkyl group, a substituted or unsubstituted alkoxy group or a substituted or unsubstituted thioalkoxy group, wherein at least one of $R^1$, $R^2$, $R^3$ and $R^4$ is not a hydrogen atom, and n is a positive integer, wherein when n is 2 or more, each of $R^3$ is the same as or different from the others and each of $R^4$ is the same or different from the others, for use in transistors.

US 2008/0121281 A1 describes photovoltaic cells with thiazole-containing polymers such as bithiazole-containing polymers, cyclopentadithiazole-containing polymers or thiazolothiazole-containing polymers. Cyclopentadithiazole-containing polymers can be polymers which include a first comonomer repeat unit comprising a cyclopentadithiazole moiety, and a second comonomer repeat unit different from the first comonomer repeat unit. In some embodiments, the first comonomer repeat unit includes a cyclopentadithiazole moiety of formula

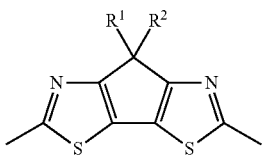

in which each of R¹ and R², independently, is H, $C_{1-20}$-aklyl, $C_{1-20}$-alkoxy, $C_{3-20}$-cycloalkyl, $C_{1-20}$-heterocycloalkyl, aryl, heteroaryl, halo, CN, OR, C(O)R, C(O)OR, or $SO_2R$; R being H, $C_{1-20}$-alkyl, $C_{1-20}$-alkoxy, $C_{3-20}$-cycloalkyl, $C_{1-20}$-heterocycloalkyl, aryl, or heteroaryl.

WO 2009/069687 describes a polymer represented by the general formula

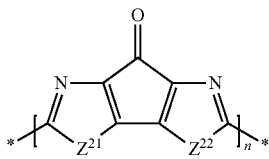

wherein $Z^{21}$ and $Z^{22}$ independently represent, for example, —S—.

It is the object of the present invention to provide organic semiconducting materials suitable for use in electronic devices, in particular in organic field effect transistors (OFETs), where the organic semiconducting materials show a high oxidative stability, particularly in ambient conditions, and are compatible with liquid processing techniques. The organic field effect transistors comprising the organic semiconducting materials should show an acceptable charge carrier mobility and current on/off ratio.

This object is solved by the compound, oligomer or polymer of claim 1 and the electronic device of claim 19.

The compound, oligomer or polymer of the present invention are of formula

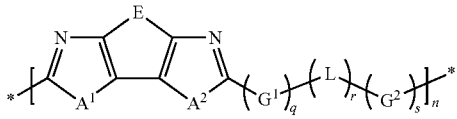

wherein
$A^1$ and $A^2$ can be the same or different and are S or Se,
E is selected from the group consisting of

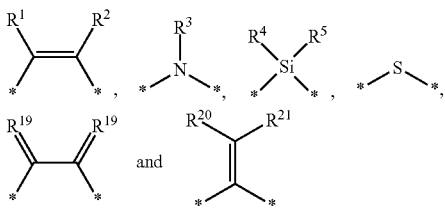

wherein
$R^1$ and $R^2$ can be the same or different and are H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^1$—$R^6$, —$X^2$—$Ar^1$, —$X^2$—$Ar^2$—$Ar^1$, —$X^2$—$Ar^2$—$R^7$ or —$X^2$—$Ar^2$—$Ar^3$—$R^7$,
wherein
$X^1$ at each occurrence is independently —O—, —$[Z^1$—O$]_a$—, —[O—$Z^1]_a$—O—, —S—, —[$Z^1$—S—$]_a$—, —[S—$Z^1]_a$—S—, —S(O), —C(O), —C(O)O—, —C(O)$NR^8$—, C(O)S—, —O(CO)—, —S(CO)—, —$NR^8$C(O)— or —$NR^8$—,
wherein
$Z^1$ at each occurrence is independently $C_{1-6}$-alkylene, $C_{2-6}$-alkenylene or $C_{1-6}$-haloalkylene,
a at each occurrence is independently an integer from 1 to 10 and
$R^8$ at each occurrence is independently H, $C_{1-20}$-alkyl, or —$Z^2$—$C_{6-14}$-aryl,
wherein
$Z^2$ at each occurrence is independently $C_{1-6}$-alkylene, $C_{2-6}$-alkenylene, $C_{1-6}$-haloalkylene or a covalent bond,
$R^6$ at each occurrence is independently $C_{1-3}$-alkyl, $C_{2-30}$-alkenyl or $C_{1-30}$-haloalkyl,
$X^2$ at each occurrence is independently —$Z^3$—O—$Z^4$—, —$Z^3$—S—$Z^4$—, —S(O)—, —C(O)—, —C(O)O—, —(CO)$NR^9$—, —C(O)S—, —O(CO)—, —S(CO)—, —$NR^9$C(O)—, —$NR^9$—, —$Z^3$—$SiR^9{}_2$—$Z^4$—, $C_{1-30}$-alkylene, $C_{2-30}$-alkenylene, $C_{1-30}$-haloalkylene or a covalent bond,
wherein
$Z^3$ and $Z^4$ at each occurrence are independently $C_{1-6}$-alkylene, $C_{2-6}$-alkenylene, $C_{1-6}$-haloalkylene or a covalent bond, and
$R^9$ at each occurrence is independently H, $C_{1-20}$-alkyl, or —$Z^5$—$C_{6-14}$-aryl,
wherein
$Z^5$ at each occurrence is independently $C_{1-6}$-alkylene, $C_{2-6}$-alkenylene, $C_{1-6}$-haloalkylene or a covalent bond,
$Ar^1$ at each occurrence is independently $C_{6-14}$-aryl or monovalent 5 to 14 membered aromatic hetrocyclic residue, each optionally substituted with 1 to 5 substituents $R^a$, wherein each $R^a$ is independently selected from the group consisting of halogen, CN, $C_{1-6}$-alkyl, $C_{1-6}$-alkoxy and $C_{1-6}$-haloalkyl,
$Ar^2$ and $Ar^3$ at each occurrence are independently $C_{6-14}$-arylene or bivalent 5 to 14 membered aromatic heterocyclic residue, each optionally substituted with 1 to 4 substituents $R^b$, wherein each $R^b$ is independently selected from the group consisting of halogen, CN, $C_{1-6}$-alkyl, $C_{1-6}$-alkoxy and $C_{1-6}$-haloalkyl, and
$R^7$ at each occurrence is independently $C_{1-20}$-alkyl, $C_{2-20}$-alkenyl, $C_{1-20}$-haloalkyl, $C_{1-20}$-alkoxy, —$X^3$—$Ar^4$, —$X^3$—$Ar^5$—$Ar^4$, —$X^3$—$Ar^5$—$R^{10}$, or —$X^3$—$Ar^5$—$Ar^6$—$R^{10}$,
wherein
$X^3$ at each occurrence is independently —$Z^6$—O—$Z^7$—, —$Z^6$—S—$Z^7$, —S(O)—, —C(O)—, —C(O)O—, —(CO)$NR^{11}$—, —C(O)S—, —O(CO)—, —S(CO)—, —$NR^{11}$C(O)—, —$NR^{11}$—, —$Z^6$—$SiR^{11}{}_2$—$Z^7$—, $C_{1-30}$-alkylene, $C_{2-30}$-alkenylene, $C_{1-30}$-haloalkylene or a covalent bond,
wherein
$Z^6$ and $Z^7$ at each occurrence are independently $C_{1-6}$-alkylene, $C_{2-6}$-alkenylene, $C_{1-6}$-haloalkylene or a covalent bond, and $R^{11}$ at each occurrence is independently H, $C_{1-20}$-alkyl or —$Z^8$—$C_{6-14}$-aryl, wherein $Z^8$ at each occurrence is independently $C_{1-6}$-alkylene, $C_{2-6}$-alkenylene, $C_{1-6}$-haloalkylene or a covalent bond, $Ar^4$ at each occurrence is independently $C_{6-14}$-aryl or monovalent 5 to 14 membered aromatic heterocyclic residue, each optionally substituted with 1 to 5 substituents $R^c$, wherein each $R^c$ is independently selected from the group consisting of halogen, CN, $C_{1-6}$-alkyl, $C_{1-6}$-alkoxy and $C_{1-6}$-haloalkyl, $Ar^5$ and $Ar^6$ at each occurrence are independently $C_{6-14}$-arylene or bivalent 5 to 14 membered aromatic heterocyclic residue, each optionally substituted with 1 to 4 substituents $R^d$, wherein each $R^d$ is independently selected from the group consisting of halogen, CN, $C_{1-6}$-alkyl, $C_{1-6}$-alkoxy and $C_{1-6}$-haloalkyl, and $R^{10}$ at each occurrence is independently $C_{1-20}$-alkyl, $C_{2-20}$-alkenyl, $C_{1-20}$-haloalkyl or $C_{1-20}$-alkoxy, $R^3$, $R^4$ and $R^5$ can be the same or different and are H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^4$—$R^{12}$, —$X^5$—$Ar^7$, —$X^5$—$Ar^8$—$Ar^7$, —$X^5$—$Ar^8$—$R^{13}$ or —$X^5$—$Ar^8$—$Ar^9$—$R^{13}$, wherein $X^4$ at each occurrence is independently —[$Z^9$—O]$_b$—, —[$Z^9$—S]$_b$—, —S(O)—, —C(O)—, —C(O)O—, —C(O)NR$^{14}$— or C(O)S—, wherein $Z^9$ at each occurrence is independently $C_{1-6}$-alkylene, $C_{2-6}$-alkenylene or $C_{1-6}$-haloalkylene, b at each occurrence is independently an integer from 1 to 10 and $R^{14}$ at each occurrence is independently H, $C_{1-20}$-alkyl, or —$Z^{10}$—$C_{6-14}$-aryl, wherein $Z^{10}$ at each occurrence is independently $C_{1-6}$-alkylene, $C_{2-6}$-alkenylene, $C_{1-6}$-haloalkylene or a covalent bond, $R^{12}$ at each occurrence is independently $C_{1-30}$-alkyl, $C_{2-30}$-alkenyl or $C_{1-30}$-haloalkyl, $X^5$ at each occurrence is independently —$Z^{11}$—O—$Z^{12}$—, —S(O)—, —C(O)—, —C(O)O—, —(CO)NR$^{15}$, —C(O)S—, —$Z^{11}$—SiR$^{15}_2$—$Z^{12}$—, $C_{1-30}$-alkylene, $C_{2-30}$-alkenylene, $C_{1-30}$-haloalkylene or a covalent bond, wherein $Z^{11}$ at each occurrence is independently $C_{1-6}$-alkylene, $C_{2-6}$-alkenylene or $C_{1-6}$-haloalkylene, $Z^{12}$ at each occurrence is independently $C_{1-6}$-alkylene, $C_{2-6}$-alkenylene, $C_{1-6}$-haloalkylene or a covalent bond, and $R^{15}$ at each occurrence is independently H, $C_{1-20}$-alkyl, or —$Z^{13}$—$C_{6-14}$-aryl, wherein $Z^{13}$ at each occurrence is independently $C_{1-6}$-alkylene, $C_{2-6}$-alkenylene, $C_{1-6}$-haloalkylene or a covalent bond, $Ar^7$ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl, $Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl and $R^{13}$ at each occurrence is independently $C_{1-20}$-alkyl, $C_{2-20}$-alkenyl, $C_{1-20}$-haloalkyl, $C_{1-20}$-alkoxy, —$X^6$—$Ar^{10}$, —$X^6$—$Ar^{11}$—$Ar^{10}$, —$X^6$—$Ar^{11}$—$R^{16}$, or —$X^6$—$Ar^{11}$—$Ar^{12}$—$R^{17}$, wherein $X^6$ at each occurrence is independently —$Z^{14}$—O—$Z^{15}$—, —$Z^{14}$—S—$Z^{15}$—, —S(O)—, —C(O)—, —C(O)O—, —(CO)NR$^{18}$, —C(O)S—, —O(CO)—, —S(CO)—, —NR$^{18}$C(O)—, —NR$^{18}$—, —$Z^{14}$—SiR$^{18}_2$—$Z^{15}$—, $C_{1-30}$-alkylene, $C_{2-30}$-alkenylene, $C_{1-30}$-haloalkylene or a covalent bond, wherein $Z^{14}$ and $Z^{15}$ at each occurrence are independently $C_{1-6}$-alkylene, $C_{2-6}$-alkenylene, $C_{1-6}$-haloalkylene or a covalent bond, and $R^{18}$ at each occurrence is independently H, $C_{1-20}$-alkyl or —$Z^{16}$—$C_{6-14}$-aryl, wherein $Z^{16}$ at each occurrence is independently $C_{1-6}$-alkylene, $C_{2-6}$-alkenylene, $C_{1-6}$-haloalkylene or a covalent bond, $Ar^{10}$ at each occurrence is independently $C_{6-14}$-aryl or monovalent 5 to 14 membered aromatic heterocyclic residue, each optionally substituted with 1 to 5 substituents $R^g$, wherein each $R^g$ is independently selected from the group consisting of halogen, CN, $C_{1-6}$-alkoxy and $C_{1-6}$-haloalkyl, $Ar^{11}$ and $Ar^{12}$ at each occurrence are independently $C_{6-14}$-arylene or bivalent 5 to 14 membered aromatic heterocyclic residue, each optionally substituted with 1 to 4 substituents $R^h$, wherein each $R^h$ is independently selected from the group consisting of halogen, CN, $C_{1-6}$-alkyl, $C_{1-6}$-alkoxy and $C_{1-6}$-haloalkyl and $R^{17}$ at each occurrence is independently $C_{1-20}$-alkyl, $C_{2-20}$-alkenyl, $C_{1-20}$-haloalkyl or $C_{1-20}$-alkoxy, $R^{19}$ is O or $C(CN)_2$, and $R^{20}$ and $R^{21}$ are the same or different and are $R^{22}$ or CN, wherein $R^{22}$ has the same meaning as $R^1$, $G^1$ and $G^2$ are the same or different and are phenylene or a monocyclic bivalent 5 to 8 membered aromatic heterocyclic residue, which phenylene and monocyclic bivalent 5 to 8 membered aromatic heterocyclic residue are optionally substituted with 1 to 4 substituents $R^i$, wherein each $R^i$ is independently selected from the group consisting of halogen, —CN, —NO$_2$, —OH, $C_{1-30}$-alkyl, $C_{2-30}$-alkenyl, $C_{2-30}$-alkynyl, —$Z^{17}$—O—$C_{1-30}$-alkyl, —$Z^{17}$—S—$C_{1-30}$-alkyl, —$Z^{17}$—$C_{3-10}$-cycloalkyl, —$Z^{17}$—$C_{5-10}$-cycloalkenyl, —$Z^{17}$—$C_{8-10}$-cycloalkynyl, —$Z^{17}$—$C_{6-14}$-aryl, —$Z^{17}$-monovalent 3 to 12 membered aliphatic heterocyclic residue and —$Z^{17}$-monovalent 5 to 14 membered aromatic heterocyclic residue, wherein $C_{1-30}$-alkyl, $C_{2-30}$-alkenyl, $C_{2-30}$-alkynyl, $C_{3-10}$-cycloalkyl, $C_{5-10}$-cycloalkenyl, $C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN, —NO$_2$, *=O, —OH, —NH$_2$, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_m$H, —S(O)$_m$—$C_{1-20}$-alkyl, —S(O)$_2$OH, —S(O)$_m$—O$C_{1-20}$-alkyl, —S(O)$_m$—O$C_{6-14}$-aryl, —CHO, —C(O)—$C_{1-20}$-alkyl, —C(O)—$C_{6-14}$-aryl, —C(O)OH, —C(O)—O$C_{1-20}$-alkyl, —C(O)—O$C_{6-14}$-aryl, —C(O)NH$_2$, —C(O)NH—$C_{1-20}$-alkyl, —C(O)N($C_{1-20}$-alkyl)$_2$, —C(O)NH—$C_{6-14}$-aryl, —C(O)N($C_{1-20}$-alkyl)-$C_{6-14}$-aryl, —C(O)N($C_{6-14}$-aryl)$_2$, —C(S)NH$_2$, —C(S)NH—$C_{1-20}$-alkyl, —C(S)N($C_{1-20}$-alkyl)$_2$, —C(S)N($C_{6-14}$-aryl)$_2$, —C(S)N($C_{1-20}$-alkyl)-$C_{6-14}$-aryl, —C(S)NH—$C_{6-14}$-aryl, —S(O)$_m$NH$_2$, —S(O)$_m$NH($C_{1-20}$-alkyl), —S(O)$_m$N($C_{1-20}$-alkyl)$_2$, —S(O)$_m$NH($C_{6-14}$-aryl), —S(O)$_m$N($C_{1-20}$-alkyl)-$C_{6-14}$-aryl, —S(O)$_m$N($C_{6-14}$-aryl)$_2$, SiH$_3$, SiH($C_{1-20}$-alkyl)$_2$, SiH$_2$($C_{1-20}$-alkyl) and Si($C_{1-20}$-alkyl)$_3$, and wherein $C_{3-10}$-cycloalkyl, $C_{5-10}$-cycloalkenyl, —$C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{2-20}$-alkenyl, $C_{2-20}$-alkynyl, $C_{1-20}$-alkoxy, $C_{1-20}$-haloalkyl, wherein $Z^{17}$ at each occurrence is independently $C_{1-6}$-alkylene, $C_{2-6}$-alkenylene, $C_{1-6}$-haloalkylene or a covalent bond, and m at each occurrence is independently 0, 1 or 2, L is $C_{6-24}$-arylene or a bivalent 5 to 18 membered aromatic heterocyclic residue, wherein $C_{6-24}$-arylene and bivalent 5 to 18 membered aromatic heterocyclic residue are optionally substituted with 1 to 4 substituents $R^l$, wherein each $R^l$ is independently selected from the group consisting of halogen, —CN, —NO$_2$, *=O, OH, *=C($C_{1-30}$-alkyl)$_2$, $C_{1-30}$-alkyl, $C_{2-30}$-alkenyl, $C_{2-30}$-alkynyl, —$Z^{18}$—O—$C_{1-30}$-alkyl, —$Z^{18}$—S—$C_{1-30}$-alkyl, —$Z^{18}$—$C_{3-30}$-cycloalkyl, —$Z^{18}$—$C_{5-10}$-cycloalkenyl, —$Z^{18}$—$C_{8-10}$-cycloalkynyl, —$Z^{18}$—$C_{6-14}$-aryl, —$Z^{18}$-monovalent 3 to 12 membered aliphatic heterocyclic residue and —$Z^{18}$-monovalent 5 to 14 membered aromatic heterocyclic residue, wherein $C_{1-30}$-alkyl, $C_{2-30}$-alkenyl, $C_{2-30}$-alkynyl, $C_{3-10}$-cycloalkyl, $C_{5-10}$-cycloalkenyl, $C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN, —NO$_2$, *=O, —OH, —NH$_2$, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_o$H, —S(O)$_o$—$C_{1-20}$-alkyl, —S(O)$_2$OH, —S(O)$_o$—O$C_{1-20}$-alkyl, —S(O)$_o$—O$C_{6-14}$-aryl, —CHO, —C(O)—$C_{1-20}$-alkyl, —C(O)—$C_{6-14}$-aryl, —C(O)OH, —C(O)—O$C_{1-20}$-alkyl, —C(O)—O$C_{6-14}$-aryl, —C(O)NH$_2$, —C(O)NH—$C_{1-20}$-alkyl, —C(O)N($C_{1-20}$-alkyl)$_2$, —C(O)NH—$C_{6-14}$-aryl, —C(O)N($C_{1-20}$-alkyl)-$C_{6-14}$-aryl, —C(O)N($C_{6-14}$-aryl)$_2$, —C(S)NH$_2$, —C(S)NH—$C_{1-20}$-alkyl, —C(S)N($C_{1-20}$-alkyl)$_2$, —C(S)N($C_{6-14}$-aryl)$_2$, —C(S)N($C_{1-20}$-alkyl)-$C_{6-14}$-aryl, —C(S)NH—$C_{6-14}$-aryl, —S(O)$_o$NH$_2$, —S(O)$_o$NH($C_{1-20}$-alkyl), —S(O)$_o$N($C_{1-20}$-alkyl)$_2$, —S(O)$_o$NH($C_{6-14}$-aryl), —S(O)$_o$N($C_{1-20}$-alkyl)-$C_{6-14}$-aryl, —S(O)$_o$N($C_{6-14}$-aryl)$_2$, SiH$_3$, SiH($C_{1-20}$-alkyl)$_2$, SiH$_2$($C_{1-20}$-alkyl) and Si($C_{1-20}$-alkyl)$_3$, and wherein $C_{3-10}$-cycloalkyl, $C_{5-10}$-cycloalkenyl, —$C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R''$, wherein each $R''$ is independently selected from the group consisting of $C_{1-20}$-alkyl, $C_{2-20}$-alkenyl, $C_{2-20}$-alkynyl, $C_{1-20}$-alkoxy, —S—$C_{1-20}$-alkyl, $C_{1-20}$-haloalkyl, wherein $Z^{18}$ at each occurrence is independently $C_{1-6}$-alkylene, $C_{2-6}$-alkenylene, $C_{1-6}$-haloalkylene or a covalent bond, and o at each occurrence is independently 0, 1 or 2, or L is

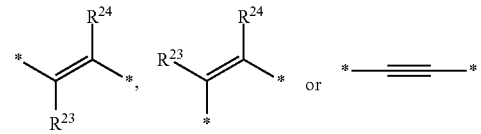

wherein $R^{23}$ and $R^{24}$ can be the same or different and are H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^7$—$R^{25}$, —$X^8$—$Ar^{13}$, —$X^8$—$Ar^{14}$—$Ar^{13}$, —$X^8$—$Ar^{14}$—$R^{26}$ or —$X^8$—$Ar^{14}$—$Ar^{15}$—$R^{26}$, wherein $X^7$ at each occurrence is independently —O—, —[$Z^{19}$—O]$_c$—, —[O—$Z^{19}$]$_c$—O—, —S—, —[$Z^{19}$—S—]$_c$—, —[S—$Z^{19}$]$_c$—S—, —S(O), —C(O)—, —C(O)O—, —C(O)NR$^{27}$—, C(O)S—, —O(CO)—, —S(CO)—, —NR$^{27}$C(O)— or —NR$^{27}$—, wherein $Z^{19}$ at each occurrence is independently $C_{1-6}$-alkylene, $C_{2-6}$-alkenylene or $C_{1-6}$-haloalkylene, c at each occurrence is independently an integer from 1 to 10 and $R^{27}$ at each occurrence is independently H, $C_{1-20}$-alkyl, or $C_{6-14}$-aryl, wherein $Z^{20}$ at each occurrence is independently $C_{1-6}$-alkylene, $C_{2-6}$-alkenylene, $C_{1-6}$-haloalkylene or a covalent bond, $R^{25}$ at each occurrence is independently $C_{1-30}$-alkyl, $C_{2-30}$-alkenyl or $C_{1-30}$-haloalkyl, $X^8$ at each occurrence is independently —$Z^{21}$—O—$Z^{22}$—, —$Z^{21}$—S—$Z^{22}$—, —S(O)—, —C(O)—, —C(O)O—, —(CO)NR$^{28}$, —C(O)S—, —O(CO)—, —S(CO)—, —NR$^{28}$C(O)—, —NR$^{28}$—, —$Z^{21}$—SiR$^{28}{}_2$—$Z^{22}$—, $C_{1-30}$-alkylene, $C_{2-30}$-alkenylene, $C_{1-30}$-haloalkylene or a covalent bond, wherein $Z^{21}$ and $Z^{22}$ at each occurrence are independently $C_{1-6}$-alkylene, $C_{2-6}$-alkenylene, $C_{1-6}$-haloalkylene or a covalent bond, and $R^{28}$ at each occurrence is independently H, $C_{1-20}$-alkyl, or —$Z^{23}$—$C_{6-14}$-aryl, wherein
Z$^{23}$ at each occurrence is independently C$_{1-6}$-alkylene, C$_{2-6}$-alkenylene, C$_{1-6}$-haloalkylene or a covalent bond, Ar$^{13}$ at each occurrence is independently C$_{6-14}$-aryl or monovalent 5 to 14 membered aromatic hetrocyclic residue, each optionally substituted with 1 to 5 substituents R$^o$, wherein each R$^o$ is independently selected from the group consisting of halogen, CN, C$_{1-6}$-alkyl, C$_{1-6}$-alkoxy and C$_{1-6}$-haloalkyl, Ar$^{14}$ and Ar$^{15}$ at each occurrence are independently C$_{6-14}$-arylene or bivalent 5 to 14 membered aromatic heterocyclic residue, each optionally substituted with 1 to 4 substituents R$^p$, wherein each R$^p$ is independently selected from the group consisting of halogen, CN, C$_{1-6}$-alkyl, C$_{1-6}$-alkoxy and C$_{1-6}$-haloalkyl, and R$^{26}$ at each occurrence is independently C$_{1-20}$-alkyl, C$_{2-20}$-alkenyl, C$_{1-20}$-haloalkyl, C$_{1-20}$-alkoxy, —X$^9$—Ar$^{16}$, —X$^9$—Ar$^{17}$—Ar$^{16}$, —X$^9$—Ar$^{17}$—R$^{29}$, or —X$^9$—Ar$^{17}$—Ar$^{18}$—R$^{29}$,
wherein X$^9$ at each occurrence is independently —Z$^{24}$—O—Z$^{25}$—, —Z$^{24}$—S—Z$^{25}$—, —S(O)—, —C(O)—, —C(O)O—, —(CO)NR$^{30}$, —C(O)S—, —O(CO)—, —S(CO)—, —NR$^{30}$C(O)—, —NR$^{30}$—, —Z$^{24}$—SiR$^{30}$$_2$—Z$^{25}$—, C$_{1-30}$-alkylene, C$_{2-30}$-alkenylene, C$_{1-30}$-haloalkylene or a covalent bond,
wherein Z$^{24}$ and Z$^{25}$ at each occurrence are independently C$_{1-6}$-alkylene, C$_{2-6}$-alkenylene, C$_{1-6}$-haloalkylene or a covalent bond, and R$^{30}$ at each occurrence is independently H, C$_{1-20}$-alkyl or —Z$^{26}$—C$_{6-14}$-aryl,
wherein Z$^{26}$ at each occurrence is independently C$_{1-6}$-alkylene, C$_{2-6}$-alkenylene, C$_{1-6}$-haloalkylene or a covalent bond, Ar$^{16}$ at each occurrence is independently C$_{6-14}$-aryl or monovalent 5 to 14 membered aromatic heterocyclic residue, each optionally substituted with 1 to 5 substituents R$^q$, wherein each R$^q$ is independently selected from the group consisting of halogen, CN, C$_{1-6}$-alkyl, C$_{1-6}$-alkoxy and C$_{1-6}$-haloalkyl, Ar$^{17}$ and Ar$^{18}$ at each occurrence are independently C$_{6-14}$-arylene or bivalent 5 to 14 membered aromatic heterocyclic residue, each optionally substituted with 1 to 4 substituents R$^r$, wherein each R$^r$ is independently selected from the group consisting of halogen, CN, C$_{1-6}$-alkoxy and C$_{1-6}$-haloalkyl, and R$^{29}$ at each occurrence is independently C$_{1-20}$-alkyl, C$_{2-20}$-alkenyl, C$_{1-20}$-haloalkyl or C$_{1-20}$-alkoxy, q and s are the same or different and are 0, 1, 2, 3, 4 or 5,
r is 0, 1 or 2,
and
n is an integer from 1 to 10,000.

Preferred are oligomers or polymers of formula

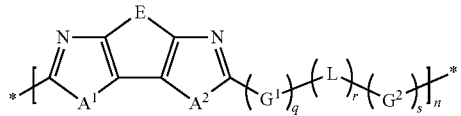

(1)

wherein
A$^1$ and A$^2$ can be the same or different and are S or Se,
E is selected from the group consisting of

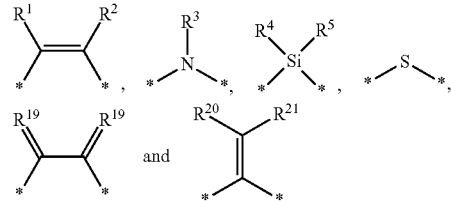

and wherein
R$^1$ and R$^2$ can be the same or different and are H, halogen, —CN, C$_{1-30}$-alkyl, C$_{2-30}$-alkenyl, C$_{2-20}$-alkynyl, C$_{3-10}$-cycloalkyl, C$_{5-10}$-cycloalkenyl, C$_{8-10}$-cycloalkynyl, C$_{1-30}$-haloalkyl, monovalent 3 to 12 membered aliphatic heterocyclic residue, —X$^1$—R$^6$, —X$^2$—Ar$^1$, —X$^2$—Ar$^2$—Ar$^1$, —X$^2$—Ar$^2$—R$^7$ or —X$^2$—Ar$^2$—Ar$^3$—R$^7$,
wherein X$^1$ at each occurrence is independently —O—, —[Z$^1$—O]$_a$—, —[O—Z$^1$]$_a$—O—, —S—, —[Z$^1$—S]$_a$—, —[S—Z$^1$]$_a$—S—, —S(O), —C(O)—, —C(O)O—, —C(O)NR$^8$—, C(O)S—, —O(CO)—, —S(CO)—, —NR$^8$C(O)— or —NR$^8$—,
wherein Z$^1$ at each occurrence is independently C$_{1-6}$-alkylene, C$_{2-6}$-alkenylene or C$_{1-6}$-haloalkylene,
a at each occurrence is independently an integer from 1 to 10 and
R$^8$ at each occurrence is independently H, C$_{1-20}$-alkyl, or —Z$^2$—C$_{6-14}$-aryl,
wherein Z$^2$ at each occurrence is independently C$_{1-6}$-alkylene, C$_{2-6}$-alkenylene, C$_{1-6}$-haloalkylene or a covalent bond, R$^6$ at each occurrence is independently C$_{1-30}$-alkyl, C$_{2-30}$-alkenyl or C$_{1-30}$-haloalkyl, X$^2$ at each occurrence is independently —Z$^3$—O—Z$^4$—, —Z$^3$—S—Z$^4$—, —S(O)—, —O(O)—, —C(O)O—, —(CO)NR$^9$, —C(O)S—, —O(CO)—, —S(CO)—, —NR$^9$C(O)—, —NR$^9$—, —Z$^3$—SiR$^9$$_2$—Z$^4$—, C$_{1-30}$-alkylene, C$_{2-30}$-alkenylene, C$_{1-30}$-haloalkylene or a covalent bond,
wherein Z$^3$ and Z$^4$ at each occurrence are independently C$_{1-6}$-alkylene, C$_{2-6}$-alkenylene, C$_{1-6}$-haloalkylene or a covalent bond, and R$^9$ at each occurrence is independently H, C$_{1-20}$-alkyl, or —Z$^5$—C$_{6-14}$-aryl,
wherein Z$^5$ at each occurrence is independently C$_{1-6}$-alkylene, C$_{2-6}$-alkenylene, C$_{1-6}$-haloalkylene or a covalent bond, Ar$^1$ at each occurrence is independently C$_{6-14}$-aryl or monovalent 5 to 14 membered aromatic hetrocyclic residue, each optionally substituted with 1 to 5 substituents R$^a$, wherein each R$^a$ is independently selected from the group consisting of halogen, CN, C$_{1-6}$-alkyl, C$_{1-6}$-alkoxy and C$_{1-6}$-haloalkyl, Ar$^2$ and Ar$^3$ at each occurrence are independently C$_{6-14}$-arylene or bivalent 5 to 14 membered aromatic heterocyclic residue, each optionally substituted with 1 to 4 substituents $R^b$, wherein each $R^b$ is independently selected from the group consisting of halogen, CN, $C_{1-6}$-alkyl, $C_{1-6}$-alkoxy and $C_{1-6}$-haloalkyl, and $R^7$ at each occurrence is independently $C_{1-20}$-alkyl, $C_{2-20}$-alkenyl, $C_{1-20}$-haloalkyl, $C_{1-20}$-alkoxy, —$X^3$—$Ar^4$, —$X^3$—$Ar^5$—$Ar^4$, —$X^3$—$Ar^5$—$R^{10}$, or —$X^3$—$Ar^5$—$Ar^6$—$R^{10}$,
wherein
$X^3$ at each occurrence is independently —$Z^6$—O—$Z^7$—, —$Z^6$—S—$Z^7$—, —S(O)—, —C(O)—, —C(O)O—, —(CO)NR$^{11}$—, —C(O)S—, —O(CO)—, —S(CO)—, —NR$^{11}$C(O)—, —NR$^{11}$—, —$Z^6$—SiR$^{11}_2$—$Z^7$—, $C_{1-30}$-alkylene, $C_{2-30}$-alkenylene, $C_{1-30}$-haloalkylene or a covalent bond,
wherein
$Z^6$ and $Z^7$ at each occurrence are independently $C_{1-6}$-alkylene, $C_{2-6}$-alkenylene, $C_{1-6}$-haloalkylene or a covalent bond, and
$R^{11}$ at each occurrence is independently H, $C_{1-20}$-alkyl or —$Z^8$—$C_{6-14}$-aryl,
wherein
$Z^8$ at each occurrence is independently $C_{1-6}$-alkylene, $C_{2-6}$-alkenylene, $C_{1-6}$-haloalkylene or a covalent bond,
$Ar^4$ at each occurrence is independently $C_{6-14}$-aryl or monovalent 5 to 14 membered aromatic heterocyclic residue, each optionally substituted with 1 to 5 substituents $R^c$, wherein each $R^c$ is independently selected from the group consisting of halogen, CN, $C_{1-6}$-alkyl, $C_{1-6}$-alkoxy and $C_{1-6}$-haloalkyl,
$Ar^5$ and $Ar^6$ at each occurrence are independently $C_{6-14}$-arylene or bivalent 5 to 14 membered aromatic heterocyclic residue, each optionally substituted with 1 to 4 substituents $R^d$, wherein each $R^d$ is independently selected from the group consisting of halogen, CN, $C_{1-6}$-alkoxy and $C_{1-6}$-haloalkyl, and
$R^{10}$ at each occurrence is independently $C_{1-20}$-alkyl, $C_{2-20}$-alkenyl, $C_{1-20}$-haloalkyl or $C_{1-20}$-alkoxy, $R^3$, $R^4$ and $R^5$ can be the same or different and are H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^4$—$R^{12}$, —$X^5$—$Ar^7$, —$X^5$—$Ar^8$—$Ar^7$, —$X^5$—$Ar^8$—$R^{13}$ or —$X^5$—$Ar^8$—$Ar^9$—$R^{13}$,
wherein
$X^4$ at each occurrence is independently —[$Z^9$—O]$_b$—, —[$Z^9$—S]$_b$—, —S(O)—, —C(O)—, —C(O)O—, —C(O)NR$^{14}$— or C(O)S—,
wherein
$Z^9$ at each occurrence is independently $C_{1-6}$-alkylene, $C_{2-6}$-alkenylene or $C_{1-6}$-haloalkylene,
b at each occurrence is independently an integer from 1 to 10 and
$R^{14}$ at each occurrence is independently H, $C_{1-20}$-alkyl, or —$Z^{10}$—$C_{6-14}$-aryl,
wherein
$Z^{10}$ at each occurrence is independently $C_{1-6}$-alkylene, $C_{2-6}$-alkenylene, $C_{1-6}$-haloalkylene or a covalent bond,
$R^{12}$ at each occurrence is independently $C_{1-30}$-alkyl, $C_{2-30}$-alkenyl or $C_{1-30}$-haloalkyl, $X^5$ at each occurrence is independently —$Z^{11}$—O—$Z^{12}$—, —$Z^{11}$—S—$Z^{12}$—, —S(O)—, —C(O)—, —C(O)O—, —(CO)NR$^{15}$, —C(O)S—, —$Z^{11}$—SiR$^{15}_2$—$Z^{12}$—, $C_{1-30}$-alkylene, $C_{2-30}$-alkenylene, $C_{1-30}$-haloalkylene or a covalent bond,
wherein
$Z^{11}$ at each occurrence is independently $C_{1-6}$-alkylene, $C_{2-6}$-alkenylene or $C_{1-6}$-haloalkylene,
$Z^{12}$ at each occurrence is independently $C_{1-6}$-alkylene, $C_{2-6}$-alkenylene, $C_{1-6}$-haloalkylene or a covalent bond, and
$R^{15}$ at each occurrence is independently H, $C_{1-20}$-alkyl, or —$Z^{13}$—$C_{6-14}$-aryl,
wherein
$Z^{13}$ at each occurrence is independently $C_{1-6}$-alkylene, $C_{2-6}$-alkenylene, $C_{1-6}$-haloalkylene or a covalent bond,
$Ar^7$ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl,
$Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl and
$R^{13}$ at each occurrence is independently $C_{1-20}$-alkyl, $C_{2-20}$-alkenyl, $C_{1-20}$-haloalkyl, $C_{1-20}$-alkoxy, —$X^6$—$Ar^{10}$, —$X^6$—$Ar^{11}$—$Ar^{10}$, —$X^6$—$Ar^{11}$—$R^{16}$, or —$X^6$—$Ar^{11}$—$Ar^{12}$—$R^{17}$,
wherein
$X^6$ at each occurrence is independently —$Z^{14}$—O—$Z^{15}$—, —$Z^{14}$—S—$Z^{15}$—, —S(O)—, —C(O)—, —C(O)O—, —(CO)NR$^{18}$, —C(O)S—, —O(CO)—, —S(CO)—, —NR$^{18}$C(O)—, —NR$^{18}$—, —$Z^{14}$—SiR$^{18}_2$—$Z^{15}$—, $C_{1-30}$-alkylene, $C_{2-30}$-alkenylene, $C_{1-30}$-haloalkylene or a covalent bond,
wherein
$Z^{14}$ and $Z^{15}$ at each occurrence are independently $C_{1-6}$-alkylene, $C_{2-6}$-alkenylene, $C_{1-6}$-haloalkylene or a covalent bond, and
$R^{18}$ at each occurrence is independently H, $C_{1-20}$-alkyl or —$Z^{16}$—$C_{6-14}$-aryl,
wherein
$Z^{16}$ at each occurrence is independently $C_{1-6}$-alkylene, $C_{2-6}$-alkenylene, $C_{1-6}$-haloalkylene or a covalent bond,
$Ar^{10}$ at each occurrence is independently $C_{6-14}$-aryl or monovalent 5 to 14 membered aromatic heterocyclic residue, each optionally substituted with 1 to 5 substituents $R^g$, wherein each $R^g$ is independently selected from the group consisting of halogen, CN, $C_{1-6}$-alkyl, $C_{1-6}$-alkoxy and $C_{1-6}$-haloalkyl,
$Ar^{11}$ and $Ar^{12}$ at each occurrence are independently $C_{6-14}$-arylene or bivalent 5 to 14 membered aromatic heterocyclic residue, each optionally substituted with 1 to 4 substituents $R^h$, wherein each $R^h$ is independently selected from the group consisting of halogen, CN, $C_{1-6}$-alkyl, $C_{1-6}$-alkoxy and $C_{1-6}$-haloalkyl and R$^{17}$ at each occurrence is independently C$_{1-20}$-alkyl, C$_{2-20}$-alkenyl, C$_{1-20}$-haloalkyl or C$_{1-20}$-alkoxy, R$^{19}$ is O or C(CN)$_2$, and R$^{20}$ and R$^{21}$ are the same or different and are R$^{22}$ or CN, wherein R$^{22}$ has the same meaning as R$^1$, G$^1$ and G$^2$ are the same or different and are phenylene or a monocyclic bivalent 5 to 8 membered aromatic heterocyclic residue, which phenylene and monocyclic bivalent 5 to 8 membered aromatic heterocyclic residue are optionally substituted with 1 to 4 substituents R$^i$, wherein each R$^i$ is independently selected from the group consisting of halogen, —CN, —NO$_2$, —OH, C$_{1-30}$-alkyl, C$_{2-30}$-alkenyl, C$_{2-30}$-alkynyl, —Z$^{17}$—O—C$_{1-30}$-alkyl, —Z$^{17}$—S—C$_{1-30}$-alkyl, —Z$^{17}$—C$_{3-10}$-cycloalkyl, —Z$^{17}$—C$_{5-10}$-cycloalkenyl, —Z$^{17}$—C$_{8-10}$-cycloalkynyl, —Z$^{17}$—C$_{6-14}$-aryl, —Z$^{17}$-monovalent 3 to 12 membered aliphatic heterocyclic residue and —Z$^{17}$-monovalent 5 to 14 membered aromatic heterocyclic residue, wherein C$_{1-30}$-alkyl, C$_{2-30}$-alkenyl, C$_{2-30}$-alkynyl, C$_{3-10}$-cycloalkyl, C$_{5-10}$-cycloalkenyl, C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^j$, wherein each R$^j$ is independently selected from the group consisting of halogen, —CN, —NO$_2$, *=O, —OH, —NH$_2$, —NH(C$_{1-20}$-alkyl), —N(C$_{1-20}$-alkyl)$_2$, —N(C$_{1-20}$-alkyl)-C$_{6-14}$-aryl, —N(C$_{6-14}$-aryl)$_2$, —S(O)$_m$H, —S(O)$_m$—C$_{1-20}$-alkyl, —S(O)$_2$OH, —S(O)$_m$—OC$_{1-20}$-alkyl, —S(O)$_m$—OC$_{6-14}$-aryl, —CHO, —C(O)—C$_{1-20}$-alkyl, —C(O)—C$_{6-14}$-aryl, —C(O)OH, —C(O)—OC$_{1-20}$-alkyl, —C(O)—OC$_{6-14}$-aryl, —C(O)NH$_2$, —C(O)NH—C$_{1-20}$-alkyl, —C(O)N(C$_{1-20}$-alkyl)$_2$, —C(O)NH—C$_{6-14}$-aryl, —C(O)N(C$_{1-20}$-alkyl)-C$_{6-14}$-aryl, —C(O)N(C$_{6-14}$-aryl)$_2$, —C(S)NH$_2$, —C(S)NH—C$_{1-20}$-alkyl, —C(S)N(C$_{1-20}$-alkyl)$_2$, —C(S)N(C$_{6-14}$-aryl)$_2$, —C(S)N(C$_{1-20}$-alkyl)-C$_{6-14}$-aryl, —C(S)NH—C$_{6-14}$-aryl, —S(O)$_m$NH$_2$, —S(O)$_m$NH(C$_{1-20}$-alkyl), —S(O)$_m$N(C$_{1-20}$-alkyl)$_2$, —S(O)$_m$NH(C$_{6-14}$-aryl), —S(O)$_m$N(C$_{1-20}$-alkyl)-C$_{6-14}$-aryl, —S(O)$_m$N(C$_{6-14}$-aryl)$_2$, SiH$_3$, SiH(C$_{1-20}$-alkyl)$_2$, SiH$_2$(C$_{1-20}$-alkyl) and Si(C$_{1-20}$-alkyl)$_3$, and wherein C$_{3-10}$-cycloalkyl, C$_{5-10}$-cycloalkenyl, —C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^k$, wherein each R$^k$ is independently selected from the group consisting of C$_{1-20}$-alkyl, C$_{2-20}$-alkenyl, C$_{2-20}$-alkynyl, C$_{1-20}$-alkoxy, —S—C$_{1-20}$-alkyl, C$_{1-20}$-haloalkyl, wherein Z$^{17}$ at each occurrence is independently C$_{1-6}$-alkylene, C$_{2-6}$-alkenylene, C$_{1-6}$-haloalkylene or a covalent bond, and m at each occurrence is independently 0, 1 or 2, L is C$_{6-24}$-arylene or a bivalent 5 to 18 membered aromatic heterocyclic residue, wherein C$_{6-24}$-arylene and bivalent 5 to 18 membered aromatic heterocyclic residue are optionally substituted with 1 to 4 substituents R$^l$, wherein each R$^l$ is independently selected from the group consisting of halogen, —CN, —NO$_2$, *=O, OH, *=C(C$_{1-30}$-alkyl)$_2$, C$_{1-30}$-alkyl, C$_{2-30}$-alkenyl, C$_{2-30}$-alkynyl, —Z$^{18}$—O—C$_{1-30}$-alkyl, —Z$^{18}$—S—C$_{1-30}$-alkyl, —Z$^{18}$—C$_{3-10}$-cycloalkyl, —Z$^{18}$—C$_{5-10}$-cycloalkenyl, —Z$^{18}$—C$_{8-10}$-cycloalkynyl, —Z$^{18}$—C$_{6-14}$-aryl, —Z$^{18}$-monovalent 3 to 12 membered aliphatic heterocyclic residue and —Z$^{18}$-monovalent 5 to 14 membered aromatic heterocyclic residue, wherein C$_{1-30}$-alkyl, C$_{2-30}$-alkenyl, C$_{2-30}$-alkynyl, C$_{3-10}$-cycloalkyl, C$_{5-10}$-cycloalkenyl, C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^m$, wherein each R$^m$ is independently selected from the group consisting of halogen, —CN, —NO$_2$, *=O, —OH, —NH$_2$, —NH(C$_{1-20}$-alkyl), —N(C$_{1-20}$-alkyl)$_2$, —N(C$_{1-20}$-alkyl)-C$_{6-14}$-aryl, —N(C$_{6-14}$-aryl)$_2$, —S(O)$_o$H, —S(O)$_o$—C$_{1-20}$-alkyl, —S(O)$_2$OH, —S(O)$_o$—OC$_{1-20}$-alkyl, —S(O)$_o$—OC$_{6-14}$-aryl, —CHO, —C(O)—C$_{1-20}$-alkyl, —C(O)—C$_{6-14}$-aryl, —C(O)OH, —C(O)—OC$_{1-20}$-alkyl, —C(O)—OC$_{6-14}$-aryl, —C(O)NH$_2$, —C(O)NH—C$_{1-20}$-alkyl, —C(O)N(C$_{1-20}$-alkyl)$_2$, —C(O)NH—C$_{6-14}$-aryl, —C(O)N(C$_{1-20}$-alkyl)-C$_{6-14}$-aryl, —C(O)N(C$_{6-14}$-aryl)$_2$, —C(S)NH$_2$, —C(S)NH—C$_{1-20}$-alkyl, —C(S)N(C$_{1-20}$-alkyl)$_2$, —C(S)N(C$_{6-14}$-aryl)$_2$, —C(S)N(C$_{1-20}$-alkyl)-C$_{6-14}$-aryl, —C(S)NH—C$_{6-14}$-aryl, —S(O)$_o$NH$_2$, —S(O)$_o$NH(C$_{1-20}$-alkyl), —S(O)$_o$N(C$_{1-20}$-alkyl)$_2$, —S(O)$_o$NH(C$_{6-14}$-aryl), —S(O)$_o$N(C$_{1-20}$-alkyl)-C$_{6-14}$-aryl, —S(O)$_o$N(C$_{6-14}$-aryl)$_2$, SiH$_3$, SiH(C$_{1-20}$-alkyl)$_2$, SiH$_2$(C$_{1-20}$-alkyl) and Si(C$_{1-20}$-alkyl)$_3$, and wherein C$_{3-10}$-cycloalkyl, C$_{5-10}$-cycloalkenyl, —C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^n$, wherein each R$^n$ is independently selected from the group consisting of C$_{1-20}$-alkyl, C$_{2-20}$-alkenyl, C$_{2-20}$-alkynyl, C$_{1-20}$-alkoxy, —S—C$_{1-20}$-alkyl, C$_{1-20}$-haloalkyl, wherein Z$^{18}$ at each occurrence is independently C$_{1-6}$-alkylene, C$_{2-6}$-alkenylene, C$_{1-6}$-haloalkylene or a covalent bond, and o at each occurrence is independently 0, 1 or 2, or L is

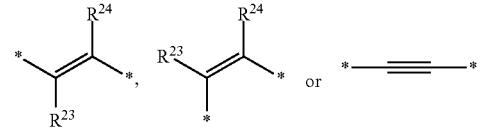

wherein

R$^{23}$ and R$^{24}$ can be the same or different and are H, halogen, —CN, C$_{1-30}$-alkyl, C$_{2-30}$-alkenyl, C$_{2-20}$-alkynyl, C$_{3-10}$-cycloalkyl, C$_{5-10}$-cycloalkenyl, C$_{8-10}$-cycloalkynyl, C$_{1-30}$-haloalkyl, monovalent 3 to 12 membered aliphatic heterocyclic residue, —X$^7$—R$^{25}$, —X$^8$—Ar$^{13}$, —X$^8$—Ar$^{14}$—Ar$^{13}$, —X$^8$—Ar$^{14}$—R$^{26}$ or —X$^8$—Ar$^{14}$—Ar$^{15}$—R$^{26}$, wherein X$^7$ at each occurrence is independently —O—, —[Z$^{19}$—O]$_c$—, —[O—Z$^{19}$]$_c$—O—, —S—, —[Z$^{19}$—S]$_c$—, —[S—Z$^{19}$]$_c$—S—, —S(O), —C(O)—, —C(O)O—, —C(O)NR$^{27}$—, C(O)S—, —O(CO)—, —S(CO)—, —NR$^{27}$C(O)— or —NR$^{27}$—, wherein Z$^{19}$ at each occurrence is independently C$_{1-6}$-alkylene, C$_{2-6}$-alkenylene or C$_{1-6}$-haloalkylene, c at each occurrence is independently an integer from 1 to 10 and R$^{27}$ at each occurrence is independently H, C$_{1-20}$-alkyl, or —Z$^{20}$—C$_{6-14}$-aryl, wherein
- $Z^{28}$ at each occurrence is independently $C_{1-6}$-alkylene, $C_{2-6}$-alkenylene, $C_{1-6}$-haloalkylene or a covalent bond,
- $R^{25}$ at each occurrence is independently $C_{1-30}$-alkyl, $C_{2-30}$-alkenyl or $C_{1-30}$-haloalkyl,
- $X^8$ at each occurrence is independently —$Z^{21}$—O—$Z^{22}$—, —$Z^{21}$—S—$Z^{22}$—, —S(O)—, —C(O)—, —C(O)O—, —(CO)NR$^{28}$—, —C(O)S—, —O(CO)—, —S(CO)—, —NR$^{28}$C(O)—, —NR$^{28}$—, —$Z^{21}$—SiR$^{28}_2$—$Z^{22}$—, $C_{1-30}$-alkylene, $C_{2-30}$-alkenylene, $C_{1-30}$-haloalkylene or a covalent bond,
  wherein
  - $Z^{21}$ and $Z^{22}$ at each occurrence are independently $C_{1-6}$-alkylene, $C_{2-6}$-alkenylene, $C_{1-6}$-haloalkylene or a covalent bond, and
  - $R^{28}$ at each occurrence is independently H, $C_{1-20}$-alkyl, or —$Z^{23}$—$C_{6-14}$-aryl,
    wherein
    - $Z^{23}$ at each occurrence is independently $C_{1-6}$-alkylene, $C_{2-6}$-alkenylene, $C_{1-6}$-haloalkylene or a covalent bond,
- $Ar^{13}$ at each occurrence is independently $C_{6-14}$-aryl or monovalent 5 to 14 membered aromatic heterocyclic residue, each optionally substituted with 1 to 5 substituents $R^o$, wherein each $R^o$ is independently selected from the group consisting of halogen, CN, $C_{1-6}$-alkyl, $C_{1-6}$-alkoxy and $C_{1-6}$-haloalkyl,
- $Ar^{14}$ and $Ar^{15}$ at each occurrence are independently $C_{6-14}$-arylene or bivalent 5 to 14 membered aromatic heterocyclic residue, each optionally substituted with 1 to 4 substituents $R^p$, wherein each $R^p$ is independently selected from the group consisting of halogen, CN, $C_{1-6}$-alkyl, $C_{1-6}$-alkoxy and $C_{1-6}$-haloalkyl, and
- $R^{26}$ at each occurrence is independently $C_{1-20}$-alkyl, $C_{2-20}$-alkenyl, $C_{1-20}$-haloalkyl, $C_{1-20}$-alkoxy, —$X^9$—$Ar^{16}$, —$X^9$—$Ar^{17}$—$Ar^{16}$, —$X^9$—$Ar^{17}$—$R^{29}$, or —$X^9$—$Ar^{17}$—$Ar^{18}$—$R^{29}$,
  wherein
  - $X^9$ at each occurrence is independently —$Z^{24}$—O—$Z^{25}$—, —$Z^{24}$—S—$Z^{25}$, —S(O)—, —O(O)—, —C(O)O—, —(CO)NR$^{30}$—, —C(O)S—, —O(CO)—, —S(CO)—, —NR$^{30}$C(O)—, —NR$^{30}$—, —$Z^{24}$—SiR$^{30}_2$—$Z^{25}$—, $C_{1-30}$-alkylene, $C_{2-30}$-alkenylene, $C_{1-30}$-haloalkylene or a covalent bond,
    wherein
    - $Z^{24}$ and $Z^{25}$ at each occurrence are independently $C_{1-6}$-alkylene, $C_{2-6}$-alkenylene, $C_{1-6}$-haloalkylene or a covalent bond, and
    - $R^{30}$ at each occurrence is independently H, $C_{1-20}$-alkyl or —$Z^{26}$—$C_{6-14}$-aryl,
      wherein
      - $Z^{26}$ at each occurrence is independently $C_{1-6}$-alkylene, $C_{2-6}$-alkenylene, $C_{1-6}$-haloalkylene or a covalent bond,
  - $Ar^{16}$ at each occurrence is independently $C_{6-14}$-aryl or monovalent 5 to 14 membered aromatic heterocyclic residue, each optionally substituted with 1 to 5 substituents $R^q$, wherein each $R^q$ is independently selected from the group consisting of halogen, CN, $C_{1-6}$-alkyl, $C_{1-6}$-alkoxy and $C_{1-6}$-haloalkyl,
  - $Ar^{17}$ and $Ar^{18}$ at each occurrence are independently $C_{6-14}$-arylene or bivalent 5 to 14 membered aromatic heterocyclic residue, each optionally substituted with 1 to 4 substituents $R^r$, wherein each $R^r$ is independently selected from the group consisting of halogen, CN, $C_{1-6}$-alkyl, $C_{1-6}$-alkoxy and $C_{1-6}$-haloalkyl, and
  - $R^{29}$ at each occurrence is independently $C_{1-20}$-alkyl, $C_{2-20}$-alkenyl, $C_{1-20}$-haloalkyl or $C_{1-20}$-alkoxy, q and s are the same or different and are 0, 1, 2, 3, 4 or 5,
r is 0, 1 or 2,
and
n is an integer from 2 to 10'000.

Examples of halogen are —F, —Cl, —Br and —I.

Examples of $C_{1-6}$-alkyl are methyl, ethyl, n-propyl, isopropyl, n-butyl, sec-butyl, isobutyl, tert-butyl, n-pentyl, neopentyl, isopentyl and n-hexyl. Examples of $C_{1-20}$-alkyl are $C_{1-6}$-alkyl, n-heptyl, n-octyl, n-(2-ethyl)hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl are $C_{1-20}$-alkyl, n-docosyl ($C_{22}$), n-tetracosyl ($C_{24}$), n-hexacosyl ($C_{26}$), n-octacosyl ($C_{28}$) and n-triacontyl ($C_{30}$).

Examples of $C_{1-6}$-haloalkyl are $CF_3$, $CHF_2$, $CH_2F$, $C_2F_5$, $CH_2(CH_2)_4CF_3$, $CF_3$, $CCl_3$, $CHCl_2$, $CH_2Cl$, $C_2Cl_5$ and $CH_2(CH_2)_4CCl_3$. Examples of $C_{1-20}$-haloalkyl and of $C_{1-30}$-haloalkyl are $C_{1-6}$-haloalkyl and $CH_2(CH_2)_8CF_3$, $CH_2(CH_2)_{14}CF_3$.

Examples of $C_{1-6}$-alkoxy are methoxy, ethoxy, n-propoxy, isopropoxy, n-butoxy, sec-butoxy, isobutoxy, tert-butoxy, n-pentoxy, neopentoxy, isopentoxy and n-hexoxy. Examples of $C_{1-20}$-alkoxy are $C_{1-6}$-alkoxy, n-heptoxy, n-octoxy, n-nonoxy and n-decoxy, n-undecoxy, n-dodoxy, n-undecoxy, n-dodecoxy, n-tridecoxy, n-tetradecoxy, n-pentadecoxy, n-hexadecoxy, n-heptadecoxy, n-octadecoxy, n-nonadecoxy and n-eicosoxy ($C_{20}$).

Examples of $C_{2-20}$-alkenyl are ethenyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl, docenyl, undocenyl and oleyl ($C_{18}$). Examples of $C_{2-20}$-alkenyl are also butadienyl, pentadienyl, hexadienyl, linoleyl ($C_{18}$), linolenyl ($C_{18}$) and arachidonyl ($C_{20}$). Examples of $C_{2-30}$-alkenyl are $C_{2-20}$-alkenyl and erucyl ($C_{22}$).

Examples of $C_{2-20}$-alkynyl are ethynyl, 2-propynyl, 2-butynyl, 3-butynyl, pentynyl, hexynyl, heptynyl, octynyl, nonynyl, decynyl, undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$). Examples of $C_{2-30}$-alkynyl are $C_{2-20}$-alkynyl.

Examples of $C_{3-10}$-cycloalkyl are preferably monocyclic $C_{3-10}$-cycloalkyls such as cyclopropyl, cyclobutyl, cyclopentyl, cyclohexyl, cycloheptyl and cyclooctyl, but include also polycyclic $C_{3-10}$-cycloalkyls such as decalinyl, norbornyl and adamantyl.

Examples of $C_{5-10}$-cycloalkenyl are preferably monocyclic $C_{5-10}$-cycloalkenyls such as cyclopentenyl, cyclohexenyl, cyclohexadienyl and cycloheptatrienyl, but include also polycyclic $C_{5-10}$-cycloalkenyls.

An example of $C_{8-10}$-cycloalkynyl is cyclooctynyl.

The monovalent 3 to 12 membered aliphatic heterocyclic residues can be monocyclic monovalent 3 to 8 membered aliphatic heterocyclic residues or polycyclic, for example bicyclic, monovalent 7 to 12 membered aliphatic heterocyclic residues.

Examples of monocyclic monovalent 3 to 8 membered aliphatic heterocyclic residues are monocyclic monovalent 5 membered aliphatic heterocyclic residues containing one heteroatom such as pyrrolidinyl, 1-pyrrolinyl, 2-pyrrolinyl, 3-pyrrolinyl, tetrahydrofuryl, 2,3-dihydrofuryl, tetrahydrothiophenyl and 2,3-dihydrothiophenyl, monocyclic monovalent 5 membered aliphatic heterocyclic residues containing two heteroatoms such as imidazolidinyl, imidazolinyl, pyrazolidinyl, pyrazolinyl, oxazolidinyl, oxazolinyl, isoxazolidinyl, isoxazolinyl, thiazolidinyl, thiazolinyl, isothiazolidinyl and isothiazolinyl, monocyclic monovalent 5 membered aliphatic heterocyclic residues containing three heteroatoms such as 1,2,3-triazolyl, 1,2,4-triazolyl and 1,4,2-dithiazolyl, monocyclic monovalent 6 membered aliphatic heterocyclic residues containing one heteroatom such as piperidyl, piperidino, tetrahydropyranyl, pyranyl, thianyl and thiopyranyl, monocyclic monovalent 6 membered aliphatic heterocyclic residues containing two heteroatoms such as piperazinyl, morpholinyl and morpholino and thiazinyl, monocyclic monovalent 7 membered aliphatic heterocyclic residues containing one hereoatom such as azepanyl, azepinyl, oxepanyl, thiepanyl, thiapanyl, thiepinyl, and monocyclic monovalent 7 membered aliphatic heterocyclic residues containing two hereoatom such as 1,2-diazepinyl and 1,3-thiazepinyl.

The monovalent 3 to 12 membered aliphatic heterocyclic residues can contain one or more heteroatoms, which can independently be selected from the group consisting of nitrogen, oxygen, sulfur, phosphor, silicon and arsenic, preferably from the group consisting of nitrogen, oxygen and sulfur.

Examples of monocyclic monovalent 3 to 12 membered aliphatic heterocyclic residue substituted with *=O are 2-oxazolidonyl, 4-piperidonyl, 4-piperidono, pyrimidine-2, 4(1H,3H)-dionyl and 2-pyridonyl.

An example of a bicyclic monovalent 7 to 12 membered aliphatic heterocyclic residue is decahydronaphthyl.

$C_{6-14}$-aryl can be monocyclic or polycyclic. Examples of $C_{6-14}$-aryl are monocyclic $C_6$-aryl such as phenyl, bicyclic $C_{9-10}$-aryl such as 1-naphthyl, 2-naphthyl, indenyl, indanyl and tetrahydronaphthyl, and tricyclic $C_{12-14}$-aryl such as anthryl, phenanthryl, fluorenyl and s-indacenyl.

$C_{6-14}$-haloaryl can be monocyclic or polycyclic. Examples of $C_{6-14}$-haloaryl are 6-chlorophenyl and 2-chlorophenyl.

The monovalent 5 to 14 membered aromatic heterocyclic residues can be monocyclic monovalent 5 to 8 membered aromatic heterocyclic residues, or polycyclic monovalent 7 to 12 membered aromatic heterocyclic residues, for example bicyclic or tricyclic monovalent 9 to 14 membered aromatic heterocyclic residues.

Examples of monocyclic monovalent 5 to 8 membered aromatic heterocyclic residues are monocyclic monovalent 5 membered aromatic heterocyclic residues containing one heteroatom such as pyrrolyl, furyl and thiophenyl, monocyclic monovalent 5 membered aromatic heterocyclic residues containing two heteroatoms such as imidazolyl, pyrazolyl, oxazolyl, isoxazolyl, thiazolyl, isothiazolyl, monocyclic monovalent 5 membered aromatic heterocyclic residues containing three heteroatoms such as 1,2,3-triazolyl, 1,2,4-triazolyl and oxadiazolyl, monocyclic monovalent 5 membered aromatic heterocyclic residues containing four heteroatoms such as tetrazolyl, monocyclic monovalent 6 membered aromatic heterocyclic residues containing one heteroatom such as pyridyl, monocyclic monovalent 6 membered aromatic heterocyclic residues containing two heteroatoms such as pyrazinyl, pyrimidinyl and pyridazinyl, monocyclic monovalent 6 membered aromatic heterocyclic residues containing three heteroatoms such as 1,2,3-triazinyl, 1,2,4-triazinyl and 1,3,5-triazinyl, monocyclic monovalent 7 membered aromatic heterocyclic residues containing one heteroatom such as azepinyl, and monocyclic monovalent 7 membered aromatic heterocyclic residues containing two heteroatoms such as 1,2-diazepinyl, Examples of bicyclic monovalent 7 to 12 membered aromatic heterocyclic residues are bicyclic 9 membered aromatic heterocyclic residues containing one heteroatom such as indolyl, isoindolyl, indolizinyl, indolinyl, benzofuryl, isobenzofuryl, benzothiophenyl and isobenzothiophenyl, bicyclic monovalent 9 membered aromatic heterocyclic residues containing two heteroatoms such as indazolyl, benzimidazolyl, benzimidazolinyl, benzoxazolyl, benzisooxazolyl, benzthiazolyl, benzisothiazolyl, furopyridyl and thienopyridyl, bicyclic monovalent 9 membered aromatic heterocyclic residues containing three heteroatoms such as benzotriazolyl, benzoxadiazolyl, oxazolopyridyl, isooxazolopyridyl, thiazolopyridyl, isothiazolopyridyl and imidazopyridyl, bicyclic monovalent 9 membered aromatic heterocyclic residues containing four heteroatoms such as purinyl, bicyclic monovalent 10 membered aromatic heterocyclic residues containing one heteroatom such as quinolyl, isoquinolyl, chromenyl and chromanyl, bicyclic monovalent 10 membered aromatic heterocyclic residues containing two heteroatoms such as quinoxalinyl, quinazolinyl, cinnolinyl, phthalazinyl, 1,5-naphthyridinyl and 1,8-naphthyridinyl, bicyclic monovalent 10 membered aromatic heterocyclic residues containing three heteroatoms such as pyridopyrazinyl, pyridopyrimidinyl and pyridopyridazinyl, and bicyclic monovalent 10 membered aromatic heterocyclic residues containing four heteroatoms such as pteridinyl.

Examples of tricyclic monovalent 9 to 14 membered aromatic heterocyclic residues are dibenzofuryl, acridinyl, phenoxazinyl, 7H-cyclopenta[1,2-b:3,4-b']dithiophenyl and 4H-cyclopenta[2,1-b:3,4-b']dithiophenyl.

The monovalent 5 to 14 membered aromatic heterocyclic residue can contain one or more heteroatoms which can independently be selected from the group consisting of nitrogen, oxygen, sulfur, phosphor, silicon and arsenic, preferably from the group consisting of nitrogen, oxygen and sulfur.

Examples of $C_{1-6}$-alkylene are methylene, ethylene, butylene, pentylene, hexylene and 2-methylpentylene. Examples of $C_{1-30}$-alkylene are $C_{1-6}$-alkylene, $CH_2(CH_2)_{10}CH_2$ and $CH_2(CH_2)_{20})CH_2$.

Examples of $C_{2-6}$-alkenylene are ethenylene, cis-2-butenylene, trans-butenylene, cis-2-pentenylene, trans-2-pentenylene, trans-2-hexenylene, trans-3-hexenylene and 2-methyl-trans-3-pentenylene. Examples of $C_{2-30}$-alkenylene are $C_{2-6}$-alkenylene, $CH_2(CH_2)_4$—CH=CH—$(CH_2)_4CH_2$ and $CH_2(CH_2)_9$—CH=CH—$(CH_2)_9CH_2$.

Examples of $C_{1-6}$-haloalkylene are $CF_2$, $CCl_2$, $CF_2CF_2$, $CCl_2CCl_2$, $CHFCH_2$, $CHFCH_2CH_2CHF$ and $CHF(CH_2)_4CHF$. Examples of $C_{1-30}$-haloalkylene are $C_{1-6}$-haloalkylene, $CHF(CH_2)_{10}CHF$ and $CHF(CH_2)_{20}CHF$.

Examples of $C_{6-14}$-arylene are monocyclic $C_6$-arylene such as phenylene, bicyclic $C_{9-10}$-arylene such as 1-naphthylene, 2-naphthyl, indenylene, indanylene and tetrahydronaphthylene, and tricyclic $C_{12-14}$-arylene such as anthrylene, phenanthrylene, fluorenylene and s-indacenylene. Examples of $C_{6-24}$-arylene are $C_{6-14}$-arylene and pyrenylene, tetracenylene, perylenylene, indenofluorenylene, pentacenylene, coronenylene and tetraphenylenylene.

The bivalent 5 to 14 membered aromatic heterocyclic residues can be monocyclic bivalent 5 to 8 membered aromatic heterocyclic residues, or polycyclic bivalent 7 to 12 membered aromatic heterocyclic residues, for example bicyclic or tricyclic bivalent 9 to 14 membered aromatic heterocyclic residues.

Examples of monocyclic bivalent 5 to 8 membered aromatic heterocyclic residues are monocyclic bivalent 5 membered aromatic heterocyclic residues containing one heteroatom such as pyrrolylene, furylene and thiophenylene, monocyclic bivalent 5 membered aromatic heterocyclic residues containing two heteroatoms such as imidazolylene, pyrazolylene, oxazolylene, isoxazolylene, thiazolylene, isothiazolylene, monocyclic bivalent 5 membered aromatic heterocyclic residues containing three heteroatoms such as 1,2,3-triazolylene, 1,2,4-triazolylene and oxadiazolylene, monocyclic bivalent 5 membered aromatic heterocyclic residues containing four heteroatoms such as tetrazolylene, monocyclic bivalent 6 membered aromatic heterocyclic residues containing one heteroatom such as pyridylene, monocyclic bivalent 6 membered aromatic heterocyclic residues containing two heteroatoms such as pyrazinylene, pyrimidinylene and pyridazinylene, monocyclic bivalent 6 membered aromatic heterocyclic residues containing three heteroatoms such as 1,2,3-triazinylene, 1,2,4-triazinylene and 1,3,5-triazinylene, monocyclic bivalent 7 membered aromatic heterocyclic residues containing one heteroatom such as azepinylene, and monocyclic bivalent 7 membered aromatic heterocyclic residues containing two heteroatoms such as 1,2-diazepinylene.

Examples of bicyclic bivalent 7 to 12 membered aromatic heterocyclic residues are bicyclic bivalent 9 membered aromatic heterocyclic residues containing one heteroatom such as indolylene, isoindolylene, indolizinylene, indolinylene, benzofurylene, isobenzofurylene, benzothiophenylene and isobenzothiophenylene, bicyclic bivalent 9 membered aromatic heterocyclic residues containing two heteroatoms such as indazolylene, benzimidazolylene, benzimidazolinylene, benzoxazolylene, benzisooxazolylene, benzthiazolylene, benzisothiazolylene, furopyridylene and thienopyridylene, bicyclic bivalent 9 membered aromatic heterocyclic residues containing three heteroatoms such as benzotriazolylene, benzoxadiazolylene, oxazolopyridylene, isooxazolopyridylene, thiazolopyridylene, isothiazolopyridylene and imidazopyridylene, bicyclic bivalent 9 membered aromatic heterocyclic residues containing four heteroatoms such as purinylene, bicyclic bivalent 10 membered aromatic heterocyclic residues containing one heteroatom such as quinolylene, isoquinolylene, chromenylene and chromanylene, bicyclic bivalent 10 membered aromatic heterocyclic residues containing two heteroatoms such as quinoxalinylene, quinazolinylene, cinnolinylene, phthalazinylene, 1,5-naphthyridinylene and 1,8-naphthyridinylene, bicyclic bivalent 10 membered aromatic heterocyclic residues containing three heteroatoms such as pyridopyrazinylene, pyridopyrimidinylene and pyridopyridazinylene, and bicyclic bivalent 10 membered aromatic heterocyclic residues containing four heteroatoms such as pteridinylene.

Examples of tricyclic bivalent 9 to 14 membered aromatic heterocyclic residues containing one heteroatom are dibenzofurylene and acridinylene. Examples of a tricyclic bivalent 9 to 14 membered aromatic heterocyclic residues containing two heteroatoms are phenoxazinylene, 7H-cyclopenta[1,2-b:3,4-b']dithiophenylene and 4H-cyclopenta[2,1-b:3,4-b']dithiophenylene.

Examples of bivalent 5 to 18 membered aromatic heterocyclic residues are bivalent 5 to 14 membered aromatic heterocyclic residues.

The bivalent 5 to 14 membered, respectively, 5 to 18 membered aromatic heterocyclic residue can contain one or more heteroatoms which can independently be selected from the group consisting of nitrogen, oxygen, sulfur, phosphor, silicon and arsenic, preferably from the group consisting of nitrogen, silicon and sulfur.

Preferably, $A^1$ and $A^2$ are S.

Preferably, E is selected from the group consisting of

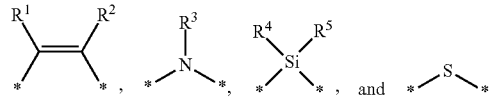

More preferably, E is selected from the group consisting of

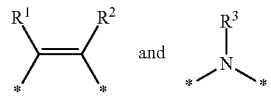

Most preferably, E is

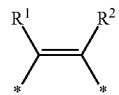

Preferably, $R^1$ and $R^2$ are the same or different and are H, halogen, —CN, $C_{1-30}$-alkyl, $C_{2-30}$-alkenyl, $C_{1-30}$-haloalkyl, —$X^1$—$R^6$, —$X^2$—$Ar^1$, —$X^2$—$Ar^2$—$Ar^1$, —$X^2$—$Ar^2$—$R^7$ or —$X^2$—$Ar^2$—$Ar^3$—$R^7$, wherein $X^1$ at each occurrence is independently —O—, —[$Z^1$—O]$_a$—, —[O—$Z^1$]$_a$—O—, —S—, —[$Z^1$—S—]$_a$—, —[S—$Z^1$]$_a$—S—, —S(O), —C(O)—, —C(O)O—, —C(O)—$NR^8$—, C(O)S—, —O(CO)—, —S(CO)—, —$NR^8$C(O)— or —$NR^8$—, wherein $Z^1$ at each occurrence is independently $C_{1-6}$-alkylene, $C_{2-6}$-alkenylene or $C_{1-6}$-haloalkylene, a at each occurrence is independently an integer from 1 to 10 and $R^8$ at each occurrence is independently H, $C_{1-20}$-alkyl, or —$Z^2$—$C_{6-14}$-aryl, wherein $Z^2$ at each occurrence is independently $C_{1-6}$-alkylene, $C_{2-6}$-alkenylene, $C_{1-6}$-haloalkylene or a covalent bond, $R^6$ at each occurrence is independently $C_{1-30}$-alkyl, $C_{2-30}$-alkenyl or $C_{1-30}$-haloalkyl, $X^2$ at each occurrence is independently —$Z^3$—O—$Z^4$—, —$Z^3$—S—$Z^4$—, —S(O)—, —C(O)—, —C(O)O—, —(CO)$NR^9$, —C(O)S—, —O(CO)—, —S(CO)—, —$NR^9$C(O)—, —$NR^9$—, —$Z^3$—$SiR^9_2$—$Z^4$—, $C_{1-30}$-alkylene, $C_{2-30}$-alkenylene, $C_{1-30}$-haloalkylene or a covalent bond, wherein $Z^3$ and $Z^4$ at each occurrence are independently $C_{1-6}$-alkylene, $C_{2-6}$-alkenylene, $C_{1-6}$-haloalkylene or a covalent bond, and $R^9$ at each occurrence is independently H, $C_{1-20}$-alkyl, or —$Z^5$—$C_{6-14}$-aryl, wherein
  $Z^5$ at each occurrence is independently $C_{1-6}$-alkylene, $C_{2-6}$-alkenylene, $C_{1-6}$-haloalkylene or a covalent bond,
Ar$^1$ at each occurrence is independently $C_{6-14}$-aryl or monovalent 5 to 14 membered aromatic hetrocyclic residue, each optionally substituted with 1 to 5 substituents R$^a$, wherein each R$^a$ is independently selected from the group consisting of halogen, CN, $C_{1-6}$-alkyl, $C_{1-6}$-alkoxy and $C_{1-6}$-haloalkyl,
Ar$^2$ and Ar$^3$ at each occurrence are independently $C_{6-14}$-arylene or bivalent 5 to 14 membered aromatic heterocyclic residue, each optionally substituted with 1 to 4 substituents R$^b$, wherein each R$^b$ is independently selected from the group consisting of halogen, CN, $C_{1-6}$-alkyl, $C_{1-6}$-alkoxy and $C_{1-6}$-haloalkyl, and
R$^7$ at each occurrence is independently $C_{1-20}$-alkyl, $C_{2-20}$-alkenyl, $C_{1-20}$-haloalkyl and $C_{1-20}$-alkoxy.

More preferably, R$^1$ and R$^2$ are the same or different and are H, halogen, —CN, $C_{1-30}$-alkyl, $C_{2-30}$-alkenyl, $C_{1-30}$-haloalkyl, —X$^1$—R$^6$, —X$^2$—Ar$^1$, —X$^2$—Ar$^2$—Ar$^1$, —X$^2$—Ar$^2$—R$^7$ or —X$^2$—Ar$^2$—Ar$^3$—R$^7$,
wherein
  X$^1$ at each occurrence is independently —O—, —[Z$^1$—O]$_a$—, —[O—Z$^1$]$_a$—O—, —S—, —[Z$^1$—S—]$_a$—, or
  wherein
    $Z^1$ at each occurrence is independently $C_{1-6}$-alkylene, $C_{2-6}$-alkenylene or $C_{1-6}$-haloalkylene,
    a at each occurrence is independently an integer from 1 to 10 and
    R$^6$ at each occurrence is independently $C_{1-30}$-alkyl, $C_{2-30}$-alkenyl or $C_{1-30}$-haloalkyl,
  X$^2$ at each occurrence is independently —Z$^3$—O—Z$^4$—, —Z$^3$—S—Z$^4$—, $C_{1-30}$-alkylene, $C_{2-30}$-alkenylene, $C_{1-30}$-haloalkylene or a covalent bond,
  wherein
    $Z^3$ and $Z^4$ at each occurrence are independently $C_{1-6}$-alkylene, $C_{2-6}$-alkenylene, $C_{1-6}$-haloalkylene or a covalent bond, and
  Ar$^1$ at each occurrence is independently $C_{6-14}$-aryl or monovalent 5 to 14 membered aromatic hetrocyclic residue, each optionally substituted with 1 to 5 substituents R$^a$, wherein each R$^a$ is independently selected from the group consisting of halogen, CN, $C_{1-6}$-alkyl, $C_{1-6}$-alkoxy and $C_{1-6}$-haloalkyl,
  Ar$^2$ and Ar$^3$ at each occurrence are independently $C_{6-14}$-arylene or bivalent 5 to 14 membered aromatic heterocyclic residue, each optionally substituted with 1 to 4 substituents R$^b$, wherein each R$^b$ is independently selected from the group consisting of halogen, CN, $C_{1-6}$-alkyl, $C_{1-6}$-alkoxy and $C_{1-6}$-haloalkyl, and
  R$^7$ at each occurrence is independently $C_{1-20}$-alkyl, $C_{2-20}$-alkenyl, $C_{1-20}$-haloalkyl or $C_{1-20}$-alkoxy.

Even more preferably, R$^1$ and R$^2$ are the same or different and are H, $C_{1-30}$-alkyl, $C_{1-30}$-haloalkyl, —X$^1$—R$^6$ or —X$^2$—Ar$^1$,
wherein
  X$^1$ at each occurrence is independently —[Z$^1$—O]$_a$—, —[Z$^1$—S—]$_a$—, or —[S—Z$^1$]$_a$—S—,
  wherein
    $Z^1$ at each occurrence is independently $C_{1-6}$-alkylene or $C_{1-6}$-haloalkylene,
    a at each occurrence is independently an integer from 1 to 10 and
    R$^6$ at each occurrence is independently $C_{1-30}$-alkyl or $C_{1-30}$-haloalkyl, X$^2$ at each occurrence is independently —Z$^3$—O—Z$^4$—, —Z$^3$—S—Z$^4$—, $C_{1-30}$-alkylene or $C_{1-30}$-haloalkylene,
  wherein
    $Z^3$ and $Z^4$ at each occurrence are independently $C_{1-6}$-alkylene or $C_{1-6}$-haloalkylene, and
  Ar$^1$ at each occurrence is independently $C_{6-14}$-aryl, optionally substituted with 1 to 5 substituents R$^a$, wherein each R$^a$ is independently selected from the group consisting of halogen $C_{1-6}$-alkyl and $C_{1-6}$-alkoxy.

Most preferably, R$^1$ and R$^2$ are the same or different and are $C_{1-30}$-alkyl, $C_{1-30}$-haloalkyl or —X$^2$—Ar$^1$,
wherein
  X$^2$ at each occurrence is independently $C_{1-30}$-alkylene or $C_{1-30}$-haloalkylene, and
  Ar$^1$ at each occurrence is independently $C_{6-14}$-aryl, optionally substituted with 1 to 5 substituents R$^a$, wherein each R$^a$ is independently selected from the group consisting of halogen $C_{1-6}$-alkyl and $C_{1-6}$-alkoxy.

In particular, R$^1$ and R$^2$ are the same or different and are $C_{1-30}$-alkyl, for example $C_{1-20}$-alkyl or $C_{1-6}$-alkyl, for example methyl or n-hexyl.

Preferably, R$^3$ is H, halogen, CN, $C_{1-30}$-alkyl, $C_{2-30}$-alkenyl, $C_{1-30}$-haloalkyl, —X$^4$—R$^{12}$, —X$^5$—Ar$^7$, —X$^5$—Ar$^8$—Ar$^7$, —X$^5$—Ar$^8$—R$^{13}$ or —X$^5$—Ar$^8$—Ar$^9$—R$^{13}$,
wherein
  X$^4$ at each occurrence is independently —[Z$^9$—O]$_b$—, —[Z$^9$—S—]$_b$—, —S(O)—, —C(O)—, —C(O)O—, —C(O)NR$^{14}$— or C(O)S—,
  wherein
    $Z^9$ at each occurrence is independently $C_{1-6}$-alkylene, $C_{2-6}$-alkenylene or $C_{1-6}$-haloalkylene,
    b at each occurrence is independently an integer from 1 to 10 and
    R$^{14}$ at each occurrence is independently H, $C_{1-20}$-alkyl, or —Z$^{10}$—$C_{6-14}$-aryl,
    wherein
      $Z^{10}$ at each occurrence is independently $C_{1-6}$-alkylene, $C_{2-6}$-alkenylene, $C_{1-6}$-haloalkylene or a covalent bond,
  R$^{12}$ at each occurrence is independently $C_{1-30}$-alkyl, $C_{2-30}$-alkenyl or $C_{1-30}$-haloalkyl,
  X$^5$ at each occurrence is independently —Z$^{11}$—O—Z$^{12}$—, —Z$^{11}$—S—Z$^{12}$—, —S(O)—, —C(O)—, —C(O)O—, —(CO)NR$^{15}$, —C(O)S—, —Z$^{11}$—SiR$^{15}_2$—Z$^{12}$—, $C_{1-30}$-alkylene, $C_{2-30}$-alkenylene, $C_{1-30}$-haloalkylene or a covalent bond,
  wherein
    $Z^{11}$ at each occurrence is independently $C_{1-6}$-alkylene, $C_{2-6}$-alkenylene or $C_{1-6}$-haloalkylene,
    $Z^{12}$ at each occurrence is independently $C_{1-6}$-alkylene, $C_{2-6}$-alkenylene, $C_{1-6}$-haloalkylene or a covalent bond, and
    R$^{15}$ at each occurrence is independently H, $C_{1-20}$-alkyl, or —Z$^{13}$—$C_{6-14}$-aryl,
    wherein
      $Z^{13}$ at each occurrence is independently $C_{1-6}$-alkylene, $C_{2-6}$-alkenylene, $C_{1-6}$-haloalkylene or a covalent bond,
  Ar$^7$ at each occurrence is independently $C_{6-14}$-aryl or monovalent 5 to 14 membered aromatic heterocyclic residue, each optionally substituted with 1 to 5 substituents R$^e$, wherein each R$^e$ is independently selected from the group consisting of halogen, CN, $C_{1-6}$-alkyl, $C_{1-6}$-alkoxy and $C_{1-6}$-haloalkyl, Ar⁸ and Ar⁹ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl and $R^{13}$ at each occurrence is independently $C_{1-20}$-alkyl, $C_{2-20}$-alkenyl, $C_{1-20}$-haloalkyl or $C_{1-20}$-alkoxy, More preferably, $R^3$ is H, $C_{1-30}$-alkyl, $C_{2-30}$-alkenyl, $C_{1-30}$-haloalkyl, —$X^4$—$R^{12}$, —$X^5$—$Ar^7$, —$X^5$—$Ar^8$—$Ar^7$, —$X^5$—$Ar^8$—$R^{13}$ or —$X^5$—$Ar^8$—$Ar^9$—$R^{13}$, wherein $X^4$ at each occurrence is independently —$[Z^9$—O$]_b$— or —$[Z^9$—S$]_b$—, wherein $Z^9$ at each occurrence is independently $C_{1-6}$-alkylene, $C_{2-6}$-alkenylene or $C_{1-6}$-haloalkylene, and b at each occurrence is independently an integer from 1 to 10 and $R^{12}$ at each occurrence is independently $C_{1-30}$-alkyl, $C_{2-30}$-alkenyl or $C_{1-30}$-haloalkyl, $X^5$ at each occurrence is independently —$Z^{11}$—O—$Z^{12}$—, —$Z^{11}$—S—$Z^{12}$—, $C_{1-30}$-alkylene, $C_{2-30}$-alkenylene, $C_{1-30}$-haloalkylene or a covalent bond, wherein $Z^{11}$ at each occurrence is independently $C_{1-6}$-alkylene, $C_{2-6}$-alkenylene or $C_{1-6}$-haloalkylene, and $Z^{12}$ at each occurrence is independently $C_{1-6}$-alkylene, $C_{2-6}$-alkenylene, $C_{1-6}$-haloalkylene or a covalent bond, and $Ar^7$ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl, $Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl, and $R^{13}$ at each occurrence is independently $C_{1-20}$-alkyl, $C_{2-20}$-alkenyl, $C_{1-20}$-haloalkyl or $C_{1-20}$-alkoxy.

Most preferably, $R^3$ is —$X^5$—$Ar^7$, —$X^5$—$Ar^8$—$Ar^7$, —$X^5$—$Ar^8$—$R^{13}$ or —$X^5$—$Ar^8$—$Ar^9$—$R^{13}$, wherein $X^5$ at each occurrence is a covalent bond, $Ar^7$ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl, $Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl, and $R^{13}$ at each occurrence is independently $C_{1-20}$-alkyl, $C_{2-20}$-alkenyl, $C_{1-20}$-haloalkyl or $C_{1-20}$-alkoxy.

In particular, $R^3$ is —$X^5$—$Ar^8$—$R^{13}$, wherein $X^5$ is a covalent bond, $Ar^8$ is $C_{6-14}$-arylene, for example phenylene, and $R^{13}$ is $C_{1-20}$-alkyl.

For example $R^3$ is

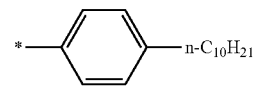

Preferably, $G^1$ and $G^2$ are the same or different and are phenylene, such as

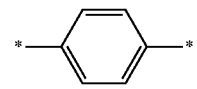 [SMILES: *c1ccc(*)cc1]

or, preferably, a monocyclic bivalent 5 to 8 membered aromatic heterocyclic residue selected from the group consisting of

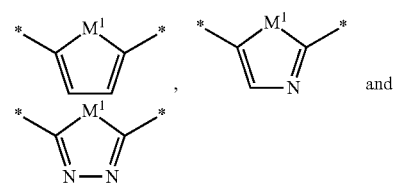

wherein $M^1$ is S, O, NH or $SiR^sR^s$, preferably $M^1$ is S or NH, more preferably $M^1$ is S, wherein $R^s$ is hydrogen or $C_{1-30}$-alkyl, which phenylene or monocyclic bivalent 5 to 8 membered aromatic heterocyclic residue are optionally substituted with 1 to 2 substituents $R^i$, wherein each $R^i$ is independently selected from the group consisting of —CN, $C_{1-30}$-alkyl, —$Z^{17}$—O—$C_{1-30}$-alkyl, —$Z^{17}$—S—$C_{1-30}$-alkyl, —$Z^{17}$—$C_{3-10}$-cycloalkyl, —$Z^{17}$—$C_{6-14}$-aryl, —$Z^{17}$-monovalent 3 to 12 membered aliphatic heterocyclic residue and —$Z^{17}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN, *=O, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_m$—$C_{1-20}$-alkyl, —S(O)$_m$—OC$_{1-20}$-alkyl, —S(O)$_m$—OC$_{6-14}$-aryl, —CHO, —C(O)—$C_{1-20}$-alkyl, —C(O)—$C_{6-14}$-aryl, —C(O)—OC$_{1-20}$-alkyl, —C(O)—OC$_{6-14}$-aryl, —C(O)NH$_2$, —C(O)NH—$C_{1-20}$-alkyl, —C(O)N($C_{1-20}$-alkyl)$_2$, —C(O)NH—$C_{6-14}$-aryl, —C(O)N($C_{1-20}$-alkyl)-$C_{6-14}$-aryl, —C(O)N($C_{6-14}$-aryl)$_2$, —C(S)NH$_2$, —C(S)NH—$C_{1-20}$-alkyl, —C(S)N($C_{1-20}$-alkyl)$_2$, —C(S)N($C_{6-14}$-aryl)$_2$, —C(S)N($C_{1-20}$-alkyl)-$C_{6-14}$-aryl, —C(S)NH—$C_{6-14}$-aryl, —S(O)$_m$NH$_2$, —S(O)$_m$NH($C_{1-20}$-alkyl), —S(O)$_m$N($C_{1-20}$-alkyl)$_2$, —S(O)$_m$NH($C_{6-14}$-aryl), —S(O)$_m$N($C_{1-20}$-alkyl)-$C_{6-14}$-aryl, —S(O)$_m$N($C_{6-14}$-aryl)$_2$ and Si($C_{1-20}$-alkyl)$_3$, and wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, $C_{1-20}$-haloalkyl, wherein $Z^{17}$ at each occurrence is independently $C_{1-6}$-alkylene, $C_{1-6}$-haloalkylene or a covalent bond, and m at each occurrence is independently 0, 1 or 2.

Preferably, each $R^i$ is independently selected from the group consisting of $C_{1-30}$-alkyl, $-Z^{17}-O-C_{1-30}$-alkyl, $-Z^{17}-S-C_{1-30}$-alkyl, $-Z^{17}-C_{3-10}$-cycloalkyl, $-Z^{17}-C_{6-14}$-aryl, $-Z^{17}$-monovalent 3 to 12 membered aliphatic heterocyclic residue and $-Z^{17}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN and *=O, and wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, $C_{1-20}$-haloalkyl, wherein $Z^{17}$ at each occurrence is independently $C_{1-6}$-alkylene, $C_{1-6}$-haloalkylene or a covalent bond.

More preferably, each $R^i$ is independently selected from the group consisting of $C_{1-30}$-alkyl and $-Z^{17}-C_{6-14}$-aryl, wherein $C_{1-30}$-alkyl and $C_{6-14}$-aryl are optionally substituted with 1 to 4 substituents $R^j$, wherein each $R^j$ is independently selected from the group consisting of halogen, —CN and *=O, wherein $Z^{17}$ at each occurrence is a covalent bond and $C_{6-14}$-aryl is optionally substituted with 1 to 4 substituents $R^k$, wherein each $R^k$ is independently selected from the group consisting of $C_{1-20}$-alkyl and $C_{1-20}$-alkoxy.

Most preferably, each $R^i$ is independently $C_{1-30}$-alkyl, preferably n-octyl, n-(2-ethyl)hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$), more preferably, n-dodecyl.

More preferably, $G^1$ and $G^2$ are the same or different and are phenylene, such as

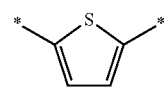 [SMILES: *c1ccc(*)s1]

or, preferably, a monocyclic bivalent 5 to 8 membered aromatic heterocyclic residue selected from the group consisting of

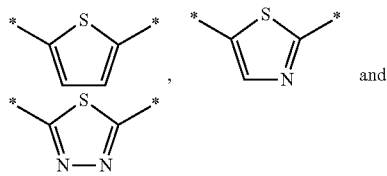

and which phenylene or monocyclic bivalent 5 to 8 membered aromatic heterocyclic residue are optionally substituted with 1 to 2 substituents $R^i$, wherein each $R^i$ is independently selected from the group consisting of $C_{1-30}$-alkyl, $-Z^{17}-O-C_{1-30}$-alkyl, $-Z^{17}-S-C_{1-30}$-alkyl, $-Z^{17}-C_{3-10}$-cycloalkyl, $-Z^{17}-C_{6-14}$-aryl, $-Z^{17}$-monovalent 3 to 12 membered aliphatic heterocyclic residue and $-Z^{17}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN and *=O, and wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, $C_{1-20}$-haloalkyl, wherein $Z^{17}$ at each occurrence is independently $C_{1-6}$-alkylene, $C_{1-6}$-haloalkylene or a covalent bond.

Most preferably, $G^1$ and $G^2$ are the same or different and are a monocyclic bivalent 5 to 8 membered aromatic heterocyclic residue which monocyclic bivalent 5 to 8 membered aromatic heterocyclic residue is

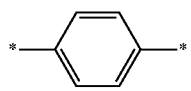

which monocyclic bivalent 5 to 8 membered aromatic heterocyclic residue is substituted with 1 to 2 substituents $R^i$, wherein each $R^i$ is independently selected from the group consisting of $C_{1-30}$-alkyl and $-Z^{17}-C_{6-14}$-aryl, wherein $C_{1-30}$-alkyl and $C_{6-14}$-aryl are optionally substituted with 1 to 4 substituents $R^j$, wherein each $R^j$ is independently selected from the group consisting of halogen, —CN and *=O, and wherein $C_{6-14}$-aryl is optionally substituted with 1 to 4 substituents $R^k$, wherein each $R^k$ is independently selected from the group consisting of $C_{1-20}$-alkyl and $C_{1-20}$-alkoxy, wherein $Z^{17}$ at each occurrence is a covalent bond.

In particular, $G^1$ and $G^2$ are the same or different and are a monocyclic bivalent 5 to 8 membered aromatic heterocyclic residue which monocyclic bivalent 5 to 8 membered aromatic heterocyclic residue is

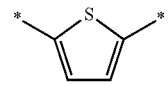 [SMILES: *c1ccc(*)s1]

which monocyclic bivalent 5 to 8 membered aromatic heterocyclic residue is substituted with 1 substituents $R^i$, wherein $R^i$ is $C_{1-30}$-alkyl, preferably n-octyl, n-(2-ethyl)hexyl, n-nonyl, n-decyl, n-undecyl, n-dodecyl, n-undecyl, n-dodecyl, n-tridecyl, n-tetradecyl, n pentadecyl, n-hexadecyl, n-heptadecyl, n-octadecyl, n-nonadecyl and n-icosyl ($C_{20}$), more preferably, n-dodecyl.

Preferably, L is $C_{6-24}$-arylene or a bivalent 5 to 18 membered aromatic heterocyclic residue, wherein $C_{6-24}$- arylene and bivalent 5 to 18 membered aromatic heterocyclic residue are optionally substituted with 1 to 4 substituents $R^l$, wherein each $R^l$ is independently selected from the group consisting of —CN, $C_{1-30}$-alkyl, —$Z^{18}$—O—$C_{1-30}$-alkyl, —$Z^{18}$—S—$C_{1-30}$-alkyl, —$Z^{18}$—$C_{3-10}$-cycloalkyl, —$Z^{18}$—$C_{6-14}$-aryl, —$Z^{18}$-monovalent 3 to 12 membered aliphatic heterocyclic residue and —$Z^{18}$-monovalent 5 to 14 membered aromatic heterocyclic residue, wherein $C_{1-30}$-alkyl, $C_{3-30}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN, *=O, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_o$—$C_{1-20}$-alkyl, —S(O)$_o$—OC$_{1-20}$-alkyl, —S(O)$_o$—OC$_{6-14}$-aryl, —CHO, —C(O)—$C_{1-20}$-alkyl, —C(O)—$C_{6-14}$-aryl, —C(O)—OC$_{1-20}$-alkyl, —C(O)—OC$_{6-14}$-aryl, —C(O)NH$_2$, —C(O)NH—$C_{1-20}$-alkyl, —C(O)N($C_{1-20}$-alkyl)$_2$, —C(O)NH—$C_{6-14}$-aryl, —C(O)N($C_{1-20}$-alkyl)-$C_{6-14}$-aryl, —C(O)N($C_{6-14}$-aryl)$_2$, —C(S)NH$_2$, —C(S)NH—$C_{1-20}$-alkyl, —C(S)N($C_{1-20}$-alkyl)$_2$, —C(S)N($C_{6-14}$-aryl)$_2$, —C(S)N($C_{1-20}$-alkyl)-$C_{6-14}$-aryl, —C(S)NH—$C_{6-14}$-aryl, —S(O)$_o$NH$_2$, —S(O)$_o$NH($C_{1-20}$-alkyl), —S(O)$_o$N($C_{1-20}$-alkyl)$_2$, —S(O)$_o$NH($C_{6-14}$-aryl), —S(O)$_o$N($C_{1-20}$-alkyl)-$C_{6-14}$-aryl, —S(O)$_o$N($C_{6-14}$-aryl)$_2$ and Si($C_{1-20}$-alkyl)$_3$, and wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, —S—$C_{1-20}$-alkyl, $C_{1-20}$-haloalkyl, wherein
$Z^{18}$ at each occurrence is independently $C_{1-6}$-alkylene, $C_{1-6}$-haloalkylene or a covalent bond, and
o at each occurrence is independently 0, 1 or 2,
or
L is

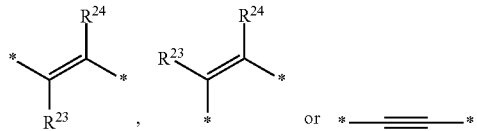

wherein
$R^{23}$ and $R^{24}$ are the same or different and are H, halogen, —CN, $C_{1-30}$-alkyl, $C_{2-30}$-alkenyl, $C_{1-30}$-haloalkyl, —$X^7$—$R^{25}$, —$X^8$—$Ar^{13}$, —$X^8$—$Ar^{14}$—$Ar^{13}$, —$X^8$—$Ar^{14}$—$R^{26}$ or —$X^8$—$Ar^{14}$—$Ar^{15}$—$R^{26}$,
wherein
$X^7$ at each occurrence is independently —O—, —[$Z^{19}$—O]$_o$—, —[O—$Z^{19}$]$_o$—O—, —S—, —[$Z^{19}$—S—]$_o$—, —[S—$Z^{19}$]$_o$—S—, —S(O), —C(O)—, —C(O)O—, —C(O)NR$^{27}$—, C(O)S—, —O(CO)—, —S(CO)—, —NR$^{27}$C(O)— or —NR$^{27}$—,
wherein
$Z^{19}$ at each occurrence is independently $C_{1-6}$-alkylene, $C_{2-6}$-alkenylene or $C_{1-6}$-haloalkylene,
c at each occurrence is independently an integer from 1 to 10 and $R^{27}$ at each occurrence is independently H, $C_{1-20}$-alkyl, or —$Z^{20}$—$C_{6-14}$-aryl,
wherein
$Z^{20}$ at each occurrence is independently $C_{1-6}$-alkylene, $C_{2-6}$-alkenylene, $C_{1-6}$-haloalkylene or a covalent bond,
$R^{25}$ at each occurrence is independently $C_{1-30}$-alkyl, $C_{2-30}$-alkenyl or $C_{1-30}$-haloalkyl,
$X^8$ at each occurrence is independently —$Z^{21}$—O—$Z^{22}$—, —$Z^{21}$—S—$Z^{22}$—, —S(O)—, —C(O)—, —C(O)O—, —(CO)NR$^{28}$, —C(O)S—, —O(CO)—, —S(CO)—, —NR$^{28}$C(O)—, —NR$^{28}$—, —$Z^{21}$—SiR$^{28}_2$—$Z^{22}$—, $C_{1-30}$-alkylene, $C_{2-30}$-alkenylene, $C_{1-30}$-haloalkylene or a covalent bond,
wherein
$Z^{21}$ and $Z^{22}$ at each occurrence are independently $C_{1-6}$-alkylene, $C_{2-6}$-alkenylene, $C_{1-6}$-haloalkylene or a covalent bond, and
$R^{28}$ at each occurrence is independently H, $C_{1-20}$-alkyl, or —$Z^{23}$—$C_{6-14}$-aryl,
wherein
$Z^{23}$ at each occurrence is independently $C_{1-6}$-alkylene, $C_{2-6}$-alkenylene, $C_{1-6}$-haloalkylene or a covalent bond,
$Ar^{14}$ at each occurrence is independently $C_{6-14}$-aryl or monovalent 5 to 14 membered aromatic hetrocyclic residue, each optionally substituted with 1 to 5 substituents $R^o$, wherein each $R^o$ is independently selected from the group consisting of halogen, CN, $C_{1-6}$-alkyl, $C_{1-6}$-alkoxy and $C_{1-6}$-haloalkyl,
$Ar^{14}$ and $Ar^{15}$ at each occurrence are independently $C_{6-14}$-arylene or bivalent 5 to 14 membered aromatic heterocyclic residue, each optionally substituted with 1 to 4 substituents $R^p$, wherein each $R^p$ is independently selected from the group consisting of halogen, CN, $C_{1-6}$-alkyl, $C_{1-6}$-alkoxy and $C_{1-6}$-haloalkyl, and
$R^{26}$ at each occurrence is independently $C_{1-20}$-alkyl, $C_{2-20}$-alkenyl, $C_{1-20}$-haloalkyl and $C_{1-20}$-alkoxy.

Preferably, each $R^l$ is independently selected from the group consisting of $C_{1-30}$-alkyl, —$Z^{18}$—O—$C_{1-30}$-alkyl, —$Z^{18}$—S—$C_{1-30}$-alkyl, —$Z^{18}$—$C_{3-10}$-cycloalkyl, —$Z^{18}$—$C_{6-14}$-aryl, —$Z^{18}$-monovalent 3 to 12 membered aliphatic heterocyclic residue and —$Z^{18}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN and *=O, and wherein $C_{3-30}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^n$, wherein each $R^n$ is independently selected from the group consisting of $C_{1-20}$-alkyl, $C_{1-20}$-alkoxy, $C_{1-20}$-haloalkyl,
wherein
$Z^{16}$ at each occurrence is independently $C_{1-6}$-alkylene, $C_{1-6}$-haloalkylene or a covalent bond.

More preferably, each $R^l$ is independently selected from the group consisting of $C_{1-30}$-alkyl and —$Z^{18}$—$C_{6-14}$-aryl, wherein $C_{1-30}$-alkyl and $C_{6-14}$-aryl are optionally substituted with 1 to 4 substituents $R^m$, wherein each $R^m$ is independently selected from the group consisting of halogen, —CN and *=O, and wherein $C_{6-14}$-aryl is optionally substituted with 1 to 4 substituents $R''$, wherein each $R''$ is independently selected from the group consisting of $C_{1-20}$-alkyl and $C_{1-20}$-alkoxy,
wherein
$Z^{18}$ at each occurrence is a covalent bond.

Most preferably, each $R^1$ is independently $C_{1-30}$-alkyl, preferably n-octyl, n-(2-ethyl)hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$), more preferably, n-hexadecyl.

Preferably, $R^{23}$ and $R^{24}$ are the same or different and are H, halogen, —CN, $C_{1-30}$-alkyl, $C_{2-30}$-alkenyl, $C_{1-30}$-haloalkyl, —$X^7$—$R^{25}$, —$X^8$—$Ar^{13}$, —$X^8$—$Ar^{14}$—$Ar^{13}$, —$X^8$—$Ar^{14}$—$R^{26}$ or —$X^8$—$Ar^{14}$—$Ar^{15}$—$R^{26}$,
wherein
$X^7$ at each occurrence is independently —O—, —[$Z^{19}$—O]$_c$—, —[O—$Z^{19}$]$_c$—O—, —S—, —[$Z^{19}$—S—]$_c$—, or —[S—$Z^{19}$]$_c$—S—,
wherein
$Z^{19}$ at each occurrence is independently $C_{1-6}$-alkylene, $C_{2-6}$-alkenylene or $C_{1-6}$-haloalkylene,
c at each occurrence is independently an integer from 1 to 10 and
$R^{25}$ at each occurrence is independently $C_{1-30}$-alkyl, $C_{2-30}$-alkenyl or $C_{1-30}$-haloalkyl,
$X^8$ at each occurrence is independently —$Z^{21}$—O—$Z^{22}$—, —$Z^{21}$—S—$Z^{22}$—, $C_{1-30}$-alkylene, $C_{2-30}$-alkenylene, $C_{1-30}$-haloalkylene or a covalent bond,
wherein
$Z^{21}$ and $Z^{22}$ at each occurrence are independently $C_{1-6}$-alkylene, $C_{2-6}$-alkenylene, $C_{1-6}$-haloalkylene or a covalent bond, and
$Ar^{13}$ at each occurrence is independently $C_{6-14}$-aryl or monovalent 5 to 14 membered aromatic hetrocyclic residue, each optionally substituted with 1 to 5 substituents $R^o$, wherein each $R^o$ is independently selected from the group consisting of halogen, CN, $C_{1-6}$-alkyl, $C_{1-6}$-alkoxy and $C_{1-6}$-haloalkyl,
$Ar^{14}$ and $Ar^{15}$ at each occurrence are independently $C_{6-14}$-arylene or bivalent 5 to 14 membered aromatic heterocyclic residue, each optionally substituted with 1 to 4 substituents $R^p$, wherein each $R^p$ is independently selected from the group consisting of halogen, CN, $C_{1-6}$-alkyl, $C_{1-6}$-alkoxy and $C_{1-6}$-haloalkyl, and
$R^{26}$ at each occurrence is independently $C_{1-20}$-alkyl, $C_{2-20}$-alkenyl, $C_{1-20}$-haloalkyl or $C_{1-20}$-alkoxy.

More preferably, $R^{23}$ and $R^{24}$ are the same or different and are H, $C_{1-30}$-alkyl, $C_{1-30}$-haloalkyl, —$X^7$—$R^{25}$ or —$X^8$—$Ar^{13}$,
wherein
$X^7$ at each occurrence is independently —[$Z^{19}$—O]$_c$—, —[$Z^{19}$—S—]$_c$—, or —[S—$Z^{19}$]$_c$—S—,
wherein
$Z^{19}$ at each occurrence is independently $C_{1-6}$-alkylene or $C_{1-6}$-haloalkylene,
c at each occurrence is independently an integer from 1 to 10 and
$R^{25}$ at each occurrence is independently $C_{1-30}$-alkyl or $C_{1-30}$-haloalkyl,
$X^8$ at each occurrence is independently —$Z^{21}$—O—$Z^{22}$—, —$Z^{21}$—S—$Z^{22}$—, $C_{1-30}$-alkylene or $C_{1-30}$-haloalkylene,
wherein
$Z^{21}$ and $Z^{22}$ at each occurrence are independently $C_{1-6}$-alkylene or $C_{1-6}$-haloalkylene, and $Ar^{13}$ at each occurrence is independently $C_{6-14}$-aryl, optionally substituted with 1 to 5 substituents $R^o$, wherein each $R^o$ is independently selected from the group consisting of halogen $C_{1-6}$-alkyl and $C_{1-6}$-alkoxy.

Most preferably, $R^{23}$ and $R^{24}$ are the same or different and are H, $C_{1-30}$-alkyl or $C_{1-30}$-haloalkyl, in particular H.

More preferably, L is a bivalent 5 to 18 membered aromatic heterocyclic residue, wherein the bivalent 5 to 18 membered aromatic heterocyclic residue is optionally substituted with 1 to 4 substituents $R^l$, wherein each $R^l$ is independently selected from the group consisting of $C_{1-30}$-alkyl, —$Z^{18}$—O—$C_{1-30}$-alkyl, —$Z^{18}$—S—$C_{1-30}$-alkyl, —$Z^{18}$—$C_{3-10}$-cycloalkyl, —$Z^{18}$—$C_{6-14}$-aryl, —$Z^{18}$-monovalent 3 to 12 membered aliphatic heterocyclic residue and —$Z^{18}$-monovalent 5 to 14 membered aromatic heterocyclic residue,
wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN and *=O, and
wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R''$, wherein each $R''$ is independently selected from the group consisting of $C_{1-20}$-alkyl, $C_{1-20}$-alkoxy, $C_{1-20}$-haloalkyl,
wherein
$Z^{18}$ at each occurrence is independently $C_{1-6}$-alkylene, $C_{1-6}$-haloalkylene or a covalent bond,
or
L is

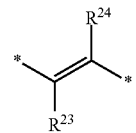

wherein
$R^{23}$ and $R^{24}$ are the same or different and are H, halogen, —CN, $C_{1-30}$-alkyl, $C_{2-30}$-alkenyl, $C_{1-30}$-haloalkyl, —$X^7$—$R^{25}$, —$X^8$—$Ar^{13}$, —$X^8$—$Ar^{14}$—$Ar^{13}$, —$X^8$—$Ar^{14}$—$R^{26}$ or —$X^8$—$Ar^{14}$—$Ar^{15}$—$R^{26}$,
wherein
$X^7$ at each occurrence is independently —O—, —[$Z^{19}$—O]$_c$—, —[O—$Z^{19}$]$_c$—O—, —S—, —[$Z^{19}$—S—]$_c$—, or —[S—$Z^{19}$]$_c$—S—,
wherein
$Z^{19}$ at each occurrence is independently $C_{1-6}$-alkylene, $C_{2-6}$-alkenylene or $C_{1-6}$-haloalkylene,
c at each occurrence is independently an integer from 1 to 10 and
$R^{25}$ at each occurrence is independently $C_{1-30}$-alkyl, $C_{2-30}$-alkenyl or $C_{1-30}$-haloalkyl,
$X^8$ at each occurrence is independently —$Z^{21}$—O—$Z^{22}$—, —$Z^{21}$—S—$Z^{22}$—, $C_{1-30}$-alkylene, $C_{2-30}$-alkenylene, $C_{1-30}$-haloalkylene or a covalent bond,
wherein
$Z^{21}$ and $Z^{22}$ at each occurrence are independently $C_{1-6}$-alkylene, $C_{2-6}$-alkenylene, $C_{1-6}$-haloalkylene or a covalent bond, and Ar¹³ at each occurrence is independently $C_{6-14}$-aryl or monovalent 5 to 14 membered aromatic hetrocyclic residue, each optionally substituted with 1 to 5 substituents $R^o$, wherein each $R^o$ is independently selected from the group consisting of halogen, CN, $C_{1-6}$-alkyl, $C_{1-6}$-alkoxy and $C_{1-6}$-haloalkyl, Ar¹⁴ and Ar¹⁵ at each occurrence are independently $C_{6-14}$-arylene or bivalent 5 to 14 membered aromatic heterocyclic residue, each optionally substituted with 1 to 4 substituents $R^p$, wherein each $R^p$ is independently selected from the group consisting of halogen, CN, $C_{1-6}$-alkyl, $C_{1-6}$-alkoxy and $C_{1-6}$-haloalkyl, and R²⁶ at each occurrence is independently $C_{1-20}$-alkyl, $C_{2-20}$-alkenyl, $C_{1-20}$-haloalkyl or $C_{1-20}$-alkoxy.

Even more preferably, L is a bivalent 5 to 18 membered aromatic heterocyclic residue selected from the group consisting of

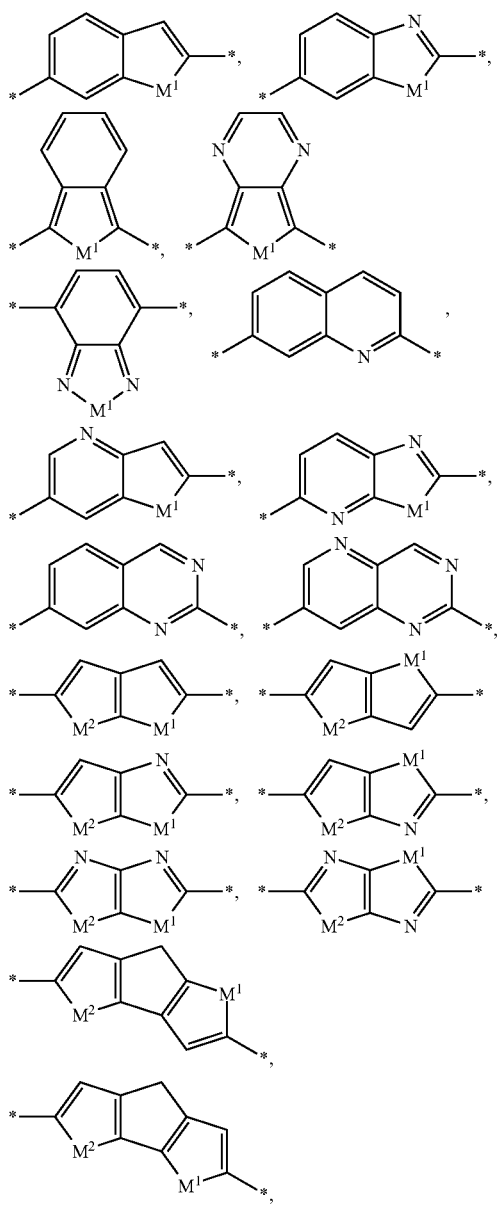

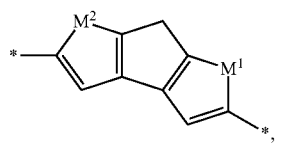
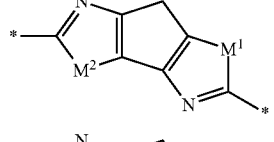
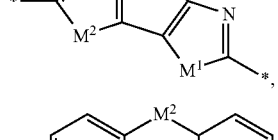
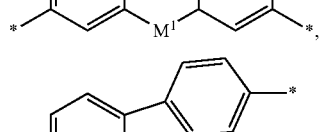
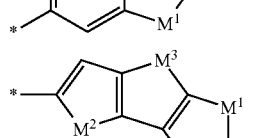
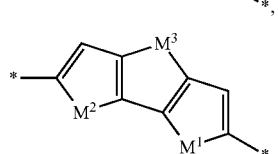
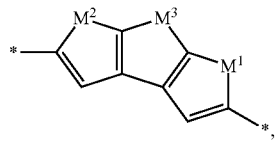
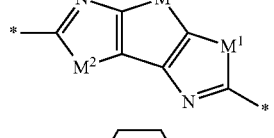
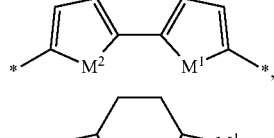
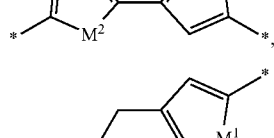

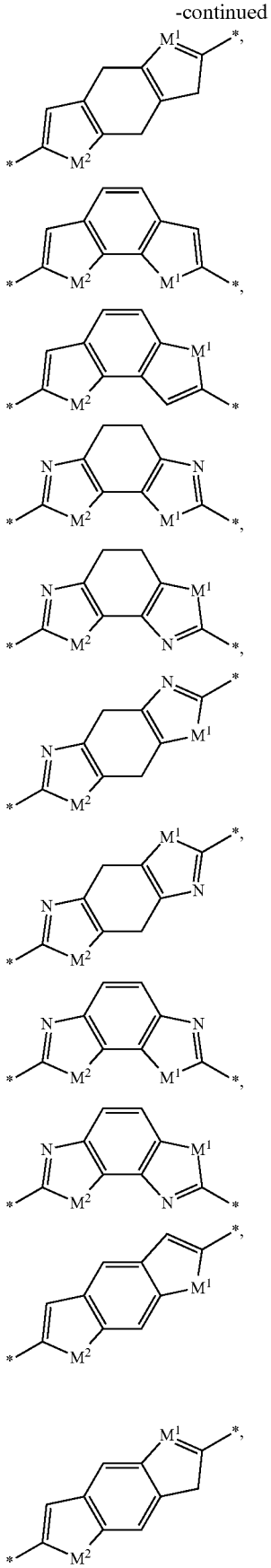

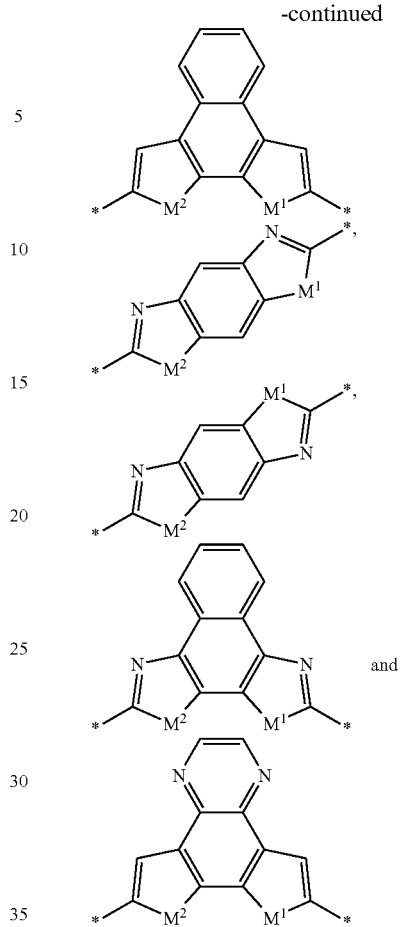

wherein the bivalent 5 to 18 membered aromatic heterocyclic residue is optionally substituted with 1 to 4 substituents $R^l$, wherein each $R^l$ $R^l$ is independently selected from the group consisting of $C_{1-30}$-alkyl and $-Z^{18}-C_{6-14}$-aryl, wherein $C_{1-30}$-alkyl and $C_{6-14}$-aryl are optionally substituted with 1 to 4 substituents $R^m$, wherein each $R^m$ is independently selected from the group consisting of halogen, $-CN$ and $*=O$, and wherein $C_{6-14}$-aryl is optionally substituted with 1 to 4 substituents $R^n$, wherein each $R^n$ is independently selected from the group consisting of $C_{1-20}$-alkyl and $C_{1-20}$-alkoxy, wherein $Z^{18}$ at each occurrence is a covalent bond, wherein, $M^1$, $M^2$ and $M^3$ can be the same or different and are S, O, NH or $SiR'R^t$, preferably $M^1$, $M^2$ are S or NH, and $M^3$ is S, O, NH or $SiR'R^t$, more preferably $M^1$ and $M^2$ are S, and $M^3$ is NH or $SiR'R^t$, wherein $R^t$ is H or $C_{1-30}$-alkyl, or L is

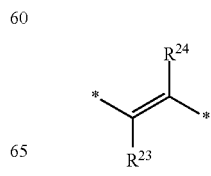

wherein
R²³ and R²⁴ are the same or different and are H, $C_{1-30}$-alkyl, $C_{1-30}$-haloalkyl, —X⁷—R²⁵ or —X⁸—Ar¹³,
wherein
X⁷ at each occurrence is independently —[$Z^{19}$—O]$_c$—, —[$Z^{19}$—S]$_c$—, or —[S—$Z^{19}$]$_c$—S—,
wherein
Z¹⁹ at each occurrence is independently $C_{1-6}$-alkylene or $C_{1-6}$-haloalkylene,
c at each occurrence is independently an integer from 1 to 10 and
R²⁵ at each occurrence is independently $C_{1-30}$-alkyl or $C_{1-30}$-haloalkyl,
X⁸ at each occurrence is independently —Z²¹—O—Z²²—, —Z²¹—S—Z²²—, $C_{1-30}$-alkylene or $C_{1-30}$-haloalkylene,
wherein
Z²¹ and Z²² at each occurrence are independently $C_{1-6}$-alkylene or $C_{1-6}$-haloalkylene, and
Ar¹³ at each occurrence is independently $C_{6-14}$-aryl, optionally substituted with 1 to 5 substituents R°, wherein each R° is independently selected from the group consisting of halogen $C_{1-6}$-alkyl and $C_{1-6}$-alkoxy.

Even more preferably,
L is a bivalent 5 to 18 membered aromatic heterocyclic residue selected from the group consisting of

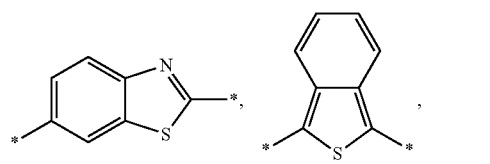

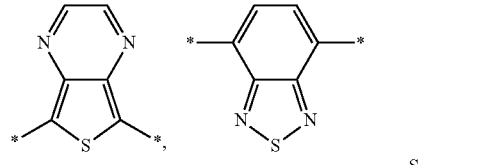

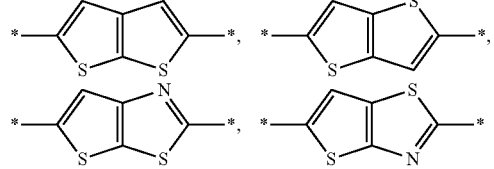

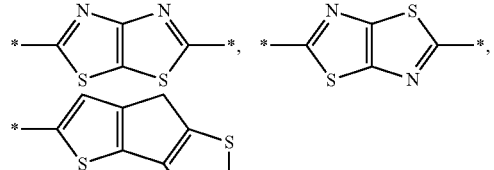

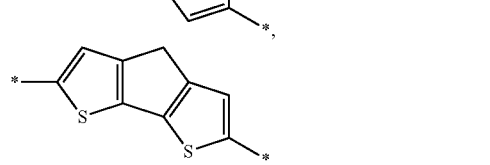

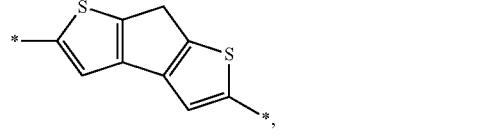

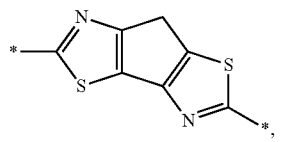

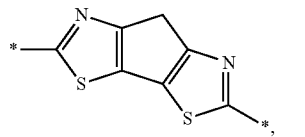

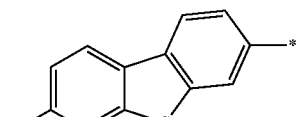

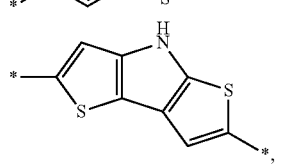

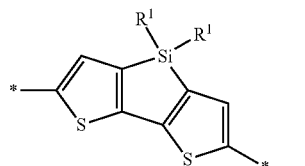

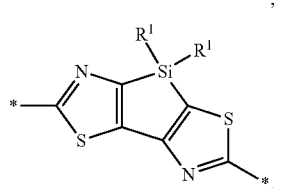

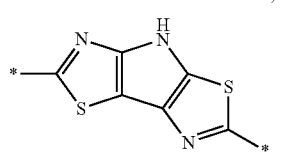

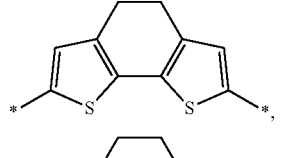

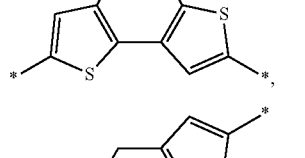

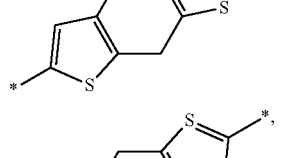

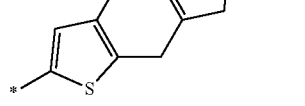

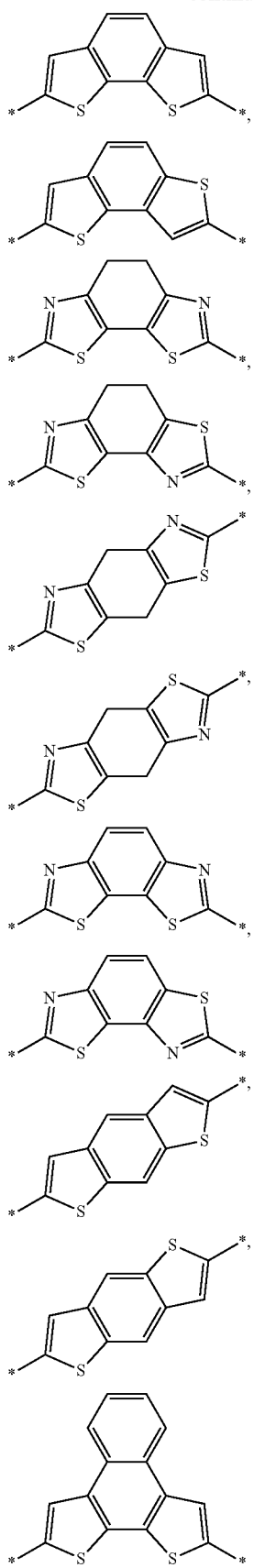

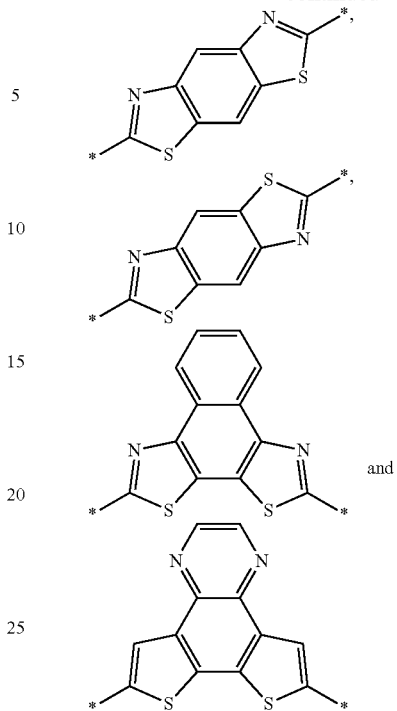

and

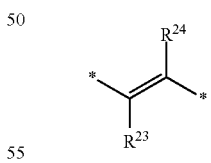

wherein the bivalent 5 to 18 membered aromatic heterocyclic residue is optionally substituted with 1 to 4 substituents $R^l$, wherein each wherein each $R^l R^l$ is independently selected from the group consisting of $C_{1-30}$-alkyl and $-Z^{18}-C_{6-14}$-aryl, wherein $C_{1-30}$-alkyl and $C_{6-14}$-aryl are optionally substituted with 1 to 4 substituents $R^m$, wherein each $R^m$ is independently selected from the group consisting of halogen, —CN and *=O, and wherein $C_{6-14}$-aryl is optionally substituted with 1 to 4 substituents $R^n$, wherein each $R^n$ is independently selected from the group consisting of $C_{1-20}$-alkyl and $C_{1-20}$-alkoxy, wherein $Z^{18}$ at each occurrence is a covalent bond, wherein $R^1$ is hydrogen or $C_{1-30}$-alkyl, or L is wherein $R^{23}$ and $R^{24}$ are the same or different and are H, $C_{1-30}$-alkyl, $C_{1-30}$-haloalkyl, $-X^7-R^{25}$ or $-X^8-Ar^{13}$, wherein $X^7$ at each occurrence is independently $-[Z^{19}-O]_c-$, $-[Z^{19}-S-]_c-$, or $-[S-Z^{19}]_c-S-$, wherein $Z^{19}$ at each occurrence is independently $C_{1-6}$-alkylene or $C_{1-6}$-haloalkylene, c at each occurrence is independently an integer from 1 to 10 and $R^{25}$ at each occurrence is independently $C_{1-30}$-alkyl or $C_{1-30}$-haloalkyl, $X^8$ at each occurrence is independently $-Z^{21}-O-Z^{22}-$, $-Z^{21}-S-Z^{22}-$, $C_{1-30}$-alkylene or $C_{1-30}$-haloalkylene, wherein $Z^{21}$ and $Z^{22}$ at each occurrence are independently $C_{1-6}$-alkylene or $C_{1-6}$-haloalkylene, and $Ar^{13}$ at each occurrence is independently $C_{6-14}$-aryl, optionally substituted with 1 to 5 substituents $R^o$, wherein each $R^o$ is independently selected from the group consisting of halogen $C_{1-6}$-alkyl and $C_{1-6}$-alkoxy.

Even more preferably,

L is a bivalent 5 to 18 membered aromatic heterocyclic residue selected from the group consisting of

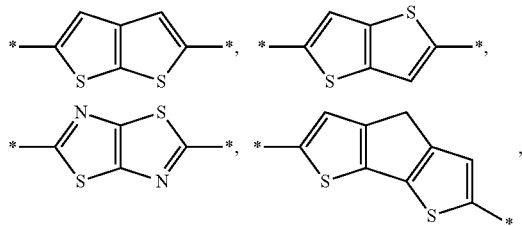

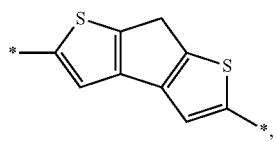

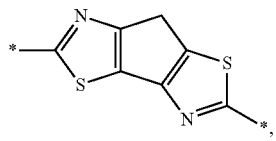

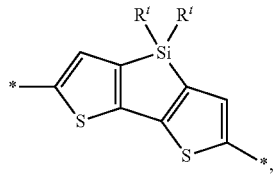

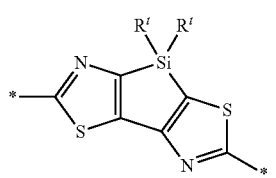

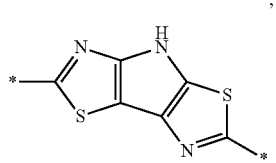

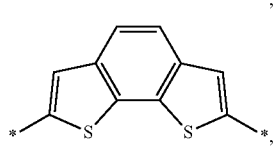

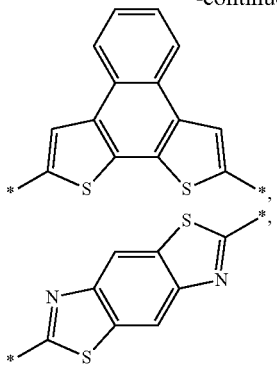

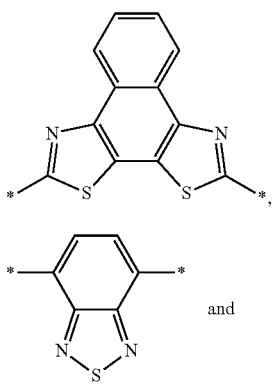

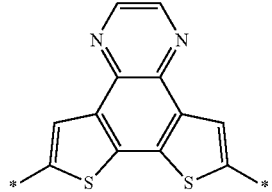

and wherein the bivalent 5 to 18 membered aromatic heterocyclic residue is optionally substituted with 1 to 4 substituents $R^l$, wherein each $R^l$ $R^l$ is independently selected from the group consisting of $C_{1-30}$-alkyl and $-Z^{18}-C_{6-14}$-aryl, wherein $C_{1-30}$-alkyl and $C_{6-14}$-aryl are optionally substituted with 1 to 4 substituents $R^m$, wherein each $R^m$ is independently selected from the group consisting of halogen, $-CN$ and $*=O$, and wherein $C_{6-14}$-aryl is optionally substituted with 1 to 4 substituents $R^n$, wherein each $R^n$ is independently selected from the group consisting of $C_{1-20}$-alkyl and $C_{1-20}$-alkoxy, wherein $Z^{18}$ at each occurrence is a covalent bond, wherein $R^1$ is hydrogen or $C_{1-30}$-alkyl, or L is

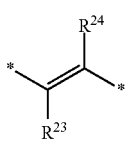

wherein $R^{23}$ and $R^{24}$ are the same or different and are H, $C_{1-30}$-alkyl, $C_{1-30}$-haloalkyl, $-X^7-R^{25}$ or $-X^8-Ar^{13}$, wherein $X^7$ at each occurrence is independently $-[Z^{19}-O]_c-$, $-[Z^{19}-S-]_c-$, or $-[S-Z^{19}]_c-S-$, wherein $Z^{19}$ at each occurrence is independently $C_{1-6}$-alkylene or $C_{1-6}$-haloalkylene, c at each occurrence is independently an integer from 1 to 10 and $R^{25}$ at each occurrence is independently $C_{1-30}$-alkyl or $C_{1-30}$-haloalkyl, $X^8$ at each occurrence is independently —$Z^{21}$—O—$Z^{22}$—, —$Z^{21}$—S—$Z^{22}$—, $C_{1-30}$-alkylene or $C_{1-30}$-haloalkylene, wherein $Z^{21}$ and $Z^{22}$ at each occurrence are independently $C_{1-6}$-alkylene or $C_{1-6}$-haloalkylene, and $Ar^{13}$ at each occurrence is independently $C_{6-14}$-aryl, optionally substituted with 1 to 5 substituents $R^o$, wherein each $R^o$ is independently selected from the group consisting of halogen $C_{1-6}$-alkyl and $C_{1-6}$-alkoxy.

Most preferably,

L is

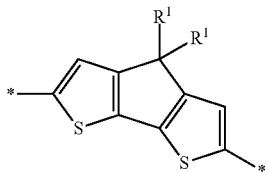

wherein each $R^l$ is independently $C_{1-30}$-alkyl, preferably n-octyl, n-(2-ethyl)hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$), more preferably, n-hexadecyl, or L is

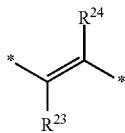

wherein $R^{23}$ and $R^{24}$ are the same or different and are H, $C_{1-30}$-alkyl or $C_{1-30}$-haloalkyl, in particular H.

Preferably, q, r and s are 0 or 1, with the proviso that q, r and s are not all 0 at the same time.

Preferably, n is an integer from 1 to 5000, 1 to 1000, 1 to 100, 1 to 50 or from 1 to 30, for example n can be an integer from 2 to 5000, 2 to 1000, 2 to 50, 2 to 30. In some embodiments, n can be an integer from 4 to 1000, 4 to 100, 8 to 1000 or 8 to 100.

In one embodiment, $A^1$ and $A^2$ are S,

E is

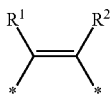

wherein $R^1$ and $R^2$ are the same or different and are H, $C_{1-30}$-alkyl, $C_{1-30}$-haloalkyl, —$X^1$—$R^6$ or —$X^2$—$Ar^1$, wherein $X^1$ at each occurrence is independently —[$Z^1$—O]$_a$—, —[$Z^1$—S]$_a$—, or —[S—$Z^1$]$_a$—S—, wherein $Z^1$ at each occurrence is independently $C_{1-6}$-alkylene or $C_{1-6}$-haloalkylene, a at each occurrence is independently an integer from 1 to 10 and $R^6$ at each occurrence is independently $C_{1-30}$-alkyl or $C_{1-30}$-haloalkyl, $X^2$ at each occurrence is independently —$Z^3$—O—$Z^4$—, —$Z^3$—S—$Z^4$—, $C_{1-30}$-alkylene or $C_{1-30}$-haloalkylene, wherein $Z^3$ and $Z^4$ at each occurrence are independently $C_{1-6}$-alkylene or $C_{1-6}$-haloalkylene, and $Ar^1$ at each occurrence is independently $C_{6-14}$-aryl, optionally substituted with 1 to 5 substituents $R^a$, wherein each $R^a$ is independently selected from the group consisting of halogen $C_{1-6}$-alkyl and $C_{1-6}$-alkoxy.

L is a bivalent 5 to 18 membered aromatic heterocyclic residue, wherein the bivalent 5 to 18 membered aromatic heterocyclic residue is optionally substituted with 1 to 4 substituents $R^l$, wherein each $R^l$ is independently selected from the group consisting of $C_{1-30}$-alkyl, —$Z^{18}$—O—$C_{1-30}$-alkyl, —$Z^{18}$—S—$C_{1-30}$-alkyl, —$Z^{18}$—$C_{3-10}$-cycloalkyl, —$Z^{18}$—$C_{6-14}$-aryl, —$Z^{18}$-monovalent 3 to 12 membered aliphatic heterocyclic residue and —$Z^{18}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN and *=O, and wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^n$, wherein each $R^n$ is independently selected from the group consisting of $C_{1-20}$-alkyl, $C_{1-20}$-alkoxy, $C_{1-20}$-haloalkyl, wherein $Z^{18}$ at each occurrence is independently $C_{1-6}$-alkylene, $C_{1-6}$-haloalkylene or a covalent bond, q and s are 0, r is 1, and n is an integer from 1 to 1000, preferably 4 to 100.

In a second embodiment, $A^1$ and $A^2$ are S,

E is

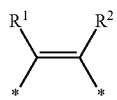

wherein $R^1$ and $R^2$ are the same or different and are H, $C_{1-30}$-alkyl, $C_{1-30}$-haloalkyl, —$X^1$—$R^6$ or —$X^2$—$Ar^1$, wherein $X^1$ at each occurrence is independently —[$Z^1$—O]$_a$—, —[$Z^1$—S]$_a$—, or —[S—$Z^1$]$_a$—S—, wherein
$Z^1$ at each occurrence is independently $C_{1-6}$-alkylene or $C_{1-6}$-haloalkylene,
a at each occurrence is independently an integer from 1 to 10 and
$R^6$ at each occurrence is independently $C_{1-30}$-alkyl or $C_{1-30}$-haloalkyl,
$X^2$ at each occurrence is independently —$Z^3$—O—$Z^4$—, —$Z^3$—S—$Z^4$—, $C_{1-30}$-alkylene or $C_{1-30}$-haloalkylene,
wherein
$Z^3$ and $Z^4$ at each occurrence are independently $C_{1-6}$-alkylene or $C_{1-6}$-haloalkylene, and
$Ar^1$ at each occurrence is independently $C_{6-14}$-aryl, optionally substituted with 1 to 5 substituents $R^a$, wherein each $R^a$ is independently selected from the group consisting of halogen $C_{1-6}$-alkyl and $C_{1-6}$-alkoxy,
$G^1$ and $G^2$ are the same or different and are phenylene such as

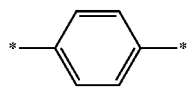 [SMILES: *c1ccc(*)cc1]

or, preferably, a monocyclic bivalent 5 to 8 membered aromatic heterocyclic residue selected from the group consisting of

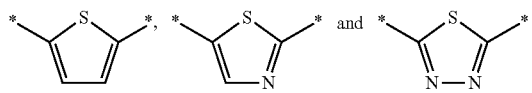

which phenylene or monocyclic bivalent 5 to 8 membered aromatic heterocyclic residue are optionally substituted with 1 to 2 substituents $R^i$, wherein each $R^i$ is independently selected from the group consisting of $C_{1-30}$-alkyl, —$Z^{17}$—O—$C_{1-30}$-alkyl, —$Z^{17}$—S—$C_{1-30}$ alkyl, —$Z^{17}$—$C_{3-10}$-cycloalkyl, —$Z^{17}$—$C_{6-14}$-aryl, —$Z^{17}$-monovalent 3 to 12 membered aliphatic heterocyclic residue and —$Z^{17}$-monovalent 5 to 14 membered aromatic heterocyclic residue,
wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN and *=O, and
wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, $C_{1-20}$-haloalkyl,
wherein
$Z^{17}$ at each occurrence is independently $C_{1-6}$-alkylene, $C_{1-6}$-haloalkylene or a covalent bond.

L is

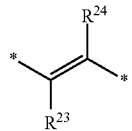

wherein
$R^{23}$ and $R^{24}$ are the same or different and are H, $C_{1-30}$-alkyl, $C_{1-30}$-haloalkyl, —$X^7$—$R^{25}$ or —$X^5$—$Ar^{13}$,
wherein
$X^7$ at each occurrence is independently —$[Z^{19}$—O$]_c$—, —$[Z^{19}$—S—$]_c$—, or —$[S$—$Z^{19}]_c$—S—,
wherein
$Z^{19}$ at each occurrence is independently $C_{1-6}$-alkylene or $C_{1-6}$-haloalkylene,
c at each occurrence is independently an integer from 1 to 10 and
$R^{25}$ at each occurrence is independently $C_{1-30}$-alkyl or $C_{1-30}$-haloalkyl,
$X^8$ at each occurrence is independently —$Z^{21}$—O—$Z^{22}$—, —$Z^{21}$—S—$Z^{22}$—, $C_{1-30}$-alkylene or $C_{1-30}$-haloalkylene,
wherein
$Z^{21}$ and $Z^{22}$ at each occurrence are independently $C_{1-6}$-alkylene or $C_{1-6}$-haloalkylene, and
$Ar^{13}$ at each occurrence is independently $C_{6-14}$-aryl, optionally substituted with 1 to 5 substituents $R^o$, wherein each $R^o$ is independently selected from the group consisting of halogen $C_{1-6}$-alkyl and $C_{1-6}$-alkoxy,
q and s are 1,
r is 1,
and
n is an integer from 1 to 1000, preferably from 2 to 50.
In a third embodiment,
$A^1$ and $A^2$ are S,
E is

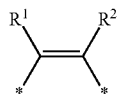

wherein
$R^1$ and $R^2$ are the same or different and are H, $C_{1-30}$-alkyl, $C_{1-30}$-haloalkyl, —$X^1$—$R^6$ or —$X^2$—$Ar^1$,
wherein
$X^1$ at each occurrence is independently —$[Z^1$—O$]_a$—, —$[Z^1$—S—$]_a$—, or —$[S$—$Z^1]_a$—S—,
wherein
$Z^1$ at each occurrence is independently $C_{1-6}$-alkylene or $C_{1-6}$-haloalkylene,
a at each occurrence is independently an integer from 1 to 10 and
$R^6$ at each occurrence is independently $C_{1-30}$-alkyl or $C_{1-30}$-haloalkyl,
$X^2$ at each occurrence is independently —$Z^3$—O—$Z^4$—, —$Z^3$—S—$Z^4$—, $C_{1-30}$-alkylene or $C_{1-30}$-haloalkylene,
wherein
$Z^3$ and $Z^4$ at each occurrence are independently $C_{1-6}$-alkylene or $C_{1-6}$-haloalkylene, and
$Ar^1$ at each occurrence is independently $C_{6-14}$-aryl, optionally substituted with 1 to 5 substituents $R^a$, wherein each $R^a$ is independently selected from the group consisting of halogen $C_{1-6}$-alkyl and $C_{1-6}$-alkoxy, $G^1$ and $G^2$ are the same or different and are phenylene such as

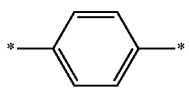

or, preferably, a monocyclic bivalent 5 to 8 membered aromatic heterocyclic residue selected from the group consisting of

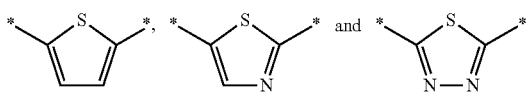

which phenylene or monocyclic bivalent 5 to 8 membered aromatic heterocyclic residue are optionally substituted with 1 to 2 substituents $R^i$ wherein each $R^i$ is independently selected from the group consisting of $C_{1-30}$-alkyl, —$Z^{17}$—O—$C_{1-30}$-alkyl, —$Z^{17}$—S—$C_{1-30}$-alkyl, —$Z^{17}$—$C_{3-10}$-cycloalkyl, —$Z^{17}$—$C_{6-14}$-aryl, —$Z^{17}$-monovalent 3 to 12 membered aliphatic heterocyclic residue and —$Z^{17}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN and *=O, and wherein $C_{3-30}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, $C_{1-20}$-haloalkyl, wherein $Z^{17}$ at each occurrence is independently $C_{1-6}$-alkylene, $C_{1-6}$-haloalkylene or a covalent bond, q and s are 1, r is 0, and n is an integer from 1 to 1000, preferably from 1 to 30.

In a fourth embodiment, $A^1$ and $A^2$ are S,

E is

wherein $R^3$ is —$X^5$—$Ar^7$, —$X^5$—$Ar^8$—$Ar^7$, —$X^5$—$Ar^8$—$R^{13}$ or —$X^5$—$Ar^8$—$Ar^9$—$R^{13}$, wherein $X^5$ at each occurrence is a covalent bond, $Ar^7$ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl, $Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl, and $R^{13}$ at each occurrence is independently $C_{1-20}$-alkyl, $C_{2-20}$-alkenyl, $C_{1-20}$-haloalkyl or $C_{1-20}$-alkoxy, $G^1$ and $G^2$ are the same or different and are phenylene such as

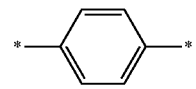

or, preferably, a monocyclic bivalent 5 to 8 membered aromatic heterocyclic residue selected from the group consisting of

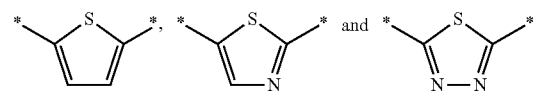

which phenylene or monocyclic bivalent 5 to 8 membered aromatic heterocyclic residue are optionally substituted with 1 to 2 substituents $R^i$, wherein each $R^i$ is independently selected from the group consisting of $C_{1-30}$-alkyl, —$Z^{17}$—O—$C_{1-30}$-alkyl, —$Z^{17}$—S—$C_{1-30}$-alkyl, —$Z^{17}$—$C_{3-10}$-cycloalkyl, —$Z^{17}$—$C_{6-14}$-aryl, —$Z^{17}$-monovalent 3 to 12 membered aliphatic heterocyclic residue and —$Z^{17}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN and *=O, and wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, $C_{1-20}$-haloalkyl, wherein $Z^{17}$ at each occurrence is independently $C_{1-6}$-alkylene, $C_{1-6}$-haloalkylene or a covalent bond, L is

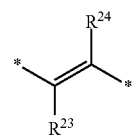

wherein $R^{23}$ and $R^{24}$ are the same or different and are H, $C_{1-30}$-alkyl, $C_{1-30}$-haloalkyl, —$X^7$—$R^{25}$ or —$X^8$—$Ar^{13}$, wherein $X^7$ at each occurrence is independently $-[Z^{19}-O]_c-$, $-[Z^{19}-S-]_c-$, or $-[S-Z^{19}]_c-S-$, wherein $Z^{19}$ at each occurrence is independently $C_{1-6}$-alkylene or $C_{1-6}$-haloalkylene, c at each occurrence is independently an integer from 1 to 10 and $R^{25}$ at each occurrence is independently $C_{1-30}$-alkyl or $C_{1-30}$-haloalkyl, $X^8$ at each occurrence is independently $-Z^{21}-O-Z^{22}-$, $-Z^{21}-S-Z^{22}-$, $C_{1-30}$-alkylene or $C_{1-30}$-haloalkylene, wherein $Z^{21}$ and $Z^{22}$ at each occurrence are independently $C_{1-6}$-alkylene or $C_{1-6}$-haloalkylene, and $Ar^{13}$ at each occurrence is independently $C_{6-14}$-aryl, optionally substituted with 1 to 5 substituents $R°$, wherein each $R°$ is independently selected from the group consisting of halogen $C_{1-6}$-alkyl and $C_{1-6}$-alkoxy, q and s are 1, r is 1, and n is an integer from 1 to 1000, preferably from 2 to 50.

Examples of compounds, oligomers or polymers of formula 1 are

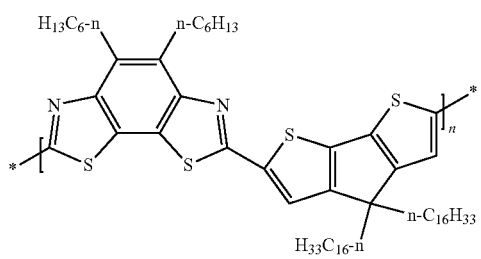
(1a)

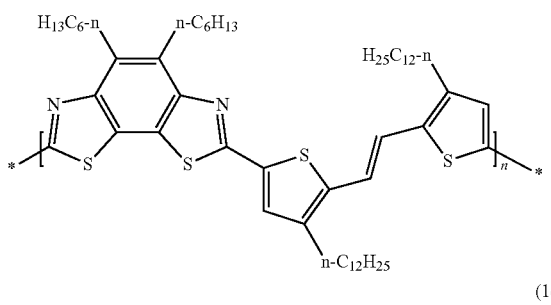
(1b)

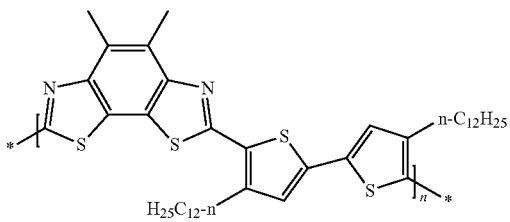
(1c)

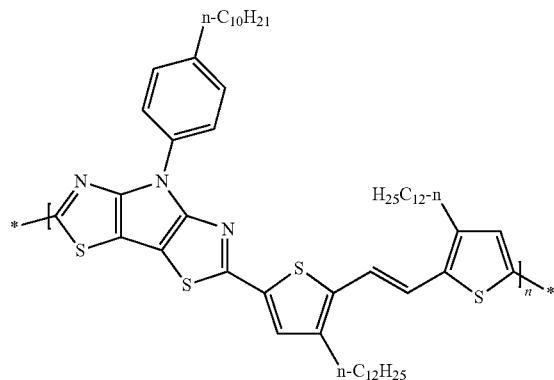
(1d)

wherein n is an integer from 1 to 1000, preferably 1 to 100, 1 to 50 or from 1 to 30, for example n can be an integer from 2 to 1000, 2 to 100, 2 to 50, 2 to 30, or an integer from 4 to 100 or 8 to 100.

Also part of the present invention is a process for the preparation of the compound, oligomer or polymer of formula

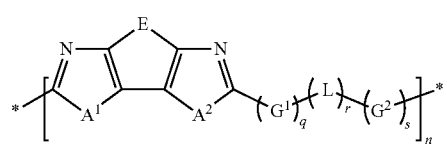
(1)

wherein $A^1$ and $A^2$ can be the same or different and are S or Se,

E is selected from the group consisting of

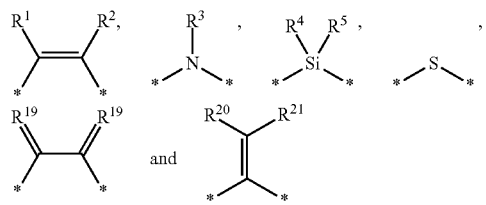

and wherein $R^1$ and $R^2$ can be the same or different and are H, halogen, $-$CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, $-X^1-R^6$, $-X^2-Ar^1$, $-X^2-Ar^2-Ar^1$, $-X^2-Ar^2-R^7$ or $-X^2-Ar^2-Ar^3-R^7$, wherein $X^1$ at each occurrence is independently $-O-$, $-[Z^1-O]_a-$, $-[O-Z^1]_a-O-$, $-S-$, $-[Z^1-S]_a-$, $-[S-Z^1]_a-S-$, $-S(O)$, $-C(O)-$, $-C(O)O-$, $-C(O)NR^8-$, $C(O)S-$, $-O(CO)-$, $-S(CO)-$, $-NR^8C(O)-$ or $-NR^8-$, wherein $Z^1$ at each occurrence is independently $C_{1-6}$-alkylene, $C_{2-6}$-alkenylene or $C_{1-6}$-haloalkylene, a at each occurrence is independently an integer from 1 to 10 and $R^8$ at each occurrence is independently H, $C_{1-20}$-alkyl, or —$Z^2$—$C_{6-14}$-aryl,
  wherein
    $Z^2$ at each occurrence is independently $C_{1-6}$-alkylene, $C_{2-6}$-alkenylene, $C_{1-6}$-haloalkylene or a covalent bond,
$R^6$ at each occurrence is independently $C_{1-30}$-alkyl, $C_{2-30}$-alkenyl or $C_{1-30}$-haloalkyl,
$X^2$ at each occurrence is independently —$Z^3$—O—$Z^4$—, —$Z^3$—S—$Z^4$—, —S(O)—, —O(O)—, —C(O)O—, —(CO)NR$^9$, —C(O)S—, —O(CO)—, —S(CO)—, —NR$^9$C(O)—, —NR$^9$—, —$Z^3$—SiR$^9{}_2$—$Z^4$—, $C_{1-30}$-alkylene, $C_{2-30}$-alkenylene, $C_{1-30}$-haloalkylene or a covalent bond,
  wherein
    $Z^3$ and $Z^4$ at each occurrence are independently $C_{1-6}$-alkylene, $C_{2-6}$-alkenylene, $C_{1-6}$-haloalkylene or a covalent bond, and
    $R^9$ at each occurrence is independently H, $C_{1-20}$-alkyl, or —$Z^5$—$C_{6-14}$-aryl,
      wherein
        $Z^5$ at each occurrence is independently $C_{1-6}$-alkylene, $C_{2-6}$-alkenylene, $C_{1-6}$-haloalkylene or a covalent bond,
$Ar^1$ at each occurrence is independently $C_{6-14}$-aryl or monovalent 5 to 14 membered aromatic hetrocyclic residue, each optionally substituted with 1 to 5 substituents $R^a$, wherein each $R^a$ is independently selected from the group consisting of halogen, CN, $C_{1-6}$-alkyl, $C_{1-6}$-alkoxy and $C_{1-6}$-haloalkyl,
$Ar^2$ and $Ar^3$ at each occurrence are independently $C_{6-14}$-arylene or bivalent 5 to 14 membered aromatic heterocyclic residue, each optionally substituted with 1 to 4 substituents $R^b$, wherein each $R^b$ is independently selected from the group consisting of halogen, CN, $C_{1-6}$-alkyl, $C_{1-6}$-alkoxy and $C_{1-6}$-haloalkyl, and
$R^7$ at each occurrence is independently $C_{1-20}$-alkyl, $C_{2-20}$-alkenyl, $C_{1-20}$-haloalkyl, $C_{1-20}$-alkoxy, —$X^3$—$Ar^4$, —$X^3$—$Ar^5$—$Ar^4$, —$X^3$—$Ar^5$—$R^{10}$, or —$X^3$—$Ar^5$—$Ar^6$—$R^{10}$,
  wherein
    $X^3$ at each occurrence is independently —$Z^6$—O—$Z^7$—, —$Z^6$—S—$Z^7$, —S(O)—, —C(O)—, —C(O)O—, —(CO)NR$^{11}$, —C(O)S—, —O(CO)—, —S(CO)—, —NR$^{11}$C(O)—, —NR$^{11}$—, —$Z^6$—SiR$^{11}{}_2$—$Z^7$—, $C_{1-30}$-alkylene, $C_{2-30}$-alkenylene, $C_{1-30}$-haloalkylene or a covalent bond,
      wherein
        $Z^6$ and $Z^7$ at each occurrence are independently $C_{1-6}$-alkylene, $C_{2-6}$-alkenylene, $C_{1-6}$-haloalkylene or a covalent bond, and
        $R^{11}$ at each occurrence is independently H, $C_{1-20}$-alkyl or —$Z^8$—$C_{6-14}$-aryl,
          wherein
            $Z^8$ at each occurrence is independently $C_{1-6}$-alkylene, $C_{2-6}$-alkenylene, $C_{1-6}$-haloalkylene or a covalent bond,
    $Ar^4$ at each occurrence is independently $C_{6-14}$-aryl or monovalent 5 to 14 membered aromatic heterocyclic residue, each optionally substituted with 1 to 5 substituents $R^c$, wherein each $R^c$ is independently selected from the group consisting of halogen, CN, $C_{1-6}$-alkyl, $C_{1-6}$-alkoxy and $C_{1-6}$-haloalkyl,
    $Ar^5$ and $Ar^6$ at each occurrence are independently $C_{6-14}$-arylene or bivalent 5 to 14 membered aromatic heterocyclic residue, each optionally substituted with 1 to 4 substituents $R^d$, wherein each $R^d$ is independently selected from the group consisting of halogen, CN, $C_{1-6}$-alkyl, $C_{1-6}$-alkoxy and $C_{1-6}$-haloalkyl, and
    $R^{10}$ at each occurrence is independently $C_{1-20}$-alkyl, $C_{2-20}$-alkenyl, $C_{1-20}$-haloalkyl or $C_{1-20}$-alkoxy,
$R^3$, $R^4$ and $R^5$ can be the same or different and are H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^4$—$R^{12}$, —$X^5$—$Ar^7$, —$X^5$—$Ar^8$—$Ar^7$, —$X^5$—$Ar^8$—$R^{13}$ or —$X^5$—$Ar^8$—$Ar^9$—$R^{13}$,
wherein
  $X^4$ at each occurrence is independently —$[Z^9$—O$]_b$—, —$[Z^9$—S—$]_b$, —S(O)—, —C(O)—, —C(O)O—, —C(O)NR$^{14}$— or C(O)S—,
    wherein
      $Z^9$ at each occurrence is independently $C_{1-6}$-alkylene, $C_{2-6}$-alkenylene or $C_{1-6}$-haloalkylene,
      b at each occurrence is independently an integer from 1 to 10 and
      $R^{14}$ at each occurrence is independently H, $C_{1-20}$-alkyl, or —$Z^{10}$—$C_{6-14}$-aryl,
        wherein
          $Z^{10}$ at each occurrence is independently $C_{1-6}$-alkylene, $C_{2-6}$-alkenylene, $C_{1-6}$-haloalkylene or a covalent bond,
  $R^{12}$ at each occurrence is independently $C_{1-30}$-alkyl, $C_{2-30}$-alkenyl or $C_{1-30}$-haloalkyl,
  $X^5$ at each occurrence is independently —$Z^{11}$—O—$Z^{12}$, —$Z^{11}$—S—$Z^{12}$—, —S(O)—, —O(O)—, —C(O)O—, —(CO)NR$^{15}$, —C(O)S—, —$Z^{11}$—SiR$^{15}{}_2$—$Z^{12}$—, $C_{1-30}$-alkylene, $C_{2-30}$-alkenylene, $C_{1-30}$-haloalkylene or a covalent bond,
    wherein
      $Z^{11}$ at each occurrence is independently $C_{1-6}$-alkylene, $C_{2-6}$-alkenylene or $C_{1-6}$-haloalkylene,
      $Z^{12}$ at each occurrence is independently $C_{1-6}$-alkylene, $C_{2-6}$-alkenylene, $C_{1-6}$-haloalkylene or a covalent bond, and
      $R^{15}$ at each occurrence is independently H, $C_{1-20}$-alkyl, or —$Z^{13}$—$C_{6-14}$-aryl,
        wherein
          $Z^{13}$ at each occurrence is independently $C_{1-6}$-alkylene, $C_{2-6}$-alkenylene, $C_{1-6}$-haloalkylene or a covalent bond,
  $Ar^7$ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl,
  $Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl and
  $R^{13}$ at each occurrence is independently $C_{1-20}$-alkyl, $C_{2-20}$-alkenyl, $C_{1-20}$-haloalkyl, $C_{1-20}$-alkoxy, —$X^6$—$Ar^{10}$, —$X^6$—$Ar^{11}$—$Ar^{10}$, —$X^6$—$Ar^{11}$—$R^{16}$, or —$X^6$—$Ar^{11}$—$Ar^{12}$—$R^{17}$, wherein
X$^6$ at each occurrence is independently —Z$^{14}$—O—Z$^{15}$—, —Z$^{14}$—S—Z$^{15}$, —S(O)—, —C(O)—, —C(O)O—, —(CO)NR$^{18}$, —C(O)S—, —O(CO)—, —S(CO)—, —NR$^{18}$C(O)—, —NR$^{18}$—,
—Z$^{14}$—SiR$^{18}{}_2$—Z$^{15}$—, C$_{1-30}$-alkylene, C$_{2-30}$-alkenylene, C$_{1-30}$-haloalkylene or a covalent bond, wherein
Z$^{14}$ and Z$^{15}$ at each occurrence are independently C$_{1-6}$-alkylene, C$_{2-6}$-alkenylene, C$_{1-6}$-haloalkylene or a covalent bond, and
R$^{18}$ at each occurrence is independently H, C$_{1-20}$-alkyl or —Z$^{16}$—C$_{6-14}$-aryl,
wherein
Z$^{16}$ at each occurrence is independently C$_{1-6}$-alkylene, C$_{2-6}$-alkenylene, C$_{1-6}$-haloalkylene or a covalent bond,
Ar$^{10}$ at each occurrence is independently C$_{6-14}$-aryl or monovalent 5 to 14 membered aromatic heterocyclic residue, each optionally substituted with 1 to 5 substituents R$^g$, wherein each R$^g$ is independently selected from the group consisting of halogen, CN, C$_{1-6}$-alkyl, C$_{1-6}$-alkoxy and C$_{1-6}$-haloalkyl,
Ar$^{11}$ and Ar$^{12}$ at each occurrence are independently C$_{6-14}$-arylene or bivalent 5 to 14 membered aromatic heterocyclic residue, each optionally substituted with 1 to 4 substituents R$^h$, wherein each R$^h$ is independently selected from the group consisting of halogen, CN, C$_{1-6}$-alkyl, C$_{1-6}$-alkoxy and C$_{1-6}$-haloalkyl and
R$^{17}$ at each occurrence is independently C$_{1-20}$-alkyl, C$_{2-20}$-alkenyl, C$_{1-20}$-haloalkyl or C$_{1-20}$-alkoxy,
R$^{19}$ is O or C(CN)$_2$, and
R$^{20}$ and R$^{21}$ are the same or different and are R$^{22}$ or CN, wherein R$^{22}$ has the same meaning as R$^1$,
G$^1$ and G$^2$ are the same or different and are phenylene or a monocyclic bivalent 5 to 8 membered aromatic heterocyclic residue, which phenylene and monocyclic bivalent 5 to 8 membered aromatic heterocyclic residue are optionally substituted with 1 to 4 substituents R$^i$, wherein each R$^i$ is independently selected from the group consisting of halogen, —CN, —NO$_2$, OH, C$_{1-30}$-alkyl, C$_{2-30}$-alkenyl, C$_{2-30}$-alkynyl, —Z$^{17}$—O—C$_{1-30}$-alkyl, —Z$^{17}$—S—C$_{1-30}$-alkyl, —Z$^{17}$—C$_{3-10}$-cycloalkyl, —Z$^{17}$—C$_{5-10}$-cycloalkenyl, —Z$^{17}$—C$_{8-10}$-cycloalkynyl, —Z$^{17}$—C$_{6-14}$-aryl, —Z$^{17}$-monovalent 3 to 12 membered aliphatic heterocyclic residue and —Z$^{17}$-monovalent 5 to 14 membered aromatic heterocyclic residue,
wherein C$_{1-30}$-alkyl, C$_{2-30}$-alkenyl, C$_{2-30}$-alkynyl, C$_{3-30}$-cycloalkyl, C$_{5-10}$-cycloalkenyl, C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^j$, wherein each R$^j$ is independently selected from the group consisting of halogen, —CN, —NO$_2$, *=O, —OH, —NH$_2$, —NH(C$_{1-20}$-alkyl), —N(C$_{1-20}$-alkyl)$_2$, —N(C$_{1-20}$-alkyl)—C$_{6-14}$-aryl, —N(C$_{6-14}$-aryl)$_2$, —S(O)$_m$H, —S(O)$_m$—C$_{1-20}$-alkyl, —S(O)$_2$OH, —S(O)$_m$—OC$_{1-20}$-alkyl, —S(O)$_m$—OC$_{6-14}$-aryl, —CHO, —C(O)—C$_{1-20}$-alkyl, —C(O)—C$_{6-14}$-aryl, —C(O)OH, —C(O)—OC$_{1-20}$-alkyl, —C(O)—OC$_{6-14}$-aryl, —C(O)NH$_2$, —C(O)NH—C$_{1-20}$-alkyl, —C(O)N(C$_{1-20}$-alkyl)$_2$, —C(O)NH—C$_{6-14}$-aryl, —C(O)N(C$_{1-20}$-alkyl)-C$_{6-14}$-aryl, —C(O)N(C$_{6-14}$-aryl)$_2$, —C(S)NH$_2$, —C(S)NH—C$_{1-20}$-alkyl, —C(S)N(C$_{1-20}$-alkyl)$_2$, —C(S)N(C$_{6-14}$-aryl)$_2$, —C(S)N(C$_{1-20}$-alkyl)-C$_{6-14}$-aryl, —C(S)NH—C$_{6-14}$-aryl, —S(O)$_m$NH$_2$, —S(O)$_m$NH(C$_{1-20}$-alkyl), —S(O)$_m$N(C$_{1-20}$-alkyl)$_2$, —S(O)$_m$NH(C$_{6-14}$-aryl), —S(O)$_m$N(C$_{1-20}$-alkyl)-C$_{6-14}$-aryl, —S(O)$_m$N(C$_{6-14}$-aryl)$_2$, SiH$_3$, SiH(C$_{1-20}$-alkyl)$_2$, SiH$_2$(C$_{1-20}$-alkyl) and Si(C$_{1-20}$-alkyl)$_3$, and
wherein C$_{3-10}$-cycloalkyl, C$_{5-10}$-cycloalkenyl, —C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^k$, wherein each R$^k$ is independently selected from the group consisting of C$_{1-20}$-alkyl, C$_{2-20}$-alkenyl, C$_{2-20}$-alkynyl, C$_{1-20}$-alkoxy, —S—C$_{1-20}$-alkyl, C$_{1-20}$-haloalkyl,
wherein
Z$^{17}$ at each occurrence is independently C$_{1-6}$-alkylene, C$_{2-6}$-alkenylene, C$_{1-6}$-haloalkylene or a covalent bond, and
m at each occurrence is independently 0, 1 or 2,
L is C$_{6-24}$-arylene or a bivalent 5 to 18 membered aromatic heterocyclic residue, wherein C$_{6-24}$-arylene and bivalent 5 to 18 membered aromatic heterocyclic residue are optionally substituted with 1 to 4 substituents R$^l$, wherein each R$^l$ is independently selected from the group consisting of halogen, —CN, —NO$_2$, *=O, OH, *=C(C$_{1-30}$-alkyl)$_2$, C$_{1-30}$-alkyl, C$_{2-30}$-alkenyl, C$_{2-30}$-alkynyl, —Z$^{18}$—O—C$_{1-30}$-alkyl, —Z$^{18}$—C$_{3-10}$-cycloalkyl, —Z$^{18}$—C$_{5-10}$-cycloalkenyl, —Z$^{18}$—C$_{8-10}$-cycloalkynyl, —Z$^{18}$—C$_{6-14}$-aryl, —Z$^{18}$-monovalent 3 to 12 membered aliphatic heterocyclic residue and —Z$^{18}$-monovalent 5 to 14 membered aromatic heterocyclic residue,
wherein C$_{1-30}$-alkyl, C$_{2-30}$-alkenyl, C$_{2-30}$-alkynyl, C$_{3-10}$-cycloalkyl, C$_{5-10}$-cycloalkenyl, C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^m$, wherein each R$^m$ is independently selected from the group consisting of halogen, —CN, —NO$_2$, *=O, —OH, —NH$_2$, —NH(C$_{1-20}$-alkyl), —N(C$_{1-20}$-alkyl)$_2$, —N(C$_{1-20}$-alkyl)-C$_{6-14}$-aryl, —N(C$_{6-14}$-aryl)$_2$, —S(O)$_o$H, —S(O)$_o$—C$_{1-20}$-alkyl, —S(O)$_2$OH, —S(O)$_o$—OC$_{1-20}$-alkyl, —S(O)$_o$—OC$_{6-14}$-aryl, —CHO, —C(O)—C$_{1-20}$-alkyl, —C(O)—C$_{6-14}$-aryl, —C(O)OH, —C(O)—OC$_{1-20}$-alkyl, —C(O)—OC$_{6-14}$-aryl, —C(O)NH$_2$, —C(O)NH—C$_{1-20}$-alkyl, —C(O)N(C$_{1-20}$-alkyl)$_2$, —C(O)NH—C$_{6-14}$-aryl, —C(O)N(C$_{1-20}$-alkyl)-C$_{6-14}$-aryl, —C(O)N(C$_{6-14}$-aryl)$_2$, —C(S)NH$_2$, —C(S)NH—C$_{1-20}$-alkyl, —C(S)N(C$_{1-20}$-alkyl)$_2$, —C(S)N(C$_{6-14}$-aryl)$_2$, —C(S)N(C$_{1-20}$-alkyl)-C$_{6-14}$-aryl, —C(S)NH—C$_{6-14}$-aryl, —S(O)$_o$NH$_2$, —S(O)$_o$NH(C$_{1-20}$-alkyl), —S(O)$_o$N(C$_{1-20}$-alkyl)$_2$, —S(O)$_o$NH(C$_{6-14}$-aryl), —S(O)$_o$N(C$_{1-20}$-alkyl)-C$_{6-14}$-aryl, —S(O)$_o$N(C$_{6-14}$-aryl)$_2$, SiH$_3$, SiH(C$_{1-20}$-alkyl)$_2$, SiH$_2$(C$_{1-20}$-alkyl) and Si(C$_{1-20}$-alkyl)$_3$, and
wherein C$_{3-30}$-cycloalkyl, C$_{5-10}$-cycloalkenyl, —C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R$^n$, wherein each R$^n$ is independently selected from the group consisting of C$_{1-20}$-alkyl, C$_{2-20}$-alkenyl, C$_{2-20}$-alkynyl, C$_{1-20}$-alkoxy, C$_{1-20}$-haloalkyl,
wherein
Z$^{18}$ at each occurrence is independently C$_{1-6}$-alkylene, C$_{2-6}$-alkenylene, C$_{1-6}$-haloalkylene or a covalent bond, and
o at each occurrence is independently 0, 1 or 2, or L is

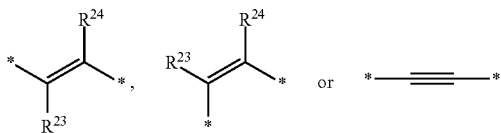

wherein

R$^{23}$ and R$^{24}$ can be the same or different and are H, halogen, —CN, C$_{1-30}$-alkyl, C$_{2-30}$-alkenyl, C$_{2-20}$-alkynyl, C$_{3-10}$-cycloalkyl, C$_{5-10}$-cycloalkenyl, C$_{8-10}$-cycloalkynyl, C$_{1-30}$-haloalkyl, monovalent 3 to 12 membered aliphatic heterocyclic residue, —X$^7$—R$^{25}$, —X$^8$—Ar$^{13}$, —X$^8$—Ar$^{14}$—Ar$^{13}$, —X$^8$—Ar$^{14}$-R$^{26}$ or —X$^8$—Ar$^{14}$—Ar$^{15}$—R$^{26}$, wherein X$^7$ at each occurrence is independently —O—, —[Z$^{19}$—O]$_c$—, —[O—Z$^{19}$]$_c$—O—, —S—, —[Z$^{19}$—S—]$_c$—, —[S—Z$^{19}$]$_c$—S—, —S(O), —C(O)—, —C(O)O—, —C(O)NR$^{27}$—, C(O)S—, —O(CO)—, —S(CO)—, —NR$^{27}$C(O)— or —NR$^{27}$—, wherein Z$^{19}$ at each occurrence is independently C$_{1-6}$-alkylene, C$_{2-6}$-alkenylene or C$_{1-6}$-haloalkylene, c at each occurrence is independently an integer from 1 to 10 and R$^{27}$ at each occurrence is independently H, C$_{1-20}$-alkyl, or —Z$^{20}$—C$_{6-14}$-aryl, wherein Z$^{29}$ at each occurrence is independently C$_{1-6}$-alkylene, C$_{2-6}$-alkenylene, C$_{1-6}$-haloalkylene or a covalent bond, R$^{25}$ at each occurrence is independently C$_{1-30}$-alkyl, C$_{2-30}$-alkenyl or C$_{1-30}$-haloalkyl, X$^8$ at each occurrence is independently —Z$^{21}$—O—Z$^{22}$—, —Z$^{21}$—S—Z$^{22}$—, —S(O)—, —NR$^{28}$—, —C(O)O—, —(CO)NR$^{28}$, —C(O)S—, —O(CO)—, —S(CO)—, —NR$^{28}$C(O)—, —NR$^{28}$—, —Z$^{21}$—SiR$^{28}_2$—Z$^{22}$—, C$_{1-30}$-alkylene, C$_{2-30}$-alkenylene, C$_{1-30}$-haloalkylene or a covalent bond, wherein Z$^{21}$ and Z$^{22}$ at each occurrence are independently C$_{1-6}$-alkylene, C$_{2-6}$-alkenylene, C$_{1-6}$-haloalkylene or a covalent bond, and R$^{28}$ at each occurrence is independently H, C$_{1-20}$-alkyl, or —Z$^{23}$—C$_{6-14}$-aryl, wherein Z$^{23}$ at each occurrence is independently C$_{1-6}$-alkylene, C$_{2-6}$-alkenylene, C$_{1-6}$-haloalkylene or a covalent bond, Ar$^{12}$ at each occurrence is independently C$_{6-14}$-aryl or monovalent 5 to 14 membered aromatic hetrocyclic residue, each optionally substituted with 1 to 5 substituents R$^o$, wherein each R$^o$ is independently selected from the group consisting of halogen, CN, C$_{1-6}$-alkyl, C$_{1-6}$-alkoxy and C$_{1-6}$-haloalkyl, Ar$^{14}$ and Ar$^{15}$ at each occurrence are independently C$_{6-14}$-arylene or bivalent 5 to 14 membered aromatic heterocyclic residue, each optionally substituted with 1 to 4 substituents R$^p$, wherein each R$^p$ is independently selected from the group consisting of halogen, CN, C$_{1-6}$-alkyl, C$_{1-6}$-alkoxy and C$_{1-6}$-haloalkyl, and R$^{26}$ at each occurrence is independently C$_{1-20}$-alkyl, C$_{2-20}$-alkenyl, C$_{1-20}$-haloalkyl, C$_{1-20}$-alkoxy, —X$^9$—Ar$^{16}$, —X$^9$—Ar$^{17}$—Ar$^{16}$, —X$^9$—Ar$^{17}$—R$^{29}$, or —X$^9$—Ar$^{17}$—Ar$^{18}$—R$^{29}$, wherein X$^9$ at each occurrence is independently —Z$^{24}$—O—Z$^{25}$—, —Z$^{24}$—S—Z$^{25}$—, —S(O)—, —C(O)—, —C(O)O—, —(CO)NR$^{30}$, —C(O)S—, —O(CO)—, —S(CO)—, —NR$^{30}$C(O)—, —NR$^{30}$—, —Z$^{24}$—SiR$^{30}_2$—Z$^{25}$—, C$_{1-30}$-alkylene, C$_{2-30}$-alkenylene, C$_{1-30}$-haloalkylene or a covalent bond, wherein Z$^{24}$ and Z$^{25}$ at each occurrence are independently C$_{1-6}$-alkylene, C$_{2-6}$-alkenylene, C$_{1-6}$-haloalkylene or a covalent bond, and R$^{30}$ at each occurrence is independently H, C$_{1-20}$-alkyl or —Z$^{26}$—C$_{6-14}$-aryl, wherein Z$^{26}$ at each occurrence is independently C$_{1-6}$-alkylene, C$_{2-6}$-alkenylene, C$_{1-6}$-haloalkylene or a covalent bond, Ar$^{16}$ at each occurrence is independently C$_{6-14}$-aryl or monovalent 5 to 14 membered aromatic heterocyclic residue, each optionally substituted with 1 to 5 substituents R$^q$, wherein each R$^q$ is independently selected from the group consisting of halogen, CN, C$_{1-6}$-alkyl, C$_{1-6}$-alkoxy and C$_{1-6}$-haloalkyl, Ar$^{17}$ and Ar$^{18}$ at each occurrence are independently C$_{6-14}$-arylene or bivalent 5 to 14 membered aromatic heterocyclic residue, each optionally substituted with 1 to 4 substituents R$^r$, wherein each R$^r$ is independently selected from the group consisting of halogen, CN, C$_{1-6}$-alkyl, C$_{1-6}$-alkoxy and C$_{1-6}$-haloalkyl, and R$^{29}$ at each occurrence is independently C$_{1-20}$-alkyl, C$_{2-20}$-alkenyl, C$_{1-20}$-haloalkyl or C$_{1-20}$-alkoxy, q and s are the same or different and are 0, 1, 2, 3, 4 or 5, r is 0, 1 or 2, and n is an integer from 1 to 10'000, which process comprises, preferably, (i) the step of reacting a compound of formula

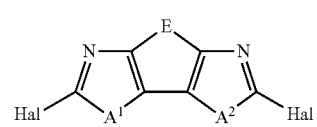

(2)

wherein A$^1$, A$^2$ and E are as defined above, and Hal is halogen, preferably —Br, with a compound of formula

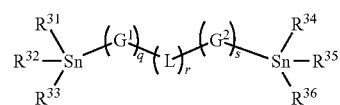

(3)

wherein $G^1$, $G^2$, L, q, r, and s are as defined above, and $R^{31}$, $R^{32}$, $R^{33}$, $R^{34}$, $R^{35}$ and $R^{36}$ are the same and are $C_{1-30}$-alkyl, preferably $C_{1-6}$-alkyl, most preferably n-butyl or methyl,
in the presence of a metal catalyst,
or
(ii) the step of reacting a compound of formula (8)

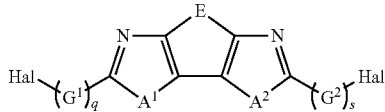

wherein $A^1$, $A^2$ and E, $G^1$, $G^2$, r and s are as defined above, and Hal is halogen, preferably —Br,
with a compound of formula (9)

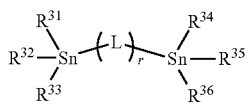

wherein L and r are as defined above, and $R^{31}$, $R^{32}$, $R^{33}$, $R^{34}$, $R^{35}$ and $R^{36}$ are the same and are $C_{1-30}$-alkyl, preferably $C_{1-6}$-alkyl, most preferably n-butyl or methyl,
in the presence of a metal catalyst,
or
(iii) the step of reacting a compound of formula (10)

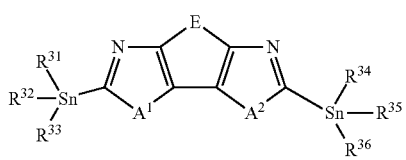

wherein $A^1$, $A^2$ and E are as defined above, and $R^{31}$, $R^{32}$, $R^{33}$, $R^{34}$, $R^{35}$ and $R^{36}$ are the same and are $C_{1-30}$-alkyl, preferably $C_{1-6}$-alkyl, most preferably n-butyl or methyl,
with a compound of formula (11)

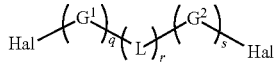

wherein $G^1$, $G^2$, L, q, r, and s are as defined above, and Hal is halogen, preferably —Br,
in the presence of a metal catalyst,
or
(iv) the step of reacting a compound of formula (12)

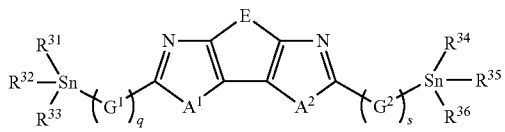

wherein $A^1$, $A^2$, E, $G^1$, $G^2$, r and s are as defined above, and $R^{31}$, $R^{32}$, $R^{33}$, $R^{34}$, $R^{35}$ and $R^{36}$ are the same and are $C_{1-30}$-alkyl, preferably $C_{1-6}$-alkyl, most preferably n-butyl or methyl,
with a compound of formula (13)

wherein L and r are as defined above, and Hal is halogen, preferably —Br,
in the presence of a metal catalyst.

Preferably $R^{31}$, $R^{32}$, $R^{33}$, $R^{34}$, $R^{35}$ and $R^{36}$ are methyl or n-butyl.

The metal catalyst is preferably a palladium catalyst such tris(dibenzylideneacetone)dipalladium(0), preferably in combination with a phosphine such as tri-o-tolylphosphine. The reaction is preferably performed at elevated temperatures such 80 to 200° C., preferably 90 to 150° C. The reaction can be performed in an inert organic solvent such as chlorobenzene. The reaction can be stopped by the addition of end cappers such as 2-bromothiophene and 2-tributylstannylthiophene. The crude product may be worked up by conventional methods, for example by extracting the crude product with an appropriate solvent, for example with acetone.

Alternatively, the compound, oligomer or polymer of formula (1)

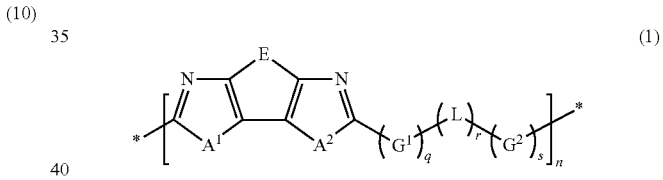

wherein $A^1$, $A^2$, E, $G^1$, L, $G^2$, q, r, s and n are as defined above,
can be prepared by the process as outlined above but using (14)

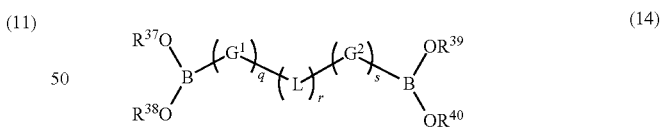

wherein $G^1$, $G^2$, L, q, r, and s are as defined above, and $R^{37}$, $R^{38}$, $R^{39}$ and $R^{40}$ are the same and are H or $C_{1-30}$-alkyl, or $R^{37}$ and $R^{38}$, respectively, $R^{39}$ and $R^{40}$ form together with —O—B—O— a 5 to 8-membered cyclic ring, for example a pinacol type ring of formula (23)

instead of the compound of formula 3,

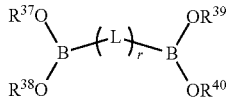
(15)

wherein L and r are as defined above, and $R^{37}$, $R^{38}$, $R^{39}$ and $R^{40}$ are the same and are H or $C_{1-30}$-alkyl, or $R^{37}$ and $R^{38}$, respectively, $R^{39}$ and $R^{40}$ form together with —O—B—O— a 5 to 8-membered cyclic ring, for example a pinacol type ring of formula

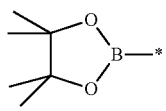
(23)

instead of the compound of formula 9,

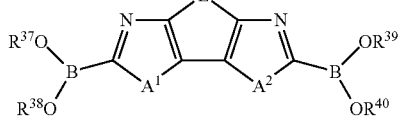
(16)

wherein $A^1$, $A^2$ and E are as defined above, and $R^{37}$, $R^{38}$, $R^{39}$ and $R^{40}$ are the same and are H or $C_{1-30}$-alkyl, or $R^{37}$ and $R^{38}$, respectively, $R^{39}$ and $R^{40}$ form together with —O—B—O— a 5 to 8-membered cyclic ring, for example a pinacol type ring of formula

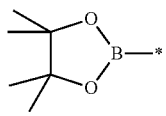
(23)

instead of the compound of formula 10, or

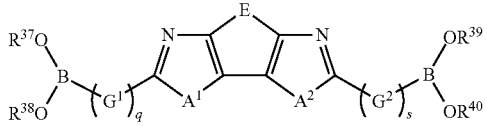
(17)

wherein $A^1$, $A^2$, E, $G^1$, $G^2$, r and s are as defined above, and $R^{37}$, $R^{38}$, $R^{39}$ and $R^{40}$ are the same and are H or $C_{1-30}$-alkyl, or $R^{37}$ and $R^{38}$, respectively, $R^{39}$ and $R^{40}$ form together with —O—B—O— a 5 to 8-membered cyclic ring, for example a pinacol type ring of formula

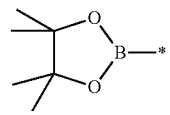
(23)

instead of the compound of formula 12.

The compound of formula

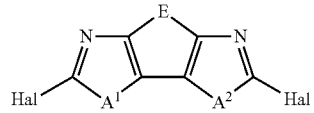
(2)

wherein $A^1$ and $A^2$ are as defined above, and Hal is halogen, preferably —Br, and E is

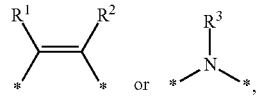

wherein $R^1$, $R^2$ and $R^3$ are as defined above, can be prepared by a process, which comprises the step of reacting a compound of formula

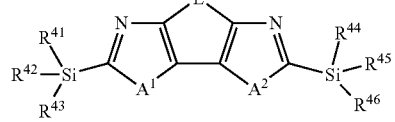
(4)

wherein $A^1$, $A^2$ and E are as defined above, and $R^{41}$, $R^{42}$, $R^{43}$, $R^{44}$, $R^{45}$ and $R^{46}$ are $C_{1-30}$-alkyl, preferably $C_{1-6}$-alkyl, more preferably isopropyl, with a halogenating agent in the presence of an acidic catalyst.

The halogenating agent is preferably —$Br_2$. The acidic catalyst is preferably trichloroacetic acid. The reaction is preferably carried out in an inert organic solvent such as chloroform. The reaction is preferably carried out at ambient temperature, for example at a temperature from 15 to 30° C., more preferably at a temperature from 18 to 26° C. The reaction mixture can be worked up by conventional methods.

The compound of formula

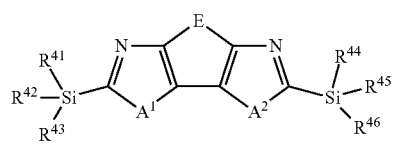
(4)

wherein $A^1$, $A^2$ and E are as defined above, and $R^{41}$, $R^{42}$, $R^{43}$, $R^{44}$, $R^{45}$ and $R^{46}$ are $C_{1-30}$-alkyl, preferably $C_{1-6}$-alkyl, more preferably isopropyl, can be prepared by a process, which comprises the step of coupling a compound of formula

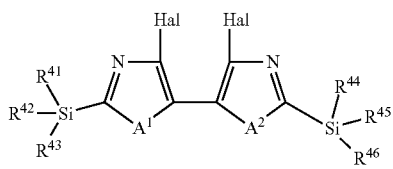

(5)

wherein $A^1$, $A^2$, $R^{41}$, $R^{42}$, $R^{43}$, $R^{44}$, $R^{45}$ and $R^{46}$ are as defined above, and Hal is halogen, preferably —Br, with H-E-H or

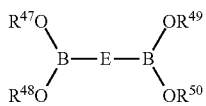

wherein $R^{47}$, $R^{48}$, $R^{49}$ and $R^{50}$ are the same and are H or $C_{1-30}$-alkyl, or $R^{47}$ and $R^{48}$, respectively, $R^{49}$ and $R^{50}$ form together with —O—B—O— a 5 to 8-membered cyclic ring, for example a pinacol type ring of formula.

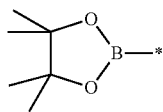

(23)

in the presence of a metal catalyst.

The metal catalyst can be a palladium catalyst such as tetrakis(triphenylphosphine)palladium(0), or tris(dibenzylideneacetone)dipalladium(0) in combination with a phosphine such as rac-BINAP or tri-tert-butylphosphine. Preferably, the reaction is carried out in the presence of a base such as potassium carbonate or sodium tert-butoxide. The reaction can be carried out in an inert organic solvent such as toluene, or in mixtures of inert organic solvents and water, for example in mixtures of toluene and water. The reaction can be carried out at elevated temperatures, for example at a temperature from 70 to 200° C., preferably at a temperature from 80 to 150° C. The reaction mixture can be worked up by conventional methods.

If E is

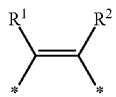

the vic-bis(pinacolatoboryl) complex

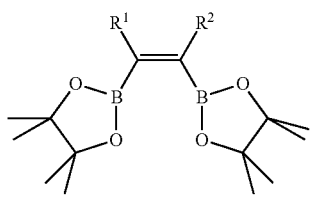

is preferably used in the reaction.

This vic-bis(pinacolatoboryl) complex can be synthesized via platinum catalyzed boronation of

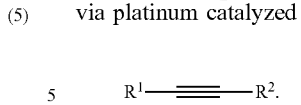

The compound of formula

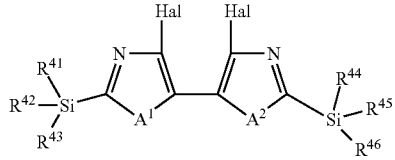

(5)

wherein $A^1$ and $A^2$ are as defined above, $R^{41}$, $R^{42}$, $R^{43}$, $R^{44}$, $R^{45}$ and $R^{46}$ are $C_{1-30}$-alkyl, preferably, $C_{1-20}$-alkyl, preferably $C_{1-6}$-alkyl, more preferably isopropyl, and Hal is halogen, preferably —Br,
can be prepared by a process which comprises the step of reacting

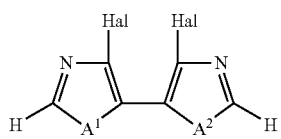

(6)

wherein $A^1$ and $A^2$ are as defined above, and Hal is halogen, preferably —Br, with $R^{41}R^{42}R^{43}$Si-Hal and $R^{44}R^{45}R^{46}$Si-Hal and a base, wherein $R^{41}$, $R^{42}$, $R^{43}$, $R^{44}$, $R^{45}$ and $R^{46}$ are as defined above, and Hal is halogen, preferably —Br.

An example of a base is lithium diisopropylamide. The reaction can be performed in an inert organic solvent, for example THF. The reaction can be performed at a temperature of 0 to −100° C., preferably at −40 to −90° C., preferably at around −78° C. The reaction mixture obtained can be worked-up by conventional methods.

The compound of formula

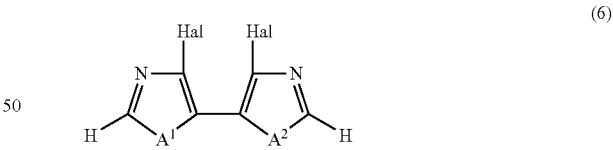

(6)

wherein $A^1$ and $A^2$ are as defined above, and Hal is halogen, preferably —Br,
can be prepared by a process comprising the step of reacting

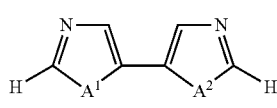

(7)

wherein $A^1$ and $A^2$ are as defined above,
with a halogenating agent.

An example of a halogenating agent is N-bromosuccinimide. The reaction can be performed in an inert organic solvent, for example DMF. The reaction can be performed at elevated temperature, for example at a temperature from 20 to 100° C., preferably at 40 to 80° C. The reaction mixture obtained can be worked-up by conventional methods.

A compound of formula 2d can also be prepared via thiocyanation of 2,6-diamino-benzothiazole 18 as reported by Landquist, J. K. *J. Chem. Soc. C* 1967, 2212 to 2220, followed by Sandmeyer reaction as depicted below

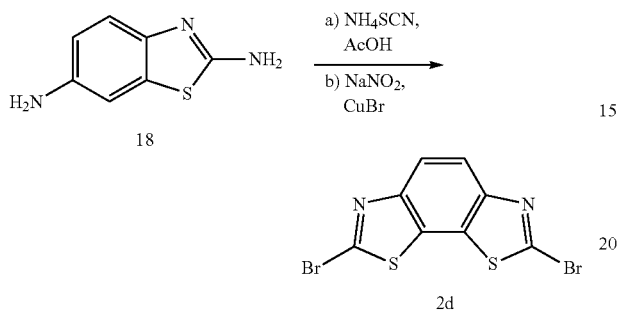

A compound of formula 2e can also be prepared via condensation of 3,6-diamino-1,2-phenylene dihydrogen thiosulphate 19 with thiophene-2-carboxylic acid in analogy to the processes described by Green, A. G. *J. Chem. Soc., Trans.* 1903, 83, 1201 to 1212, and by Cox, R. J.; Clecak, N. J. *J. Org. Chem.* 1968, 33, 2132 to 2133, followed by halogenation as depicted below

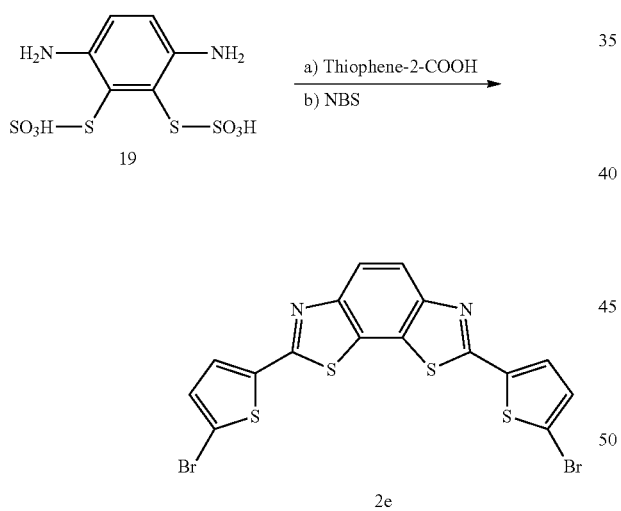

The compound of formula

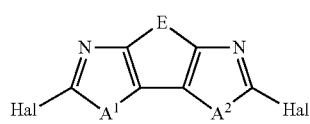

wherein A¹ and A² are as defined above, and Hal is halogen, preferably —Br, and E is selected from the group consisting of

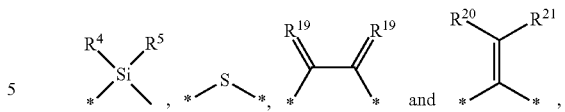

wherein R⁴, R⁵, R¹⁹, R²⁰ and R²¹ are as defined above, can be prepared by a process, which comprises the step of reacting a compound of formula

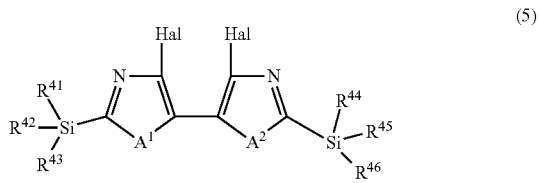

wherein A¹ and A² are as defined above, R⁴¹, R⁴², R⁴³, R⁴⁴, R⁴⁵ and R⁴⁶ are C₁₋₃₀-alkyl, preferably C₁₋₆-alkyl, more preferably isopropyl, and Hal is halogen, preferably —Br, with a suitable compound to incorporate E, in the presence of a base such as butyl lithium.

For example, the compounds of formulae 2f, 2g, 2h and 2i can be prepared as follows:

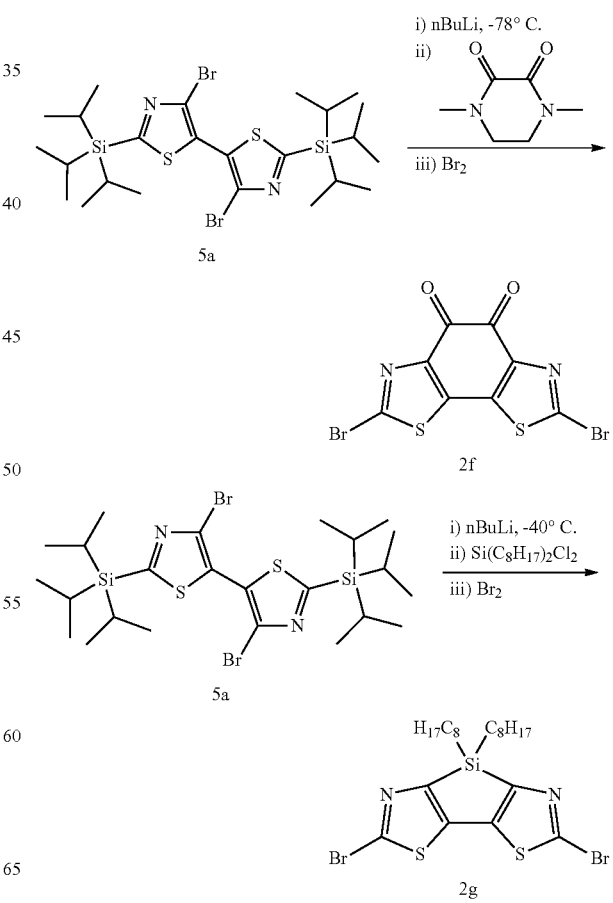

-continued

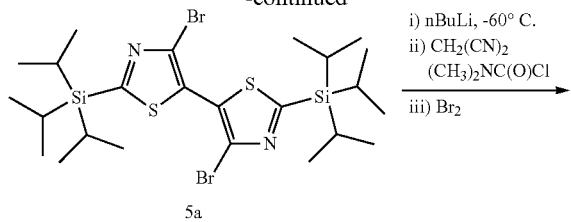

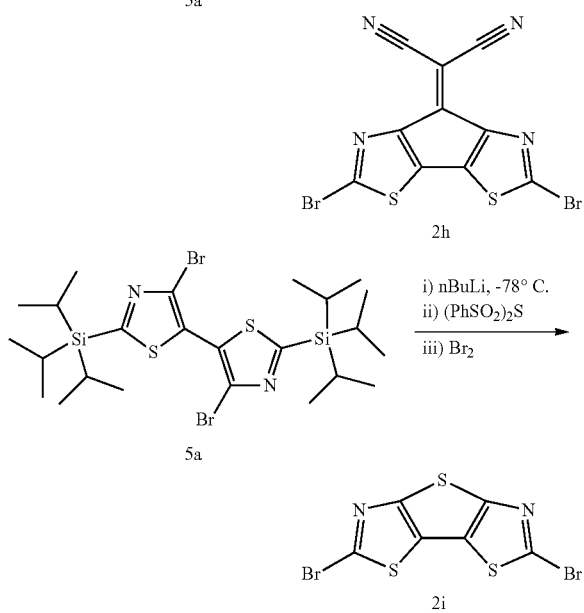

The compound of formula

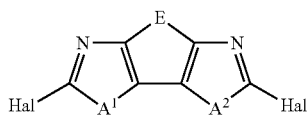

(2)

wherein $A^1$ and $A^2$ are as defined above, and Hal is halogen, preferably —Br, and E is selected from the group consisting of

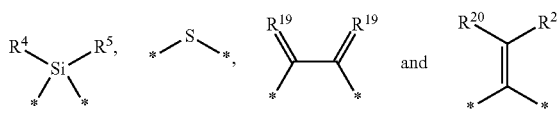

wherein $R^4$, $R^5$, $R^{19}$, $R^{20}$ and $R^{21}$ are as defined above, can also be prepared by a process, which comprises the step of reacting a compound of formula

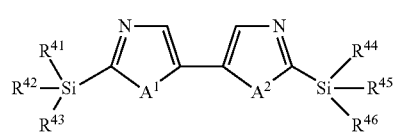

(20)

wherein $A^1$ and $A^2$ are as defined above, $R^{41}$, $R^{42}$, $R^{43}$, $R^{44}$, $R^{45}$ and $R^{46}$ are $C_{1-30}$-alkyl, preferably $C_{1-6}$-alkyl, more preferably isopropyl, with a suitable compound to incorporate E, in the presence of a base such as lithium diisopropylamide, for example as described for similar compounds in WO 2009/069687.

The compound of formula

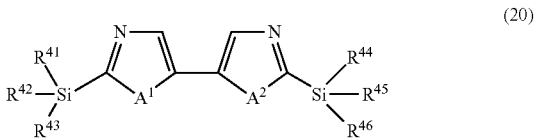

(20)

wherein $A^1$ and $A^2$ are as defined above, $R^{41}$, $R^{42}$, $R^{43}$, $R^{44}$, $R^{45}$ and $R^{46}$ are $C_{1-30}$-alkyl, preferably $C_{1-6}$-alkyl, more preferably isopropyl, can be prepared via oxidative coupling of

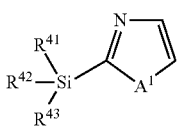

(21)

For example the compound of formula 20a can be prepared as follows:

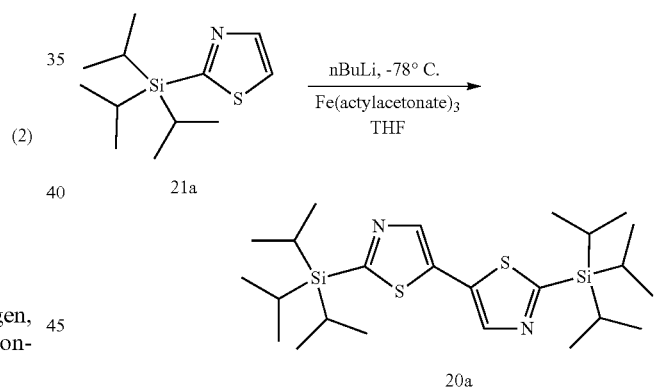

The compound of formula

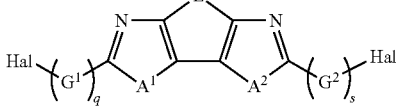

(8)

wherein $A^1$ and $A^2$ can be the same or different and are S or Se,

E is selected from the group consisting of

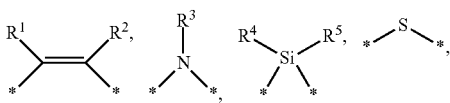

-continued

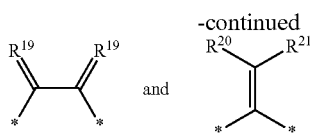
and wherein $R^1$, $R^2$, $R^3$, $R^4$, $R^5$, $R^{19}$, $R^{20}$ and $R^{21}$ are as defined above, $G^1$ and $G^2$ are as defined above, q and s are as defined above, and Hal is halogen, can be prepared by reacting the compound of formula

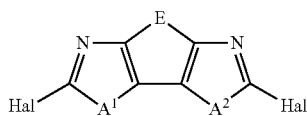 (2)

wherein $A^1$ and $A^2$ are as defined above, and Hal is halogen, with suitable compounds to incorporate $G^1$ and $G^2$, such as stannyl functionalized $G^1$ and $G^2$ or borate functionalized $G^1$ or $G^2$ or Grignard functionalized $G^1$ and $G^2$, in the presence of a metal catalyst, followed by halogenation.

For example, the compound of formula 8a can be prepared as follows:

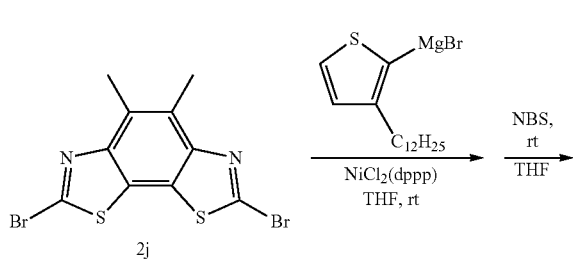

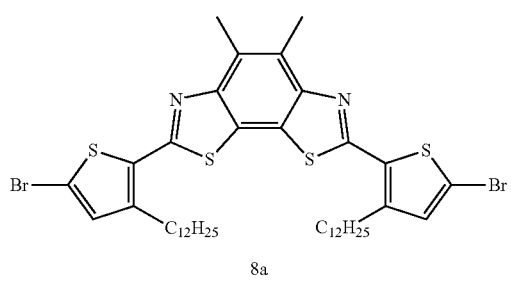

8a

Also part of the invention is the compound of formula

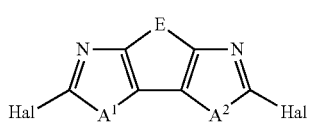 (2)

wherein $A^1$ and $A^2$ can be the same or different and are S or Se,

E is selected from the group consisting of

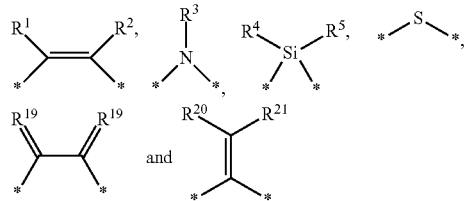

and wherein $R^1$, $R^2$, $R^3$, $R^4$, $R^5$, $R^{19}$, $R^{20}$ and $R^{21}$ are as defined above and Hal is halogen.

Also part of the invention is the compound of formula (4)

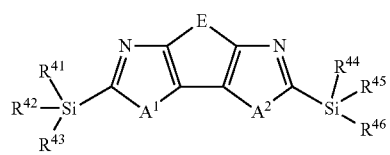

wherein $A^1$ and $A^2$ can be the same or different and are S or Se,

E is

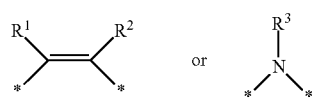

and $R^{41}$, $R^{42}$, $R^{43}$, $R^{44}$, $R^{45}$ and $R^{46}$ are $C_{1-30}$-alkyl, preferably $C_{1-6}$-alkyl, more preferably isopropyl.

Also part of the invention is a compound of formula (5)

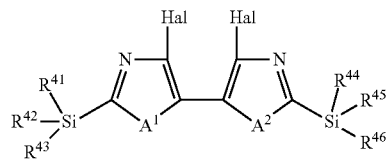

wherein $A^1$ and $A^2$ can be the same or different and are S or Se, $R^{41}$, $R^{42}$, $R^{43}$, $R^{44}$, $R^{45}$ and $R^{46}$ are $C_{1-30}$-alkyl, preferably $C_{1-6}$-alkyl, more preferably isopropyl, and Hal is halogen, preferably —Br.

Also part of the present invention is an electronic device comprising the compounds, oligomers and polymers of the present invention.

The electronic device can be any electronic device, for example an organic photovoltaic (OPV) cell, an organic field-effect transistor (OFET) or an organic light emitting diode (OLED). Preferably, it is an organic field-effect transistor.

The organic field effect transistor comprising the compounds, oligomers and polymers of the present invention can be prepared by solution deposition of a solution of the compounds, oligomers and polymers of the present invention in a suitable solvent. The solvent can be an organic solvent, for example 1,2-dichlorobenzene. Solution deposition can be performed by methods known in the art, for example by spin coating, for example at 2000 rpm, 255 acc (acc: spin acceleration), 1 minute.

The organic field effect transistor can have any architecture known in the art, for example a bottom gate bottom contact (BGBC) architecture as depicted in FIG. 1. When the organic field effect transistor has a bottom gate bottom contact (BGBC) architecture, the substrate (or gate electrode), the gate dielectric, and the source and drain electrodes can be any substrate, gate dielectric, source and drain electrode known in the art. For example, the substrate (or gate electrode) can be heavily doped silicon wafer, the gate dielectric can be thermally grown silica, and the source and drain electrode can be made of gold which is lithographically patterned. Before deposition of the compounds, oligomers and polymers of the present invention as semiconductors, the device can be vapor treated with hexamethyldisilazane (HMDS).

Also part of the invention is the use of the compound, oligomer or polymer of the present invention as organic semiconducting material.

The compounds, oligomers and polymers of the present invention show a surprising high ionization potential, which may contribute to better ambient oxidative stability. The compounds, oligomers and polymers of the present invention are compatible with liquid processing techniques and are suitable for use as semiconductors in organic field effect transistors. The organic field effect transistor using the compounds, oligomers and polymers of the present invention as semiconductors show good field-effect mobilities and on/off ratios.

FIG. 1 shows an organic field effect transistor having a bottom gate bottom contact (BGBC) architecture.

EXAMPLES

Example 1

Preparation of 2,2'-dibromo-(5,6-dihexylbenzo[2,1-d;3,4-d']bisthiazole) (2a)

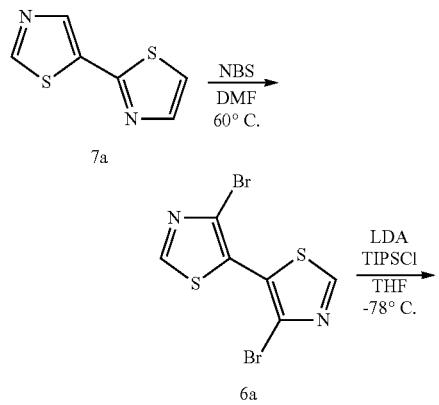

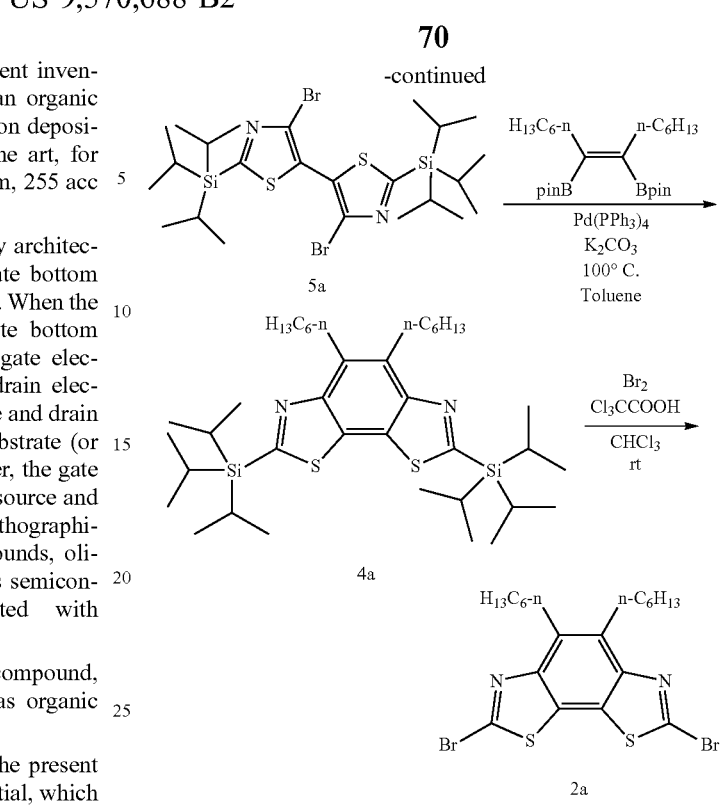

Preparation of 4,4'-dibromo-5,5'-bithiazole (6a)

N-bromosuccinimide (6.35 g, 35.66 mmol, 4 eq.) is added to a stirred homogeneous solution of 5,5'-bithiazole (7a) (1.5 g, 8.9 mmol) in anhydrous DMF (125 mL). The reaction mixture is heated at 60° C. for 3 hours. The reaction mixture is washed subsequently with an aqueous solution of 10% sodium bicarbonate (200 mL), extracted with dichloromethane (200 mL), washed with water (3×100 mL) and sodium chloride saturated water (100 mL), and dried over anhydrous sodium sulfate. The crude product is re-crystallized from dichloromethane/n-hexane (1:10). Yellowish crystals are obtained. $^1$H-NMR (d-chloroform) (400 MHz): δ 8.87 (s, 2H). $^{13}$C-NMR (d-chloroform) (400 MHz): δ 154.8, 129.3, 122.5.

Preparation of 2,2'-bis(triisopropylsilyl)-4,4'-dibromo-5,5'-bithiazole (5a)

1.84 mL of a 2M solution of lithium diisopropylamide (0.39 g, 3.68 mmol, 2.4 eq.) in THF is added dropwise to a solution of 4,4'-dibromo-5,5'-bithiazoles (6a) (0.5 g, 1.53 mmol) in anhydrous THF (20 mL) at −78° C. over 10 minutes. The reaction mixture is allowed to stir for 3 hours, and then triisopropylsilyl chloride (0.709 g, 0.79 mL, 3.68 mmol, 2.4 eq.) is added slowly. The reaction mixture is warmed up to room temperature overnight. The reaction mixture is diluted with ethyl acetate (140 mL), and the organic layer is washed with sodium bicarbonate saturated water (70 mL) and sodium chloride saturated water (70 mL), dried over magnesium sulfate and concentrated in vacuo. Column chromatography using gradient solvent from n-hexane to ethyl acetate/n-hexane (5/95) provides a yellow solid. $^1$H-NMR (d-chloroform) (400 MHz): δ 2.43-1.5 (m, J=8 Hz, 6H), δ 1.16-1.18 (d, J=7.6 Hz, 36H). $^{13}$C-NMR (d-chloroform) (400 MHz): δ 172.7, 130.5, 125.1, 18.7, 11.8.

Preparation of 2,2'-bis(triisopropylsilyl)-(5,6-dihexylbenzo[2,1-d;3,4-d']bisthiazole) (4a)

A mixture of 5a (0.5 g, 0.783 mmol) and tetrakis(triphenylphosphine)palladium(0) (0.090 g, 0.078 mmol, 0.1 eq.) is degassed 3 times. A solution of vic-bis(pinacolatoboryl)-7-tetradecene (0.456 g, 1.018 mmol, 1.3 eq.), in anhydrous toluene (5 mL) is added, followed by 12 mL of toluene (total 17 mL anhydrous toluene). Subsequently 2.8 mL of degassed aqueous solution of potassium carbonate (0.64 g, 4.70 mmol, 6 eq.) is added. The reaction mixture is stirred and heated at 100° C. overnight. The reaction mixture is allowed to cool to room temperature, and is diluted with ethyl acetate (50 mL). The resulting reaction mixture is washed with ammonium chloride saturated water (50 mL) and the aqueous layer is extracted with ethyl acetate (3×50 mL). The combined organic layers are washed with sodium chloride saturated water (25 mL), dried over magnesium sulfate, and concentrated in vacuo. Column chromatography using a gradient solvent from n-hexane to ethyl acetate/n-hexane (10/90) provides an off-white solid. $^1$H-NMR (d-chloroform) (400 MHz): δ 3.37 (dd, J=8 Hz, 4H), δ 1.74-1.76 (m, J=8 Hz, 4H), δ 1.47-1.55 (m, J=8 Hz, 6H), δ 1.33-1.37 (m, J=8 Hz, 12H), δ 1.2-1.22 (d, J=8 Hz, 36H), δ 0.87-0.92 (t, J=7.6 Hz, 6H). LC-MS: 95% purity with m/z 673.4.

Preparation of 2,2'-dibromo-(5,6-dihexylbenzo[2,1-d;3,4-d']bisthiazole) (2a)

A solution of bromine (0.34 g, 0.11 mL, 2.11 mmol, 4 eq.) in chloroform (5 mL) containing trichloroacetic acid (7 mg) is added dropwise and slowly to a solution of 4a (0.355 g, 0.527 mmol) in chloroform (8 mL) at 0° C. The reaction mixture is stirred at room temperature for 3 days. The reaction mixture is diluted with dichloromethane (50 mL), washed with an aqueous solution of 20 weight % sodium thiosulfate (50 mL) and with an aqueous solution of 10 weight % sodium bicarbonate (50 mL). Subsequently the organic layer is dried over magnesium sulfate and concentrated in vacuo. Purification by column chromatography (ethyl acetate/n-hexane (10/90)) followed by re-crystallisation from ethanol affords light brown crystals. $^1$H-NMR (d-chloroform) (400 MHz): δ 3.17 (dd, J=8 Hz, 4H), δ 1.66 (m, J=8 Hz, 4H), δ 1.47 (m, J=8 Hz, 4H), δ 1.35 (m, J=8 Hz, 8H), δ 0.92 (t, J=7.6 Hz, 6H). LC-MS: 98% purity with m/z 519. Elemental analysis (calcd): C, 46.34 (46.36); H, 5.06 (5.09).

Example 2

Preparation of poly(benzobisthiazole-cyclopentadithiophene) (1a)

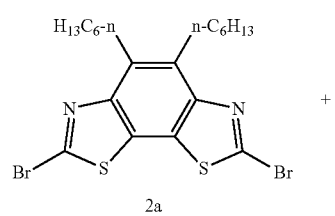

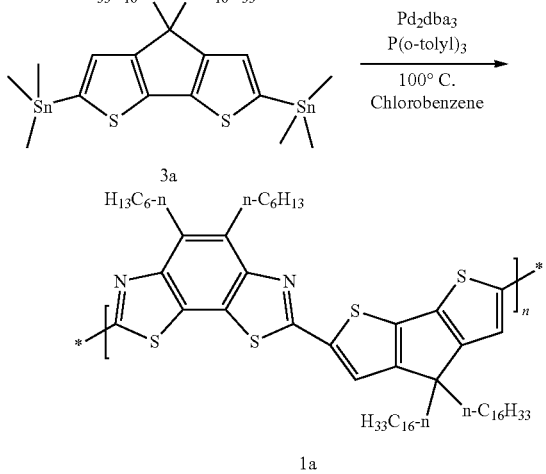

Dibromo-benzobisthiazole (2a) (60 mg, 0.116 mmol, 1 eq.), bis(trimethylstannyl)cyclopentadithiophene (3a) (110 mg, 0.116 mmol, 1 eq.), tris(dibenzylidene-acetone)dipalladium(0) (3.2 mg, 0.003 mmol, 3% eq.) and tri-o-tolylphosphine (2.1 mg, 0.007 mmol, 6% eq.) are added into a Schlenk flask and degassed 3 times. Chlorobenzene (4 mL) is added and the reaction mixture is stirred at 100° C. overnight then at 130° C. for 2 days. 2-Bromothiophene (0.01 mL) and 2-tributylstannylthiophene (0.01 mL) are added as end cappers, with 2-bromothiophene added first followed by 2-tributylstannylthiophene 2 hours later. After another 2 hours stirring, the reaction mixture is cooled to room temperature. The reaction mixture is then added dropwise to methanol (200 mL), filtered, and then subjected to Soxhlet extraction with acetone. The polymer is recovered as solid mass and showed Mn=8360 g/mol (Mw=24264 g/mol & PDI=2.92). Elemental analysis (calcd): C, 70.77 (74.48); H, 8.93 (9.63).

Example 3

Preparation of poly(benzobisthiazole-bisthienylethylene) (1b)

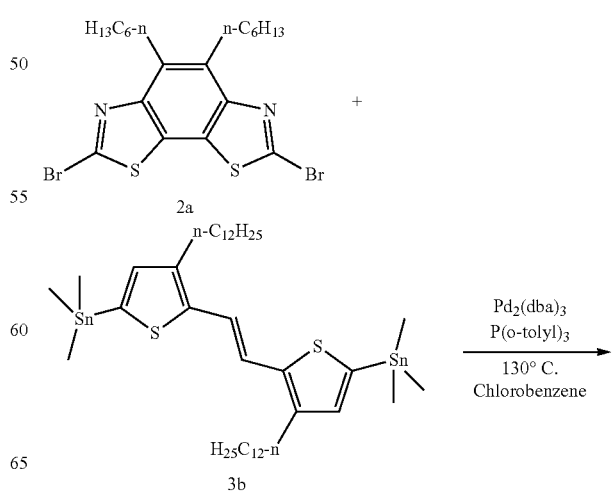

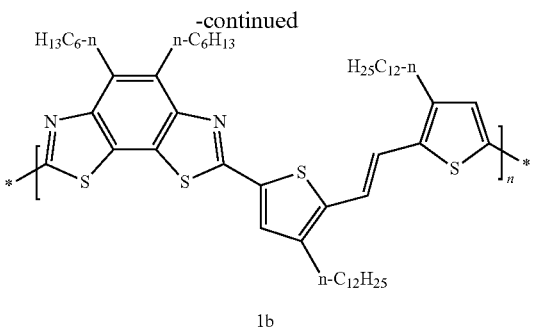

1b

Dibromo-benzobisthiazole (2a) (55 mg, 0.106 mmol, 1 eq.) prepared as described in example 1, bis(2-trimethylstannyl-4-dodecylthienyl)ethylene (3b) (90.7 mg, 0.106 mmol, 1 eq.), tris(dibenzylideneacetone)dipalladium(0) (2.9 mg, 0.003 mmol, 3% eq.) and tri-o-tolylphosphine (1.9 mg, 0.006 mmol, 6% eq.) are added into a Schlenk flask and degassed 3 times. Chlorobenzene (2 mL) is added and the reaction mixture is stirred at 130° C. for 2 days. 2-Bromothiophene (0.01 mL) and 2-tributylstannylthiophene (0.01 mL) are added as end cappers, with 2-bromothiophene added first followed by 2-tributylstannylthiophene 2 hours later. After another 2 hours stirring, the reaction mixture is cooled to room temperature. The mixture is filtered and the filtrate is concentrated and added dropwise to methanol (200 mL), filtered, and then subjected to Soxhlet extraction with acetone. The polymer is recovered as solid mass and showed Mn=3368 g/mol (Mw=4749 g/mol & Đ=1.41).

Example 4

Preparation of poly(benzobisthiazole-bithiophene) (1c)

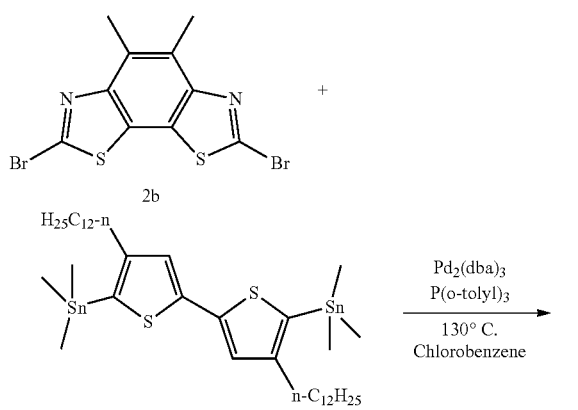

Preparation of 2,2'-dibromo-(5,6-dimethylbenzo[2,1-d;3,4-d']bisthiazole) (2b)

Dibromo-benzobisthiazole (2b) is prepared in analogy to 2,2'-dibromo-(5,6-dihexylbenzo[2,1-d;3,4-d']bisthiazole) (2a) in example 1, except that vic-bis(pinacolatoboryl)-2-butene (with the equivalent of 1.3 eq to the substrate 5a) is used instead of vic-bis(pinacolatoboryl)-7-tetradecene (with the equivalent of 1.3 eq to the substrate 5a).

Preparation of poly(benzobisthiazole-bithiophene) (1c)

Dibromo-benzobisthiazole (2b) (79 mg, 0.209 mmol, 1 eq.) is added as a 4.2 mL chlorobenzene solution into a pre-degassed mixture of bis(2-trimethylstannyl-2-dodecylthiophene) (3c) (173.1 mg, 0.209 mmol, 1 eq.), tris(dibenzylideneacetone)dipalladium(0) (5.7 mg, 0.003 mmol, 3% eq.) and tri-o-tolylphosphine (3.8 mg, 0.006 mmol, 6% eq.). The reaction mixture is stirred at 130° C. for 2 days. After two days of reaction, tris(dibenzylideneacetone)-dipalladium(0) (5.7 mg, 0.003 mmol, 3% eq.) and tri-o-tolylphosphine (3.8 mg, 0.006 mmol, 6% eq.) is added. After four days of reaction, another portion of tris(dibenzylidene-acetone)dipalladium(0) (5.7 mg, 0.003 mmol, 3% eq.) and tri-o-tolylphosphine (3.8 mg, 0.006 mmol, 6% eq.) is added. After total 6 days, the polymerization is stopped by the addition of 2-bromothiophene (0.01 mL) and 2-tributylstannylthiophene (0.01 mL). 2-Bromothiophene is added first followed by 2-tributylstannylthiophene 4 hours later. After another 24 hours stirring, the reaction mixture is cooled to room temperature. The mixture is filtered and the filtrate is concentrated and added dropwise to a methanolic solution of 5 weight % HCl (200 mL). The polymer is filtered and before soxhlet extraction in acetone showed Mn=959 g/mol (Mw=1410 g/mol & Đ=1.47).

Example 5

Preparation of N-4-decylaniline-2,6-dibromo dithiazolo[2,3-d;3',2'-b]pyrrole (2c)

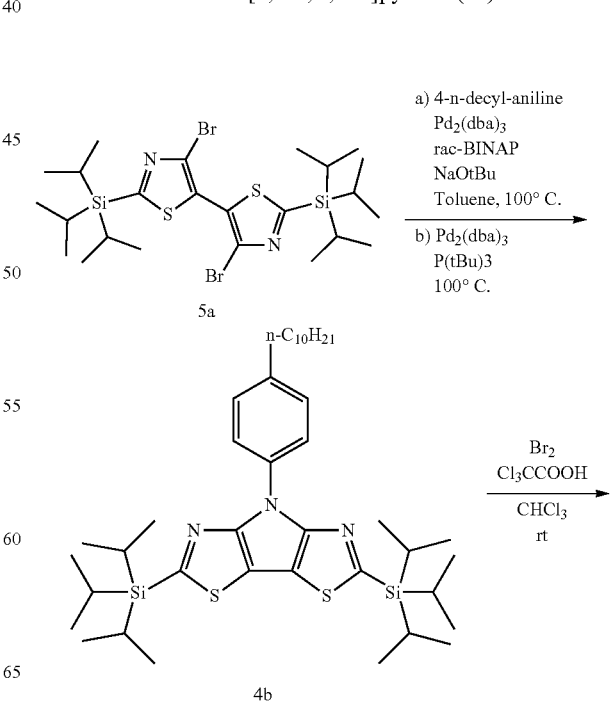

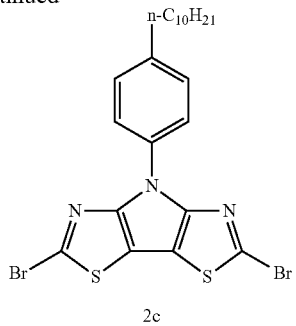

2c

Preparation of N-4-decylaniline-2,6-bis(triisoproyl-silyl)dithiazolo[2,3-d;3',2'-b]pyrrole) (4b)

A mixture of bis(triisopropylsilyl)-dibromobithiazole (5a) (790 mg, 1.237 mmol), tris(dibenzylideneacetone)dipalladium(0) (113 mg, 0.123 mmol, 0.1 eq.), sodium tert-butoxide (200 mg, 2.968 mmol, 2.4 eq.) and rac-BINAP (153 mg, 0.347 mmol, 0.2 eq.) is degassed 3 times. 4-n-Decylaniline (360 mg, 1.546 mmol, 1.25 eq.) in anhydrous toluene (18 mL) is added. The reaction mixture is stirred and heated at 100° C. for 2 days under nitrogen. After the mono-aminated intermediate is formed tris(dibenzylidene-acetone)dipalladium(0) (56 mg, 0.061 mmol, 0.05 eq.) and 0.36 mL of a 10 weight % solution of tri-tert-butylphosphine (24 mg, 0.173 mmol, 0.1 eq.) in n-hexane is added. The reaction mixture is stirred at 100° C. for 2 days under nitrogen. Afterwards the reaction mixture is diluted with ethyl acetate (100 mL). The resulting reaction mixture is washed with ammonium chloride saturated water (100 mL) and the aqueous layer is extracted with ethyl acetate (3×70 mL). The combined organic layers are washed with sodium chloride saturated water (50 mL), dried over magnesium sulfate, and concentrated in vacuo. Column chromatography using ethyl acetate/n-hexane (2/98) provided off-white solid. $^1$H-NMR (d-chloroform) (400 MHz): δ 8.58 (d, J=9.6 Hz, 2H), δ 7.34 (d, J=8.4 Hz, 2H), δ 2.28 (dd, J=8 Hz, 2H), δ 1.65 (m, J=8 Hz, 2H), δ 1.52-1.46 (m, J=8 Hz, 6H), δ 1.27 (s, 14H), δ 1.19-1.21 (d, J=8 Hz, 36H), δ 0.88 (t, J=7.6 Hz, 3H).

Preparation of N-4-decylaniline-2,6-dibromo dithiazolo[2,3-d;3',2'-b]pyrrole (2c)

A solution of bromine (0.16 g, 0.05 mL, 1.01 mmol, 4 eq.) in chloroform (3 mL) containing trichloroacetic acid (4 mg) is slowly and dropwise added to a solution of 4b (0.180 g, 0.253 mmol) in chloroform (4 mL) at 0° C. The reaction mixture is stirred at room temperature for 2 days. The reaction mixture is diluted with dichloromethane (50 mL), washed with an aqueous solution of 20 weight % sodium thiosulfate (50 mL) and an aqueous solution of 10 weight % sodium bicarbonate (50 mL). Subsequently the organic layer is dried over magnesium sulfate and concentrated in vacuo. Purification by column chromatography using n-hexane followed by re-crystallisation from n-hexane affords white flakes. $^1$H-NMR (d-chloroform) (400 MHz): δ 7.88 (d, J=8.4 Hz, 2H), δ 7.35 (d, J=8 Hz, 2H), δ 2.66 (dd, J=7.6 Hz, 2H), δ 1.63 (m, J=7.6 Hz, 2H), δ 1.28 (s, 14H), δ 0.88 (t, J=7.6 Hz, 3H). LC-MS: 97.2% purity with m/z 556. Elemental analysis (calcd): C, 47.54 (47.58); H, 4.46 (4.54).

Example 6

Preparation of poly(dithiazolopyrrole-bisthienylethylene) (1d)

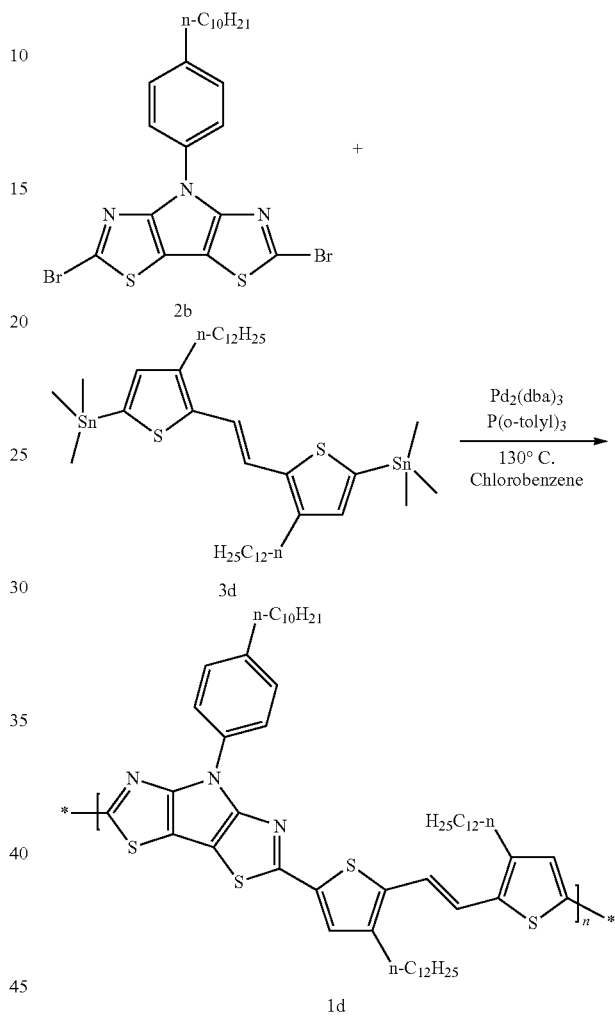

Dibromo-dithiazolopyrrole (2c) (36 mg, 0.065 mmol, 1 eq.) prepared as described in example 5, bis(2-trimethylstannyl-4-dodecylthienyl)ethylene (3d) (55.4 mg, 0.065 mmol, 1 eq.), tris(dibenzylideneacetone)dipalladium(0) (3.6 mg, 0.004 mmol, 6% eq.) and tri-o-tolylphosphine (2.4 mg, 0.008 mmol, 12% eq.) are added into a Schlenk flask and degassed 3 times. Chlorobenzene (1.5 mL) is added and the reaction mixture is stirred at 130° C. for 2 days. After two days of reaction, tris(dibenzylideneacetone)dipalladium(0) (3.6 mg, 0.004 mmol, 6% eq.) and tri-o-tolylphosphine (2.4 mg, 0.008 mmol, 12% eq.) was added. After total reaction of 3 days, the polymerization is stopped by the addition of 2-bromothiophene (0.01 mL) followed by 2-tributylstannyl-thiophene (0.01 mL) 3 hours later. After another 3 hours stirring, the reaction mixture is cooled to room temperature and added dropwise to methanol (100 mL), filtered, and then subjected to Soxhlet extraction with acetone. The polymer is recovered as solid mass and showed Mn=4305 g/mol (Mw=7571 g/mol & Đ=1.76).

Measurement of the Ionization Potential of Polymer 1a

The oxidative stability of π-conjugated polymers may be contributed by their ionization potential (IP), that is, on the energy of the highest occupied molecular orbital (HOMO) with respect to vacuum. The ionization potential (IP) is also reflected as negative value of the HOMO energy level ($E_{HOMO}$) of a molecule, oligomer or polymer, $$IP = -E_{HOMO}$$

and can be measured by cyclic voltammetry (CV).

The HOMO energy levels ($E_{HOMO}$) of poly(benzobisthiazole-cyclopentadithiophene) (1a), prepared as described in example 2, and comparative polymer 22a, which is described by Xiao, S; Zhou H.; You, W. in *Macromolecules* 2008, 41, 5688-5696, are determined by cyclic voltammetry (CV).

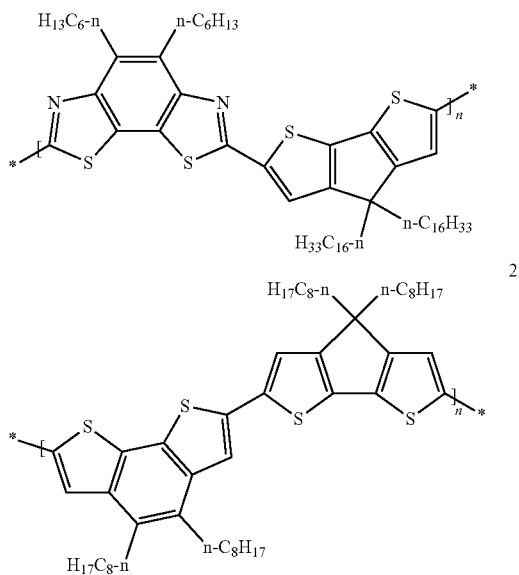

Cyclic voltamogramms are recorded from thin films of polymer 1a, respectively comparative polymer 22a, dropcasted from 0.5 mg/mL chloroform solutions. A Pt disk is used as a working electrode and Ag/AgCl reference electrode is employed. The measurement is done in tetrabutylammonium tetrafluoroborate as electrolyte and ferrocene/ferrocenium redox couple (Fc/Fc$^+$) is used as an internal reference, which has a known reduction potential of 4.8 eV. The electrochemical (oxidation and reduction) onset is determined at the position where the current starts to differ from the baseline and the HOMO energy level ($E_{HOMO}$) is calculated from the onset oxidation potential ($E_{Ox}$), as shown in the equation below:

$$E_{HOMO} = -(E_{Ox} + 4.8) [eV]$$

The results are outlined in table 1.

TABLE 1

| polymer | $E_{HOMO}$ [eV] |
| --- | --- |
| 1a | −5.44 |
| 22a (comparative) | −5.04 |

As can be derived from table 1, the HOMO energy level ($E_{HOMO}$) value of polymer 1a is decreased by 0.4 eV compared to the HOMO energy level ($E_{HOMO}$) value of comparative polymer 22a, and thus the ionization potential (IP) and consequently the oxidative stability of polymer 1a is higher than the one of comparative polymer 22a.

Fabrication of an Organic Field-Effect Transistor Using Polymer 1a as Semiconductor An organic field effect transistor is made in bottom gate bottom contact (BGBC) architecture, as depicted in FIG. 1. Heavily doped Si wafer are used as substrate and gate electrode with 200 nm thermally grown SiO$_2$ serving as gate dielectric. Source and drain electrode are made of gold which is lithographically patterned. Before semiconductor deposition, the substrate is vapor treated with hexamethyldisilazane (HMDS). The polymer 1a solution is prepared by solubilizing the polymer 1a in 1,2-dichlorobenzene and heating it inside oven until soluble. Subsequently, semiconductor solution deposition of the polymer 1a is done by spin coating (deposition condition: 2000 rpm, 255 acc, 1 minute). The organic field effect transistor is made in ambient environment.

Testing of the Organic Field-Effect Transistor Using Polymer 1a as Semiconductor The hole mobility ($\mu_p$), onset voltage ($V_{on}$, voltage when the drain current increases abruptly and can be measured), and the on/off ratio of the organic field effect transistor using polymer 1a as semiconductor are determined at room temperature and after annealing at 200° C. for 30 minutes, in order to observe the effect of annealing on the semiconductor performance. The organic field effect transistor is tested in ambient environment. Channel length (L)=5 μm, Channel width (W)=350 μm, W/L=70. Measurement is performed at: gate voltage (Vg)=sweep from 20 to −90 V, drain voltage (Vd)=−90 V, The results are outlined in table 2.

TABLE 2

| | hole mobility $\mu_p$ [cm$^2$/Vs] | $V_{on}$ [V] | On/Off ratio |
| --- | --- | --- | --- |
| at RT | 0.2 × 10$^{-3}$ | −5 | 2.66 × 10$^4$ |
| after annealing at 200° C. | 1.06 × 10$^{-3}$ | 5 | 6.01 × 10$^4$ |

The invention claimed is:
1. An oligomer or polymer of formula

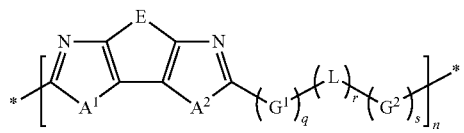

wherein
A$^1$ and A$^2$ can be the same or different and are S or Se,
E is selected from the group consisting of

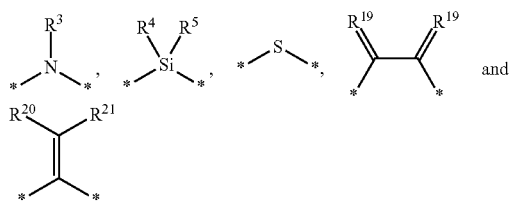

wherein
$R^1$ is H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^1$—$R^6$, —$X^2$—$Ar^1$, —$X^2$—$Ar^2$—$Ar^1$, —$X^2$—$Ar^2$—$R^7$ or —$X^2$—$Ar^2$—$Ar^3$—$R^7$,
wherein
$X^1$ at each occurrence is independently —O—, —[$Z^1$—O]$_a$—, —[O—$Z^1$]$_a$—O—, —S—, —[$Z^1$—S—]$_a$—, [S—$Z^1$]$_a$—S—, —S(O), —C(O)—, —C(O)O—, —C(O)NR$^8$—, C(O)S—, —O(CO)—, —S(CO)—, —NR$^8$C(O)— or —NR$^8$—,
wherein
$Z^1$ at each occurrence is independently $C_{1-6}$-alkylene, $C_{2-6}$-alkenylene or $C_{1-6}$-haloalkylene,
a at each occurrence is independently an integer from 1 to 10 and
$R^8$ at each occurrence is independently H, $C_{1-20}$-alkyl, or —$Z^2$—$C_{6-14}$-aryl,
wherein
$Z^2$ at each occurrence is independently $C_{1-6}$-alkylene, $C_{2-6}$-alkenylene, $C_{1-6}$-haloalkylene or a covalent bond,
$R^6$ at each occurrence is independently $C_{1-30}$-alkyl, $C_{2-30}$-alkenyl or $C_{1-30}$-haloalkyl,
$X^2$ at each occurrence is independently —$Z^3$—O—$Z^4$—, —$Z^3$—S—$Z^4$—, —S(O)—, —C(O)—, —C(O)O—, —(CO)NR$^9$, —C(O)S—, —O(CO)—, —S(CO)—, —NR$^9$C(O)—, —NR$^9$—, —$Z^3$—SiR$^9$$_2$—$Z^4$—, $C_{1-30}$-alkylene, $C_{2-30}$-alkenylene, $C_{1-30}$-haloalkylene or a covalent bond,
wherein
$Z^3$ and $Z^4$ at each occurrence are independently $C_{1-6}$-alkylene, $C_{2-6}$-alkenylene, $C_{1-6}$-haloalkylene or a covalent bond, and
$R^9$ at each occurrence is independently H, $C_{1-20}$-alkyl, or —$Z^5$—$C_{6-14}$-aryl,
wherein
$Z^5$ at each occurrence is independently $C_{1-6}$-alkylene, $C_{2-6}$-alkenylene, $C_{1-6}$-haloalkylene or a covalent bond,
$Ar^1$ at each occurrence is independently $C_{6-14}$-aryl or monovalent 5 to 14 membered aromatic heterocyclic residue, each optionally substituted with 1 to 5 substituents $R^a$, wherein each $R^a$ is independently selected from the group consisting of halogen, CN, $C_{1-6}$-alkyl, $C_{1-6}$-alkoxy and $C_{1-6}$-haloalkyl,
$Ar^2$ and $Ar^3$ at each occurrence are independently $C_{6-14}$-arylene or bivalent 5 to 14 membered aromatic heterocyclic residue, each optionally substituted with 1 to 4 substituents $R^b$, wherein each $R^b$ is independently selected from the group consisting of halogen, CN, $C_{1-6}$-alkyl, $C_{1-6}$-alkoxy and $C_{1-6}$-haloalkyl, and
$R^7$ at each occurrence is independently $C_{1-20}$-alkyl, $C_{2-20}$-alkenyl, $C_{1-20}$-haloalkyl, $C_{1-20}$-alkoxy, —$X^3$—$Ar^4$, —$X^3$—$Ar^5$—$Ar^4$, —$X^3$—$Ar^5$—$R^{10}$, or —$X^3$—$Ar^5$—$Ar^6$—$R^{10}$,
wherein
$X^3$ at each occurrence is independently —$Z^6$—O—$Z^7$—, —$Z^6$—S—$Z^7$—, —S(O)—, —C(O)—, —C(O)O—, —(CO)NR$^{11}$, —C(O)S—, —O(CO)—, —S(CO)—, —NR$^{11}$C(O)—, —NR$^{11}$—, —$Z^6$—SiR$^{11}$$_2$—$Z^7$—, $C_{1-30}$-alkylene, $C_{2-30}$-alkenylene, $C_{1-30}$-haloalkylene or a covalent bond,
wherein
$Z^6$ and $Z^7$ at each occurrence are independently $C_{1-6}$-alkylene, $C_{2-6}$-alkenylene, $C_{1-6}$-haloalkylene or a covalent bond, and
$R^{11}$ at each occurrence is independently H, $C_{1-20}$-alkyl or —$Z^8$—$C_{6-14}$-aryl,
wherein
$Z^8$ at each occurrence is independently $C_{1-6}$-alkylene, $C_{2-6}$-alkenylene, $C_{1-6}$-haloalkylene or a covalent bond,
$Ar^4$ at each occurrence is independently $C_{6-14}$-aryl or monovalent 5 to 14 membered aromatic heterocyclic residue, each optionally substituted with 1 to 5 substituents $R^c$, wherein each $R^c$ is independently selected from the group consisting of halogen, CN, —$C_{1-6}$-alkyl, $C_{1-6}$-alkoxy and $C_{1-6}$-haloalkyl,
$Ar^5$ and $Ar^6$ at each occurrence are independently $C_{6-14}$-arylene or bivalent 5 to 14 membered aromatic heterocyclic residue, each optionally substituted with 1 to 4 substituents $R^d$, wherein each $R^d$ is independently selected from the group consisting of halogen, CN, $C_{1-6}$-alkyl, $C_{1-6}$-alkoxy and $C_{1-6}$-haloalkyl, and
$R^{10}$ at each occurrence is independently $C_{1-20}$-alkyl, $C_{2-20}$-alkenyl, $C_{1-20}$-haloalkyl or $C_{1-20}$-alkoxy,
$R^3$, $R^4$ and $R^5$ can be the same or different and are H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^4$—$R^{12}$, —$X^5$—$Ar^7$, —$X^5$—$Ar^8$—$Ar^7$, —$X^5$—$Ar^8$—$R^{13}$ or —$X^5$—$Ar^8$—$Ar^9$—$R^{13}$,
wherein
$X^4$ at each occurrence is independently —[$Z^9$—O]$_b$—, —[$Z^9$—S—]$_b$—, —S(O)—, —C(O)—, —C(O)O—, —C(O)NR$^{14}$— or C(O)S—,
wherein
$Z^9$ at each occurrence is independently $C_{1-6}$-alkylene, $C_{2-6}$-alkenylene or $C_{1-6}$-haloalkylene,
b at each occurrence is independently an integer from 1 to 10 and
$R^{14}$ at each occurrence is independently H, $C_{1-20}$-alkyl, or —$Z^{10}$—$C_{6-14}$-aryl,
wherein
$Z^{10}$ at each occurrence is independently $C_{1-6}$-alkylene, $C_{2-6}$-alkenylene, $C_{1-6}$-haloalkylene or a covalent bond,
$R^{12}$ at each occurrence is independently $C_{1-30}$-alkyl, $C_{2-30}$-alkenyl or $C_{1-30}$-haloalkyl,
$X^5$ at each occurrence is independently —$Z^{11}$—O—$Z^{12}$—, —$Z^{11}$—S—$Z^{12}$—, —S(O)—, —C(O)—, —C(O)O—, —(CO)NR$^{15}$, —C(O)S—, —$Z^{11}$—SiR$^{15}$$_2$—$Z^{12}$—, $C_{1-30}$-alkylene, $C_{2-30}$-alkenylene, $C_{1-30}$-haloalkylene or a covalent bond,
wherein
$Z^{11}$ at each occurrence is independently $C_{1-6}$-alkylene, $C_{2-6}$-alkenylene or $C_{1-6}$-haloalkylene,
$Z^{12}$ at each occurrence is independently $C_{1-6}$-alkylene, $C_{2-6}$-alkenylene, $C_{1-6}$-haloalkylene or a covalent bond, and
$R^{15}$ at each occurrence is independently H, $C_{1-20}$-alkyl, or —$Z^{13}$—$C_{6-14}$-aryl,
wherein
$Z^{13}$ at each occurrence is independently $C_{1-6}$-alkylene, $C_{2-6}$-alkenylene, $C_{1-6}$ haloalkylene or a covalent bond,
$Ar^7$ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl,
$Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl and
$R^{13}$ at each occurrence is independently $C_{1-20}$-alkyl, $C_{2-20}$-alkenyl, $C_{1-20}$-haloalkyl, $C_{1-20}$-alkoxy, —$X^6$—$Ar^{10}$, —$X^6$—$Ar^{11}$—$Ar^{10}$, —$X^6$—$Ar^{11}$—$R^{16}$, or —$X^6$—$Ar^{11}$—$Ar^{12}$—$R^{17}$,
wherein
$X^6$ at each occurance is independently —$Z^{14}$—O—$Z^{15}$—, —$Z^{14}$—S—$Z^{15}$, —S(O)—, —C(O)—, —C(O)O—, —(CO)NR$^{18}$, —C(O)S—, —O(CO)—, —S(CO)—, —NR$^{18}$C(O)—, —NR$^{18}$—, —$Z^{14}$—SiR$^{18}$$_2$—$Z^{15}$—, $C_{1-30}$-alkylene, $C_{2-30}$-alkenylene, $C_{1-30}$-haloalkylene or a covalent bond,
wherein
$Z^{14}$ and $Z^{15}$ at each occurrence are independently $C_{1-6}$-alkylene, $C_{2-6}$-alkenylene, $C_{1-6}$-haloalkylene or a covalent bond, and
$R^{18}$ at each occurrence is independently H, $C_{1-20}$-alkyl or —$Z^{16}$—$C_{6-14}$-aryl,
wherein
$Z^{16}$ at each occurrence is independently $C_{1-6}$-alkylene, $C_{2-6}$-alkenylene, $C_{1-6}$-haloalkylene or a covalent bond,
$Ar^{10}$ at each occurrence is independently $C_{6-14}$-aryl or monovalent 5 to 14 membered aromatic heterocyclic residue, each optionally substituted with 1 to 5 substituents $R^g$, wherein each $R^g$ is independently selected from the group consisting of halogen, CN, $C_{1-6}$-alkyl, $C_{1-6}$-alkoxy and $C_{1-6}$-haloalkyl,
$Ar^{11}$ and $Ar^{12}$ at each occurrence are independently $C_{6-14}$-arylene or bivalent 5 to 14 membered aromatic heterocyclic residue, each optionally substituted with 1 to 4 substituents $R^h$, wherein each $R^h$ is independently selected from the group consisting of halogen, CN, $C_{1-6}$-alkyl, $C_{1-6}$-alkoxy and $C_{1-6}$-haloalkyl and
$R^{17}$ at each occurrence is independently $C_{1-20}$-alkyl, $C_{2-20}$-alkenyl, $C_{1-20}$-haloalkyl or $C_{1-20}$alkoxy,
$R^{19}$ is O or $C(CN)_2$, and
$R^{20}$ and $R^{21}$ are the same or different and are $R^{22}$ or CN, wherein $R^{22}$ has the same meaning as $R^1$,
$G^1$ and $G^2$ are the same or different and are phenylene or a monocyclic bivalent 5 to 8 membered aromatic heterocyclic residue, which phenylene and monocyclic bivalent 5 to 8 membered aromatic heterocyclic residue are optionally substituted with 1 to 4 substituents $R^i$, wherein each $R^i$ is independently selected from the group consisting of halogen, —CN, —NO$_2$, OH, $C_{1-30}$-alkyl, $C_{2-30}$-alkenyl, $C_{2-30}$-alkynyl, —$Z^{17}$—O—$C_{1-30}$-alkyl, —$Z^{17}$—S—$C_{1-30}$-alkyl, —$Z^{17}$—$C_{3-10}$-cycloalkyl, —$Z^{17}$—$C_{5-10}$-cycloalkenyl, —$Z^{17}$—$C_{8-10}$-cycloalkynyl, —$Z^{17}$—$C_{6-14}$-aryl, —$Z^{17}$-monovalent 3 to 12 membered aliphatic heterocyclic residue and —$Z^{17}$-monovalent 5 to 14 membered aromatic heterocyclic residue,
wherein $C_{1-30}$-alkyl, $C_{2-30}$-alkenyl, $C_{2-30}$-alkynyl, $C_{3-10}$-cycloalkyl, $C_{5-10}$-cycloalkenyl, $C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of haloagen, —CN, —NO$_2$, *=O, —OH, —NH$_2$, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_m$H, —S(O)$_m$—$C_{1-20}$-alkyl, —S(O)$_2$OH, —S(O)$_m$—O$C_{1-20}$-alkyl, —S(O)$_m$—OC$_{6-14}$-aryl, —CHO, —C(O)—$C_{1-20}$-alkyl, —C(O)—$C_{6-14}$-aryl, —C(O)OH, —C(O)—OC$_{1-20}$-alkyl, —C(O)—OC$_{6-14}$-aryl, —C(O)NH$_2$, —C(O)NH—$C_{1-20}$-alkyl, —C(O)N($C_{1-20}$-alkyl)$_2$, —C(O)NH—$C_{6-14}$aryl, —C(O)N($C_{1-20}$-alkyl)-$C_{6-14}$-aryl, —C(O)N($C_{6-14}$-aryl)$_2$, —C(S)NH$_2$, —C(S)NH—$C_{1-20}$-alkyl, —C(S)N($C_{1-20}$-alkyl)$_2$, —C(S)N($C_{6-14}$-aryl)$_2$, —C(S)N($C_{1-20}$-alkyl)-$C_{6-14}$-aryl, —C(S)NH—$C_{6-14}$-aryl, —S(O)$_m$NH$_2$, —S(O)$_m$NH($C_{1-20}$-alkyl), —S(O)$_m$N($C_{1-20}$-alkyl)$_2$, —S(O)$_m$NH($C_{6-14}$-aryl), —S(O)$_m$N($C_{1-20}$-alkyl)-$C_{6-14}$-aryl, —S(O)$_m$N($C_{6-14}$-aryl)$_2$, SiH$_3$, SiH($C_{1-20}$-alkyl)$_2$, SiH$_2$($C_{1-20}$-alkyl) and Si($C_{1-20}$-alkyl)$_3$, and
wherein $C_{3-10}$-cycloalkyl, $C_{5-10}$-cycloalkenyl, —$C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{2-20}$-alkenyl, $C_{2-20}$-alkynyl, $C_{1-20}$-alkoxy, —S—$C_{1-20}$-alkyl, $C_{1-20}$-haloalkyl,
wherein
$Z^{17}$ at each occurrence is independently $C_{1-6}$-alkylene, $C_{2-6}$-alkenylene, $C_{1-6}$-haloalkylene or a covalent bond, and
m at each occurrence is independently 0, 1 or 2,
L is $C_{6-24}$-arylene or a bivalent 5 to 18 membered aromatic heterocyclic residue, wherein $C_{6-24}$-arylene and bivalent 5 to 18 membered aromatic heterocyclic residue are optionally substituted with 1 to 4 substituents $R^l$, wherein each $R^l$ is independently selected from the group consisting of halogen, —CN, —NO$_2$, *=O, OH, *=C($C_{1-30}$-alkyl)$_2$, $C_{1-30}$-alkyl, $C_{2-30}$-alkenyl, $C_{2-30}$-alkynyl, —$Z^{18}$—O—$C_{1-30}$-alkyl, —$Z^{18}$—S—$C_{1-30}$-alkyl, —$Z^{18}$—$C_{3-10}$-cycloalkyl, —$Z^{18}$—$C_{5-10}$-cycloalkenyl, —$Z^{18}$—$C_{8-10}$-cycloalkynyl, —$Z^{18}$—$C_{6-14}$-aryl, —$Z^{18}$-monovalent 3 to 12 membered aliphatic heterocyclic residue and —$Z^{18}$-monovalent 5 to 14 membered aromatic heterocyclic residue,
wherein $C_{1-30}$-alkyl, $C_{2-30}$-alkenyl, $C_{2-30}$-alkynyl, $C_{3-10}$-cycloalkyl, $C_{5-10}$-cycloalkenyl, $C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN, —NO$_2$, *=O, —OH, —NH$_2$, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_o$H, —S(O)$_o$—$C_{1-20}$-alkyl, —S(O)$_2$OH, —S(O)$_o$—O$C_{1-20}$-alkyl, —S(O)$_o$—OC$_{6-14}$-aryl, —CHO, —C(O)—$C_{1-20}$-alkyl, —C(O)—$C_{6-14}$-aryl, —C(O)OH, —C(O)—OC$_{1-20}$-alkyl, —C(O)—OC$_{6-14}$-aryl, —C(O)NH$_2$, —C(O)NH—$C_{1-20}$-alkyl, —C(O)N($C_{1-20}$-alkyl)$_2$, —C(O)NH—$C_{6-14}$-aryl, —C(O)N($C_{1-20}$-alkyl)-$C_{6-14}$-aryl, —C(O)N($C_{6-14}$-aryl)$_2$, —C(S)NH$_2$, —C(S)NH—$C_{1-20}$-alkyl, —C(S)N($C_{1-20}$-alkyl)$_2$, —C(S)N($C_{6-14}$-aryl)$_2$, —C(S)N($C_{1-20}$-alkyl)-$C_{6-14}$-aryl, —C(S)NH—$C_{6-14}$-aryl, —S(O)$_o$NH$_2$, —S(O)$_o$NH($C_{1-20}$-alkyl), —S(O)$_o$N($C_{1-20}$-alkyl)$_2$, —S(O)$_o$NH($C_{6-14}$-aryl), —S(O)$_o$N($C_{1-20}$-alkyl)-$C_{6-14}$-aryl, —S(O)$_o$N($C_{6-14}$-aryl)$_2$, SiH$_3$, SiH($C_{1-20}$-alkyl)$_2$, SiH$_2$($C_{1-20}$-alkyl) and Si($C_{1-20}$-alkyl)$_3$, and
wherein $C_{3-10}$-cycloalkyl, $C_{5-10}$-cycloalkenyl, —$C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^n$, wherein each R'' is independently selected from the group consisting of $C_{1-20}$-alkyl, $C_{2-20}$-alkenyl, $C_{2-20}$-alkynyl, $C_{1-20}$-alkoxy, —S—$C_{1-20}$-alkyl, $C_{1-20}$-haloalkyl,
wherein
$Z^{18}$ at each occurrence is independently $C_{1-6}$-alkylene, $C_{2-6}$-alkenylene, $C_{1-6}$-haloalkylene or a covalent bond, and
o at each occurrence is independently 0, 1 or 2,
or
L is

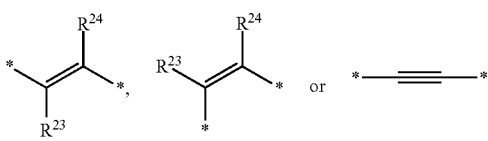

wherein
$R^{23}$ and $R^{24}$ can be the same or different and are H, halogen, —CN, $C_{1-30}$-alkyl, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, —$X^7$—$R^{25}$, —$X^8$—$Ar^{13}$, —$X^8$—$Ar^{14}$—$Ar^{13}$, —$X^8$—$Ar^{14}$—$R^{26}$ or —$X^8$—$Ar^{14}$—$Ar^{15}$—$R^{26}$,
wherein
$X^7$ at each occurrence is independently —O—, —[$Z^{19}$—O]$_c$—, —[O—$Z^{19}$]$_c$—O—, —S—, —[$Z^{19}$—S—]$_c$—, —[S—$Z^{19}$]$_c$—S—, —S(O)—, —C(O)—, —C(O)O—, —C(O)NR$^{27}$—, C(O)S—, —O(CO)—, —S(CO)—, —NR$^{27}$C(O)— or —NR$^{27}$—,
wherein
$Z^{19}$ at each occurrence is independently $C_{1-6}$-alkylene, $C_{2-6}$-alkenylene or $C_{1-6}$-haloalkylene,
c at each occurrence is independently an integer from 1 to 10 and
$R^{27}$ at each occurrence is independently H, $C_{1-20}$-alkyl, or —$Z^{20}$—$C_{6-14}$-aryl,
wherein
$Z^{20}$ at each occurrence is independently $C_{1-6}$-alkylene, $C_{2-6}$-alkenylene, $C_{1-6}$-haloalkylene or a covalent bond,
$R^{25}$ at each occurrence is independently $C_{1-30}$-alkyl, $C_{2-30}$-alkenyl or $C_{1-30}$-haloalkyl,
$X^8$ at each occurrence is independently —$Z^{21}$—O—$Z^{22}$—, —$Z^{21}$—S—$Z^{22}$—, —S(O)—, —C(O)—, —C(O)O—, —(CO)NR$^{28}$—, —C(O)S—, —O(CO)—, —S(CO)—, —NR$^{28}$C(O)—, —NR$^{28}$—, —$Z^{21}$—SiR$^{28}_2$—$Z^{22}$—, $C_{1-30}$-alkylene, $C_{2-30}$-alkenylene, $C_{1-30}$-haloalkylene or a covalent bond,
wherein
$Z^{21}$ and $Z^{22}$ at each occurrence are independently $C_{1-6}$-alkylene, $C_{2-6}$-alkenylene, $C_{1-6}$-haloalkylene or a covalent bond, and
$R^{28}$ at each occurrence is independently H, $C_{1-20}$-alkyl, or —$Z^{23}$—$C_{6-14}$-aryl,
wherein
$Z^{23}$ at each occurrence is independently $C_{1-6}$-alkylene, $C_{2-6}$-alkenylene, $C_{1-6}$-haloalkylene or a covalent bond,
$Ar^{12}$ at each occurrence is independently $C_{6-14}$-aryl or monovalent 5 to 14 membered aromatic hetrocyclic residue, each optionally substituted with 1 to 5 substituents R$^o$, wherein each R$^o$ is independently selected from the group consisting of halogen, CN, $C_{1-6}$-alkyl, $C_{1-6}$-alkoxy and $C_{1-6}$-haloalkyl, $Ar^{14}$ and $Ar^{15}$ at each occurrence are independently $C_{6-14}$-arylene or bivalent 5 to 14 membered aromatic heterocyclic residue, each optionally substituted with 1 to 4 substituents R$^p$, wherein each R$^p$ is independently selected from the group consisting of halogen, CN, $C_{1-6}$-alkyl, $C_{1-6}$-alkoxy and $C_{1-6}$-haloalkyl, and
$R^{26}$ at each occurrence is independently $C_{1-20}$-alkyl, $C_{2-20}$-alkenyl, $C_{1-20}$-haloalkyl, $C_{1-20}$-alkoxy, —$X^9$—$Ar^{16}$, —$X^9$—$Ar^{17}$—$Ar^{16}$, —$X^9$—$Ar^{17}$—$R^{29}$, or —$X^9$—$Ar^{17}$—$Ar^{18}$—$R^{29}$,
wherein
$X^9$ at each occurrence is independently —$Z^{24}$—O—$Z^{25}$—, —$Z^{24}$—S—$Z^{25}$—, —S(O)—, —C(O)—, —C(O)O—, —(CO)NR$^{30}$—, —C(O)S—, —O(CO)—, —S(CO)—, —NR$^{30}$C(O)—, —NR$^{30}$—, —$Z^{24}$—SiR$^{30}_2$—$Z^{25}$—, $C_{1-30}$-alkylene, $C_{2-30}$-alkenylene, $C_{1-30}$-haloalkylene or a covalent bond,
wherein
$Z^{24}$ and $Z^{25}$ at each occurrence are independently $C_{1-6}$-alkylene, $C_{2-6}$-alkenylene, $C_{1-6}$-haloalkylene or a covalent bond, and
$R^{30}$ at each occurrence is independently H, $C_{1-20}$-alkyl or —$Z^{26}$—$C_{6-14}$-aryl,
wherein
$Z^{26}$ at each occurrence is independently $C_{1-6}$-alkylene, $C_{2-6}$-alkenylene, $C_{1-6}$-haloalkylene or a covalent bond,
$Ar^{16}$ at each occurrence is independently $C_{6-14}$-aryl or monovalent 5 to 14 membered aromatic heterocyclic residue, each optionally substituted with 1 to 5 substituents R$^q$, wherein each R$^q$ is independently selected from the group consisting of halogen, CN, $C_{1-6}$-alkyl, $C_{1-6}$-alkoxy and $C_{1-6}$-haloalkyl,
$Ar^{17}$ and $Ar^{18}$ at each occurrence are independently $C_{6-14}$-arylene or bivalent 5 to 14 membered aromatic heterocyclic residue, each optionally substituted with 1 to 4 substituents R$^r$, wherein each R$^r$ is independently selected from the group consisting of halogen, CN, $C_{1-6}$-alkyl, $C_{1-6}$-alkoxy and $C_{1-6}$-haloalkyl, and
$R^{29}$ at each occurrence is independently $C_{1-20}$-alkyl, $C_{2-20}$-alkenyl, $C_{1-20}$-haloalkyl or $C_{1-20}$-alkoxy,
q and s are the same or different and are 0, 1, 2, 3, 4 or 5,
r is 0, 1 or 2,
and
n is an integer from 2 to 10,000.

2. The oligomer or polymer of formula (1) of claim 1 wherein E is

3. An oligomer or polymer of formula (1)

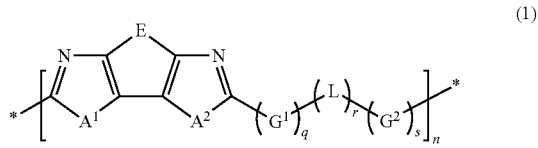

(1)

wherein
A$^1$ and A$^2$ can be the same or different and are S or Se,
E is selected from the group consisting of

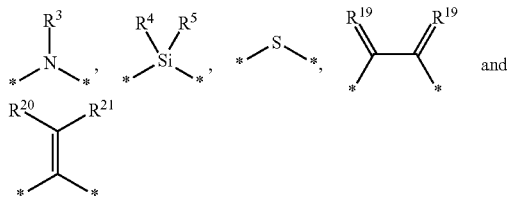

wherein
R$^1$ is H, halogen, —CN, C$_{1-30}$-alkyl, C$_{2-30}$-alkenyl, C$_{2-30}$-alkynyl, C$_{3-10}$-cycloalkyl, C$_{5-10}$-cycloalkenyl, C$_{8-10}$-cycloakynyl, C$^{1-30}$-haloalkyl, monovalent 3 to 12 membered aliphatic heterocyclic residue, —X$^1$—R$^6$, —X$^2$—Ar$^1$, —X$^2$—Ar$^2$—Ar$^1$, —X$^2$—Ar$^2$R$^7$ or —X$^2$—Ar$^2$—Ar$^3$—R$^7$,
wherein
X$^1$ at each occurrence is independently —O—, —[Z$^1$—O]$_a$—, —[O—Z$^1$]$_a$—O—, —S—, —[Z$^1$—S—]$_a$—, —[S—Z$^1$]$_a$—S—, —S(O)—, —C(O)—, —C(O)O—, —C(O)NR$^8$—, C(O)S—, —O(CO)—, —S(CO)—, —NR$^8$C(O)— or —NR$^8$—,
wherein
Z$^1$ at each occurrence is independently C$_{1-6}$-alkylene, C$_{2-6}$-alkenylene or C$_{1-6}$-haloalkylene,
a at each occurrence is independently an integer from 1 to 10 and
R$^8$ at each occurrence is independently H, C$_{1-20}$-alkyl, or —Z$^2$—C$_{6-14}$-aryl,
wherein
Z$^2$ at each occurrence is independently C$_{1-6}$-alkylene, C$_{2-6}$-alkenylene, C$_{1-6}$-haloalkylene or a covalent bond,
R$^6$ at each occurrence is independently C$_{1-30}$-alkyl, C$_{2-30}$alkenyl or C$_{1-30}$-haloalkyl,
X$^2$ at each occurrence is independently —Z$^3$—O—Z$^4$—, —Z$^3$—S—Z$^4$—, —S(O)—, —C(O)—, —C(O)O—, —(CO)NR$^9$, —C(O)S—, —O(CO)—, —S(CO)—, —NR$^9$C(O)—, —NR$^9$—, —Z$^3$—SiR$^9{}_2$—Z$^4$—, C$_{1-30}$-alkylene, C$_{2-30}$-alkenylene, C$_{1-30}$-haloalkylene or a covalent bond,
wherein
Z$^3$ and Z$^4$ at each occurrence are independently C$_{1-6}$-alkylene, C$_{2-6}$-alkenylene, C$_{1-6}$-haloalkylene or a covalent bond, and
R$^9$ at each occurrence is independently H, C$_{1-20}$-alkyl, or —Z$^5$—C$_{6-14}$-aryl,
wherein
Z$^5$ at each occurrence is independently C$_{1-6}$-alkylene, C$_{2-6}$-alkenylene, C$_{1-6}$-haloalkylene or a covalent bond,
Ar$^1$ at each occurrence is independently C$_{6-14}$-aryl or monovalent 5 to 14 membered aromatic heterocyclic residue, each optionally substituted with 1 to 5 substituents R$^a$, wherein each R$^a$ is independently selected from the group consisting of halogen, CN, C$_{1-6}$-alkyl, C$_{1-6}$-alkoxy and C$_{1-6}$-haloalkyl,
Ar$^2$ and Ar$^3$ at each occurrence are independently C$_{6-14}$-arylene or bivalent 5 to 14 membered aromatic heterocyclic residue each optionally substituted with 1 to 4 substituents R$^b$, wherein each R$^b$ is independently selected from the group consisting of halogen, CN, C$_{1-6}$-alkyl, C$_{1-6}$-alkoxy and C$_{1-6}$-haloalkyl and R$^7$ at each occurrence is independently C$_{1-20}$-alkyl, C$_{2-20}$-alkenyl, C$_{1-20}$-haloalkyl, C$_{1-20}$-alkoxy, —X$^3$—Ar$^4$, —X$^3$—Ar$^5$—Ar$^4$, —X$^3$—Ar$^5$—R$^{10}$, or —X$^3$—Ar$^5$—Ar$^6$—R$^{10}$,
wherein
X$^3$ at each occurrence is independently —Z$^6$—O—Z$^7$—, —Z$^6$—S—Z$^7$, —S(O)—, —C(O)—, —C(O)O—, —(CO)NR$^{11}$, —C(O)S—, —O(CO)—, —S(CO)—, —NR$^{11}$C(O)—, —NR$^{11}$—, —Z$^6$—SiR$^{11}{}_2$—Z$^7$—, C$_{1-30}$-alkylene, C$_{2-30}$-alkenylene, C$_{1-30}$-haloalkylene or a covalent bond,
wherein
Z$^6$ and Z$^7$ at each occurrence are independently C$_{1-6}$-alkylene, C$_{2-6}$-alkenylene, C$_{1-6}$-haloalkylene or a covalent bond, and
R$^{11}$ at each occurrence is independently H, C$_{1-20}$-alkyl or —Z$^8$—C$_{6-14}$aryl,
wherein
Z$^8$ at each occurrence is independently C$_{1-6}$-alkylene, C$_{2-6}$-alkenylene, C$_{1-6}$-haloalkylene or a covalent bond,
Ar$^4$ at each occurrence is independently C$_{6-14}$-aryl movalent 5 to 14 membered aromatic heterocyclic residue, each optionally substituted with 1 to 5 substituents R$^c$, wherein each R$^c$ is independently selected from the group consisting of halogen, CN, C$_{1-6}$-alkyl, C$_{1-6}$-alkoxy and C$_{1-6}$-haloalkyl,
Ar$^5$ and Ar$^6$ at each occurrence are independently C$_{6-14}$-arylene or bivalent 5 to 14 membered aromatic heterocyclic residue, each optionally substituted with 1 to 4 substituents R$^d$, wherein each R$^d$ is independently selected from the group consisting of halogen, CN, C$_{1-6}$-alkyl, C$_{1-6}$-alkoxy and C$_{1-6}$-haloalkyl, and
R$^{10}$ at each occurrence is independently C$_{1-20}$-alkyl, C$_{2-20}$-alkenyl, C$_{1-20}$-haloalkyl or C$_{1-20}$-alkoxy,
R$^4$ and R$^5$ can be the same or different and are H, halogen, —CN, C$_{1-30}$-alkyl, C$_{2-30}$-alkenyl, C$_{2-20}$-alkynyl, C$_{3-10}$-cycloalkyl, C$_{5-10}$-cycloalkenyl, C$_{8-10}$-cycloalkynyl, C$_{1-30}$-haloalkyl, monovalent 3 to 12 membered aliphatic heterocyclic residue, —X$^4$—R$^{12}$, —X$^5$—Ar$^7$, —X$^5$—Ar$^8$—Ar$^7$, —X$^5$—Ar$^8$—R$^{13}$ or —X$^5$—Ar$^8$—Ar$^9$—R$^{13}$,
wherein
X$^4$ at each occurrence is independently —[Z$^9$—O]$_b$—, —[Z$^9$—S—]$_b$—, —S(O)—, —C(O)—, —C(O)O—, —C(O)NR$^{14}$— or C(O)S—,
wherein
Z$^9$ at each occurrence is independently C$_{1-6}$-alkylene, C$_{2-6}$-alkenylene or C$_{1-6}$-haloalkylene,
b at each occurrence is independently an integer from 1 to 10 and
R$^{14}$ at each occurrence is independently H, C$_{1-20}$-alkyl, or —Z$^{10}$—C$_{6-14}$-aryl,
wherein
Z$^{10}$ at each occurrence is independently C$_{1-6}$-alkylene, C$_{2-6}$-alkenylene, C$_{1-6}$-haloalkylene or a covalent bond,
R$^{12}$ at each occurrence is independently C$_{1-30}$-alkyl, C$_{2-30}$-alkenyl or C$_{1-30}$-haloalkyl,
X$^5$ at each occurrence is independently —Z$^{11}$—O—Z$^{12}$—, —Z$^{11}$—S—Z$^{12}$—, —S(O)—, —C(O)—, —C(O)O—, —(CO)NR$^{15}$, —C(O)S—, —Z$^{11}$—SiR$^{15}{}_2$—Z$^{12}$—, C$_{1-30}$-alkylene, C$_{2-30}$-alkenylene, C$_{1-30}$-haloalkylene or a covalent bond,
wherein
Z$^{11}$ at each occurrence is independently C$_{1-6}$alkylene, C$_{2-6}$alkenylene or C$_{1-6}$-haloalkylene, $Z^{12}$ at each occurrence is independently $C_{1-6}$-alkylene, $C_{2-6}$-alkenylene, $C_{1-6}$-haloalkylene or a covalent bond, and $R^{15}$ at each occurrence is independently H, $C_{1-20}$-alkyl, or 13 $Z^{13}$—$C_{6-14}$-aryl, wherein $Z^{13}$ at each occurrence is independently $C_{1-6}$-alkylene, $C_{2-6}$alkenylene, $C_{1-6}$-haloalkylene or a covalent bond, $Ar^7$ at each occurrence is independently $C_{6-14}$aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl, $Ar^8$ and $Ar^9$ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl and $R^{13}$ at each occurrence is independently $C_{1-20}$-alkyl, $C_{2-20}$-alkenyl, $C_{1-20}$-haloalkyl, $C_{1-20}$-alkoxy, —$X^6$—$Ar^{10}$, —$X^6$—$Ar^{11}$—$Ar^{10}$, —$X^6$—$Ar^{11}$—$R^{16}$, or —$X^6$—$Ar^{11}$—$Ar^{12}$—$R^{17}$, wherein $X^6$ at each occurrence is independently —$Z^{14}$—O—$Z^{15}$—, —$Z^{14}$—S—$Z^{15}$—, —S(O)—, —C(O)—, —C(O)O—, —(CO)NR$^{18}$, —C(O)S—, —O(CO)—, —S(CO)—, —NR$^{18}$C(O)—, —NR$^{18}$—, —$Z^{14}$—SiR$^{18}_2$—$Z^{15}$—, $C_{1-30}$-alkylene, $C_{2-30}$-alkenylene, $C_{1-30}$-haloalkylene or a covalent bond, wherein $Z^{14}$ and $Z^{15}$ at each occurrence are independently $C_{1-6}$-alkylene, $C_{2-6}$-alkenylene, $C_{1-6}$-haloalkylene or a covalent bond, and $R^{18}$ at each occurrence is independently H, $C_{1-20}$-alkyl or —$Z^{16}$—$C_{6-14}$-aryl, wherein $Z^{16}$ at each occurrence is independently $C_{1-6}$-alkylene, $C_{2-6}$alkenylene, $C_{1-6}$-haloalkylene or a covalent bond, $Ar^{10}$ at each occurrence is independently $C_{6-14}$-aryl or monovalent 5 to 14 membered aromatic heterocyclic residue, each optionally substituted with 1 to 5 substituents $R^g$, wherein each $R^g$ is independently selected from the group consisting of halogen, CN, $C_{1-6}$alkyl, $C_{1-6}$-alkoxy and $C_{1-6}$-haloalkyl, $Ar^{11}$ and $Ar^{12}$ at each occurrence are independently $C_{6-14}$-arylene or bivalent 5 to 14 membered aromatic heterocyclic residue, each optionally substituted with 1 to 4 substituents $R^h$, wherein each $R^h$ is independently selected from the group consisting of halogen, CN, $C_{1-6}$-alkyl, $C_{1-6}$-alkoxy and $C_{1-6}$-haloalkyl and $R^{17}$ at each occurrence is independently $C_{1-20}$-alkyl, $C_{2-20}$-alkenyl, $C_{1-20}$-haloalkyl or $C_{1-20}$-alkoxy, $R^{19}$ is O or C(CN)$_2$, and $R^{20}$ and $R^{21}$ are the same or different and are $R^{22}$ or CN, wherein $R^{22}$ has the same meaning as $R^1$, $G^1$ and $G^2$ are same or different and are phenylene or a monocyclic bivalent 5 to 8 membered aromatic heterocyclic residue, which phenylene and monocyclic bivalent 5 to 8 membered aromatic heterocyclic residue are optionally substituted with 1 to 4 substituents $R^i$, wherein each $R^i$ is independently selected from the group consisting of halogen, —CN, —NO$_2$, OH, $C_{1-30}$-alkyl, $C_{2-30}$-alkenyl, $C_{2-30}$-alkynyl, —$Z^{17}$—O—$C_{1-30}$-alkyl, —$Z^{17}$—$C_{1-30}$-alkyl, —$Z^{17}$—$C_{3-10}$-cycloalkyl, —$Z^{17}$—$C_{5-10}$-cycloalkenyl, —$Z^{17}$—$C_{8-10}$-cycloalkynyl, —$Z^{17}$—$C_{6-14}$-aryl, —$Z^{17}$-monovalent3 to 12 membered aliphatic heterocyclic residue and —$Z^{17}$-monovalent 5 to 14 membered aromatic heterocyclic residue, wherein $C_{1-30}$-alkyl, $C_{2-30}$-alkenyl, $C_{2-30}$-alkynyl, $C_{3-10}$-cycloalkyl, $C_{5-10}$-cycloalkenyl, $C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN, —NO$_2$, *=O, —OH, —NH$_2$, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_m$H, —S(O)$_m$—$C_{1-20}$-alkyl, —S(O)$_2$OH, —S(O)$_m$—OC$_{1-20}$-alkyl, —S(O)$_m$—OC$_{6-14}$-aryl, —CHO, —C(O)—$C_{1-20}$-alkyl, —C(O)—$C_{6-14}$-aryl, —C(O)OH, —C(O)—OC$_{1-20}$-alkyl, —C(O)—OC$_{6-14}$-aryl, —C(O)NH$_2$, —C(O)NH—$C_{1-20}$-alkyl, —C(O)N($C_{1-20}$-alkyl)$_2$, —C(O)NH—$C_{6-14}$-aryl, —C(O)N($C_{1-20}$-alkyl)-$C_{6-14}$-aryl, —C(O)N($C_{6-14}$-aryl)$_2$, —C(S)NH$_2$, —C(S)NH—$C_{1-20}$-alkyl, —C(S)N($C_{1-20}$-alkyl)$_2$, —C(S)N($C_{6-14}$-aryl)$_2$, —C(S)N($C_{1-20}$-alkyl)-$C_{6-14}$-aryl, —C(S)NH—$C_{6-14}$-aryl, —S(O)$_m$NH$_2$, —S(O)$_m$NH($C_{1-20}$-alkyl), —S(O)$_m$N($C_{1-20}$-alkyl)$_2$, —S(O)$_m$NH($C_{6-14}$aryl), —S(O)$_m$N($C_{1-20}$-alkyl)-$C_{6-14}$-aryl, —S(O)$_m$N($C_{6-14}$aryl)$_2$, SiH$_3$, SiH($C_{1-20}$-alkyl)$_2$, SiH$_2$($C_{1-20}$-alkyl) and Si($C_{1-20}$-alkyl)$_3$, and wherein $C_{3-10}$-cycloalkyl, $C_{5-10}$-cycloalkenyl, —$C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{2-20}$-alkenyl, $C_{2-20}$-alkynyl, $C_{1-20}$-alkoxy, —S—$C_{1-20}$-alkyl, $C_{1-20}$-haloalkyl, wherein $Z^{17}$ at each occurrence is independently $C_{1-6}$-alkylene, $C_{2-6}$-alkenylene, $C_{1-6}$-haloalkylene or a covalent bond, and m at each occurrence is independently 0, 1 or 2, L is $C_{6-24}$-arylene or a bivalent 5 to 18 membered aromatic heterocyclic residue, wherein $C_{6-24}$-arylene and bivalent 5 to 18 membered aromatic heterocyclic residue are optionally substituted with 1 to 4 substituents $R^l$, wherein each $R^l$ is independently selected from the group consisting of halogen, —CN, —NO$_2$, *=O, OH, *=C($C_{1-30}$-alkyl)$_2$, $C_{1-30}$-alkyl, $C_{2-30}$-alkenyl, $C_{2-30}$-alkynyl, —$Z^{18}$—O—$C_{1-30}$-alkyl, —$Z^{18}$—S—$C_{1-30}$-alkyl, —$Z^{18}$—$C_{3-10}$-cycloalkyl, —$Z^{18}$—$C_{5-10}$-cycloalkenyl, —$Z^{18}$—$C_{8-10}$-cycloalkynyl, —$Z^{18}$—$C_{6-14}$-aryl, —$Z^{18}$-monovalent 3 to 12 membered aliphatic heterocyclic residue and —$Z^{18}$-monovalent 5 to 14 membered aromatic heterocyclic residue, wherein $C_{1-30}$-alkyl, $C_{2-30}$-alkenyl, $C_{2-30}$-alkynyl, $C_{3-10}$-cycloalkyl, $C_{5-10}$-cycloalkenyl, $C_{8-10}$-cycloalkynyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN, —NO$_2$, *=O, —OH, —NH$_2$, —NH($C_{1-20}$-alkyl), —N($C_{1-20}$-alkyl)$_2$, —N($C_{1-20}$-alkyl)-$C_{6-14}$-aryl, —N($C_{6-14}$-aryl)$_2$, —S(O)$_o$H, —S(O)$_o$—$C_{1-20}$-alkyl, —S(O)$_2$OH, —S(O)$_o$—OC$_{1-20}$- alkyl, —S(O)$_o$—OC$_{6-14}$-aryl, —CHO, —C(O)—C$_{1-20}$-alkyl, —C(O)—C$_{6-14}$-aryl, —C(O)OH, —C(O)—OC$_{1-20}$-alkyl, —C(O)—OC$_{6-14}$-aryl, —C(O)NH$_2$, —C(O)NH—C$_{1-20}$-alkyl, —C(O)N(C$_{1-20}$-alkyl)$_2$, —C(O)NH—C$_{6-14}$-aryl, —C(O)N(C$_{1-20}$-alkyl)-C$_{6-14}$-aryl, —C(O)N(C$_{6-14}$-aryl)$_2$, —C(S)NH$_2$, —C(S)NH—C$_{1-20}$alkyl, —C(S)N(C$_{1-20}$-alkyl)$_2$, —C(S)N(C$_{6-14}$-aryl)$_2$, —C(S)N(C$_{1-20}$-alkyl)-C$_{6-14}$-aryl, —C(S)NH—C$_{6-14}$-aryl, —S(O)$_o$NH$_2$, —S(O)$_o$NH(C$_{1-20}$-alkyl), —S(O)$_o$N(C$_{1-20}$-alkyl)$_2$, —S(O)$_o$NH(C$_{6-14}$-aryl), —S(O)$_o$N(C$_{1-20}$-alkyl)-C$_{6-14}$-aryl, —S(O)$_o$N(C$_{6-14}$-aryl)$_2$, SiH$_3$, SiH(C$_{1-20}$-alkyl)$_2$, SiH$_2$(C$_{1-20}$-alkyl) and Si(C$_{1-20}$-alkyl)$_3$, and wherein C$_{3-10}$-cycloalkyl, C$_{5-10}$-cycloalkenyl, —C$_{8-10}$-cycloalkynyl, C$_{6-14}$-aryl, monovalent 3 to 12 membered aliphatic heterocyclic residue and monovalent 5 to 14 membered aromatic heterocyclic residue is optionally substituted with 1 to 4 substituents R'', wherein each R'' is independently selected from the group consisting of C$_{1-20}$-alkyl, C$_{2-20}$-alkenyl, C$_{2-20}$-alkynyl, C$_{1-20}$-alkoxy, —S—C$_{1-20}$-alkyl, C$_{1-20}$-haloalkyl, wherein Z$^{18}$ at each occurrence is independently C$_{1-6}$-alkylene, C$_{2-6}$-alkenylene, C$_{1-6}$-haloalkylene or a covalent bond, and o at each occurrence is independently 0, 1 or 2, or L is

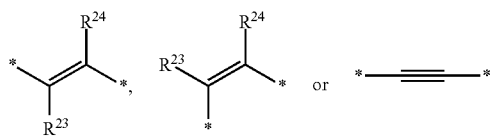

wherein

R$^{23}$ and R$^{24}$ can be the same or different and are H, halogen, —CN, C$_{1-30}$-alkyl, C$_{2-30}$-alkenyl, C$_{2-20}$-alkynyl, C$_{3-10}$-cycloalkyl, C$_{5-10}$-cycloalkenyl, C$_{8-10}$-cycloalkynyl, C$_{1-30}$-haloalkyl, monovalent 3 to 12 membered aliphatic heterocyclic residue, —X$^7$—R$^{25}$, —X$^8$—Ar$^{13}$, —X$^8$—Ar$^{14}$—Ar$^{13}$, —X$^8$—Ar$^{14}$—R$^{26}$ or —X$^8$—Ar$^{14}$—Ar$^{15}$—R$^{26}$, wherein X$^7$ at each occurrence is independently —O—, —[Z$^{19}$—O]$_c$—, —[O—Z$^{19}$]$_c$—O—, —S—, —[Z$^{19}$—S—]$_c$—, —[S—Z$^{19}$]$_c$—S—, —S(O), —C(O)—, —C(O)O—, —C(O)NR$^{27}$—, C(O)S—, —O(CO)—, —S(CO)—, —NR$^{27}$C(O)— or —NR$^{27}$—, wherein Z$^{19}$ at each occurrence is independently C$_{1-6}$-alkylene, C$_{2-6}$-alkenylene or C$_{1-6}$-haloalkylene, c at each occurrence is independently an integer from 1 to 10 and R$^{27}$ at each occurrence is independently H, C$_{1-20}$-alkyl, or —Z$^{20}$—C$_{6-14}$-aryl, wherein Z$^{20}$ at each occurrence is independently C$_{1-6}$-alkylene, C$_{2-6}$-alkenylene, C$_{1-6}$-haloalkylene or a covalent bond, R$^{25}$ at each occurrence is independently C$_{1-30}$-alkyl, C$_{2-30}$-alkenyl or C$_{1-30}$-haloalkyl, X$^8$ at each occurrence is independently —Z$^{21}$—O—Z$^{22}$—, —Z$^{21}$—S—Z$^{22}$—, —S(O)—, —C(O)—, —C(O)O—, —(CO)NR$^{28}$, —C(O)S—, —O(CO)—, —S(CO)—, —NR$^{28}$C(O)—, —NR$^{28}$—, —Z$^{21}$—SiR$^{28}{}_2$—Z$^{22}$—, C$_{1-30}$-alkylene, C$_{2-30}$-haloalkenylene, C$_{1-30}$-haloalkylene or a covalent bond, wherein Z$^{21}$ and Z$^{22}$ at each occurrence are independently C$_{1-6}$-alkylene, C$_{2-6}$-alkenylene, C$_{1-6}$-haloalkylene or a covalent bond, and R$^{28}$ at each occurrence is independently H, C$_{1-20}$-alkyl, or —Z$^{23}$—C$_{6-14}$-aryl, wherein Z$^{23}$ at each occurrence is independently C$_{1-6}$-alkylene, C$_{2-6}$-alkenylene, C$_{1-6}$-haloalkylene or a covalent bond, Ar$^{12}$ at each occurrence is independently C$_{6-14}$-aryl or monovalent 5 to 14 membered aromatic heterocyclic residue, each optionally substituted with 1 to 5 substituents R$^o$, wherein each R$^o$ is independently selected from the group consisting of halogen, CN, C$_{1-6}$-alkyl, C$_{1-6}$-alkoxy and C$_{1-6}$-haloalkyl, Ar$^{14}$ and Ar$^{15}$ at each occurrence are independently C$_{6-14}$-arylene or bivalent 5 to 14 membered aromatic heterocyclic residue, each optionally substituted with 1 to 4 substituents R$^p$, wherein each R$^p$ is independently selected from the group consisting of halogen, CN, C$_{1-6}$-alkyl, C$_{1-6}$-alkoxy and C$_{1-6}$-haloalkyl, and R$^{26}$ at each occurrence is independently C$_{1-20}$-alkyl, C$_{2-20}$-alkenyl, C$_{1-20}$-haloalkyl, C$_{1-20}$-alkoxy, —X$^9$—Ar$^{16}$, —X$^9$—Ar$^{17}$—Ar$^{16}$, —X$^9$—Ar$^{17}$—R$^{29}$, or —X$^9$—Ar$^{17}$—Ar$^{18}$—R$^{29}$, wherein X$^9$ at each occurrence is independently —Z$^{24}$—O—Z$^{25}$—, —Z$^{24}$—S—Z$^{25}$, —S(O)—, —C(O)—, —C(O)O—, —(CO)NR$^{30}$, —C(O)S—, —O(CO)—, —S(CO)—, —NR$^{30}$C(O)—, —NR$^{30}$—, —Z$^{24}$—SiR$^{30}{}_2$—Z$^{25}$—, C$_{1-30}$-alkylene, C$_{2-30}$-alkenylene, C$_{1-30}$-haloalkylene or a covalent bond, wherein Z$^{24}$ and Z$^{25}$ at each occurrence are independently C$_{1-6}$-alkylene, C$_{2-6}$-alkenylene, C$_{1-6}$-haloalkylene or a covalent bond, and R$^{30}$ at each occurrence is independently H, C$_{1-20}$-alkyl or —Z$^{26}$—C$_{6-14}$-aryl, wherein Z$^{26}$ at each occurrence is independently C$_{1-6}$-alkylene, C$_{2-6}$-alkenylene, C$_{1-6}$-haloalkylene or a covalent bond, Ar$^{16}$ at each occurrence is independently C$_{6-14}$-aryl or monovalent 5 to 14 membered aromatic heterocyclic residue. each optionally substituted with 1 to 5 substituents R$^q$, wherein each R$^q$ is independently selected from the group consisting of halogen, CN, C$_{1-6}$-alkyl, C$_{1-6}$-alkoxy and C$_{1-6}$-haloalkyl, Ar$^{17}$ and Ar$^{18}$ at each occurrence are independently C$_{6-14}$-arylene or bivalent 5 to 14 membered aromatic heterocyclic residue, each optionally substituted with 1 to 4 substituents R$^r$, wherein each R$^r$ is independently selected from the group consisting of halogen, CN, C$_{1-6}$-alkyl, C$_{1-6}$-alkoxy and C$_{1-6}$-haloalkyl, and R$^{29}$ at each occurrence is independently C$_{1-20}$-alkyl, C$_{2-20}$-alkenyl, C$_{1-20}$-haloalkyl or C$_{1-20}$-alkoxy, q and s are the same or different and are 0, 1, 2, 3, 4 or 5, r is 0, 1 or 2, and n is an integer from 2 to 10,000, wherein R$^3$ is —X$^5$—Ar$^7$, —X$^5$—Ar$^8$—Ar$^7$, —X$^5$Ar$^8$—R$^{13}$ or —X$^5$—Ar$^8$—Ar$^9$—R$^{13}$, wherein
X⁵ at each occurrence is a covalent bond,
Ar⁷ at each occurrence is independently $C_{6-14}$-aryl or monovalent 5 to 14 membered aromatic heterocyclic residue, each optionally substituted with 1 to 5 substituents $R^e$, wherein each $R^e$ is independently selected from the group consisting of halogen, CN, $C_{1-6}$-alkyl, $C_{1-6}$-alkoxy and $C_{1-6}$-haloalkyl,
Ar⁸ and Ar⁹ at each occurrence are independently $C_{6-14}$-arylene or bivalent 5 to 14 membered aromatic heterocyclic residue, each optionally substituted with 1 to 4 substituents $R^f$, wherein each $R^f$ is independently selected from the group consisting of halogen, CN, $C_{1-6}$-alkyl, $C_{1-6}$-alkoxy and $C_{1-6}$-haloalkyl, and
R¹³ at each occurrence is independently $C_{1-20}$-alkyl, $C_{2-20}$-alkenyl, $C_{1-20}$-haloalkyl or $C_{1-20}$-alkoxy.

4. The oligomer or polymer of formula (1) of claim 1, wherein R³ is —X⁵—Ar⁸—R¹³,
wherein
X⁵ is a covalent bond,
Ar⁸ is $C_{6-14}$-arylene, and
R¹³ is $C_{1-20}$-alkyl.

5. The oligomer or polymer of formula (1) of claim 1, wherein G¹ and G² are the same or different and are phenylene,

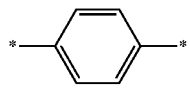

or, a monocyclic bivalent 5 to 8 membered aromatic heterocyclic residue selected from the group consisting of

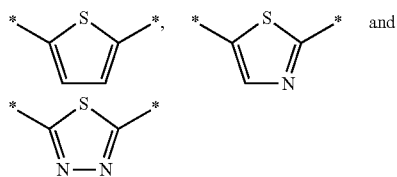 and which phenylene or monocyclic bivalent 5 to 8 membered aromatic heterocyclic residue are optionally substituted with 1 to 2 substituents $R^i$, wherein each $R^i$ is independently selected from the group consisting of $C_{1-30}$-alkyl, —Z¹⁷—O—$C_{1-30}$-alkyl, —Z¹⁷—S—$C_{1-30}$-alkyl, —Z¹⁷—$C_{3-10}$-cycloalkyl, —Z¹⁷—$C_{6-14}$-aryl, —Z¹⁷-monovalent 3 to 12 membered aliphatic heterocyclic residue and —Z¹⁷-monovalent 5 to 14 membered aromatic heterocyclic residue,
wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^j$, wherein each $R^j$ is independently selected from the group consisting of halogen, —CN and *=O, and
wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^k$, wherein each $R^k$ is independently selected from the group consisting of $C_{1-20}$-alkyl, $C_{1-20}$-alkoxy, $C_{1-20}$-haloalkyl,
wherein
Z¹⁷ at each occurrence is independently $C_{1-6}$-alkylene, $C_{1-6}$-haloalkylene or a covalent bond.

6. The oligomer or polymer of formula (1) of claim 1, wherein G¹ and G² are the same or different and are a monocyclic bivalent 5 to 8 membered aromatic heterocyclic residue which monocyclic bivalent 5 to 8 membered aromatic heterocyclic residue is

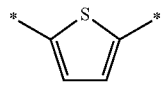 [SMILES: *c1ccc(*)s1]

which monocyclic bivalent 5 to 8 membered aromatic heterocyclic residue is substituted with 1 to 2 substituents $R^i$, wherein each $R^i$ is independently selected from the group consisting of $C_{1-30}$-alkyl and —Z¹⁷—$C_{6-14}$-aryl,
wherein $C_{1-30}$-alkyl and $C_{6-14}$-aryl are optionally substituted with 1 to 4 substituents $R^j$, wherein each $R^j$ is independently selected from the group consisting of halogen, —CN and *=O, and
wherein $C_{6-14}$-aryl is optionally substituted with 1 to 4 substituents $R^k$, wherein each $R^k$ is independently selected from the group consisting of $C_{1-20}$-alkyl and $C_{1-20}$-alkoxy,
wherein
Z¹⁷ at each occurrence is a covalent bond.

7. The oligomer or polymer of formula (1) of claim 1, wherein each $R^i$ is independently $C_{1-30}$-alkyl.

8. The oligomer or polymer of formula (1) of claim 1, wherein
L is a bivalent 5 to 18 membered aromatic heterocyclic residue, wherein the bivalent 5 to 18 membered aromatic heterocyclic residue is optionally substituted with 1 to 4 substituents $R^l$, wherein each $R^l$ is independently selected from the group consisting of $C_{1-30}$-alkyl, —Z¹⁸—O—$C_{1-30}$-alkyl, —Z¹⁸—S—$C_{1-30}$-alkyl, —Z¹⁸—$C_{3-10}$-cycloalkyl, —Z¹⁸—$C_{6-14}$-aryl, —Z¹⁸-monovalent 3 to 12 membered aliphatic heterocyclic residue and —Z¹⁸-monovalent 5 to 14 membered aromatic heterocyclic residue,
wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^m$, wherein each $R^m$ is independently selected from the group consisting of halogen, —CN and *=O, and
wherein $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R^n$, wherein each $R^n$ is independently selected from the group consisting of $C_{1-20}$-alkyl, $C_{1-20}$-alkoxy, $C_{1-20}$-haloalkyl,
wherein
Z¹⁸ at each occurrence is independently $C_{1-6}$-alkylene, $C_{1-6}$-haloalkylene or a covalent bond,
or
L is

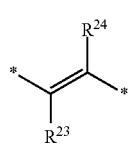

wherein $R^{23}$ and $R^{24}$ are the same or different and are H, halogen, —CN, $C_{1-30}$-alkyl, $C_{2-30}$-alkenyl, $C_{1-30}$-haloalkyl, —$X^7$—$R^{25}$, —$X^8$—$Ar^{13}$, —$X^8$—$Ar^{14}$—$Ar^{13}$, —$X^8$—$Ar^{14}$—$R^{26}$ or —$X^8$—$Ar^{14}$—$Ar^{15}$—$R^{26}$, wherein $X^7$ at each occurrence is independently —O—, —[$Z^{19}$—O]$_c$—, —[O—$Z^{19}$]$_c$—O—, —S—, —[$Z^{19}$—S—]$_c$— or —[S—$Z^{19}$]$_c$—S—, wherein $Z^{19}$ at each occurrence is independently $C_{1-6}$-alkylene, $C_{2-6}$-alkenylene or $C_{1-6}$-haloalkylene, c at each occurrence is independently an integer from 1 to 10 and $R^{25}$ at each occurrence is independently $C_{1-30}$-alkyl, $C_{2-30}$-alkenyl or $C_{1-30}$-haloalkyl, $X^8$ at each occurrence is independently —$Z^{21}$—O—$Z^{22}$—, —$Z^{21}$—S—$Z^{22}$—, $C_{1-30}$alkylene, $C_{2-30}$-alkenylene, $C_{1-30}$-haloalkylene or a covalent bond, wherein $Z^{21}$ and $Z^{22}$ at each occurrence are independently $C_{1-6}$-alkylene, $C_{2-6}$-alkenylene, $C_{1-6}$-haloalkylene or a covalent bond, and $Ar^{13}$ at each occurrence is independently $C_{6-14}$-aryl or monovalent 5 to 14 membered aromatic hetrocyclic residue, each optionally substituted with 1 to 5 substituents $R^o$, wherein each $R^o$ is independently selected from the group consisting of halogen, CN, $C_{1-6}$-alkyl, $C_{1-6}$-alkoxy and $C_{1-6}$-haloalkyl, $Ar^{14}$ and $Ar^{15}$ at each occurrence are independently $C_{6-14}$-arylene or bivalent 5 to 14 membered aromatic heterocyclic residue, each optionally substituted with 1 to 4 substituents $R^p$, wherein each $R^p$ is independently selected from the group consisting of halogen, CN, $C_{1-6}$-alkyl, $C_{1-6}$-alkoxy and $C_{1-6}$-haloalkyl, and $R^{26}$ at each occurrence is independently $C_{1-20}$-alkyl, $C_{2-20}$-alkenyl, $C_{1-20}$-haloalkyl or $C_{1-20}$-alkoxy.

9. The oligomer or polymer of formula (1) of claim 1, wherein

L is a bivalent 5 to 18 membered aromatic heterocyclic residue selected from the group consisting of

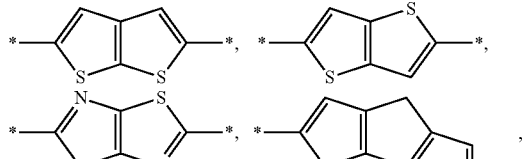

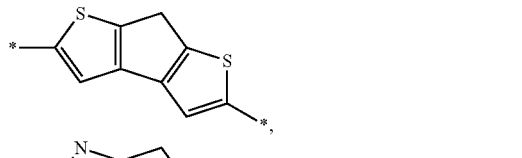

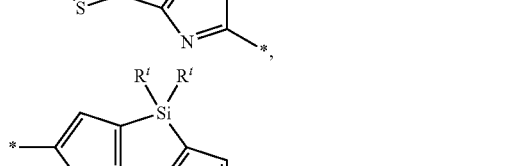

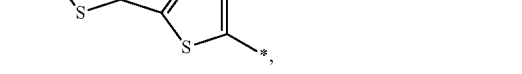

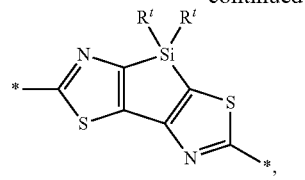

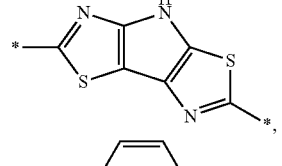

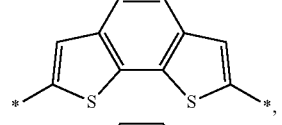

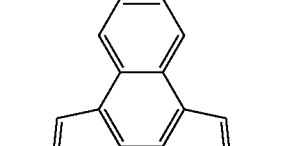

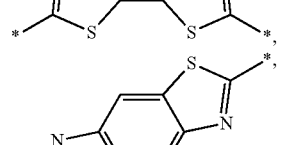

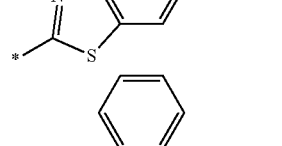

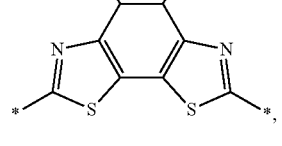

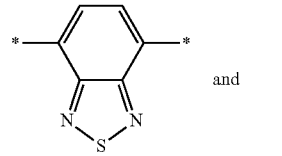 and 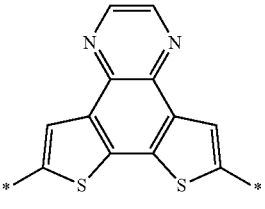

wherein the bivalent 5 to 18 membered aromatic heterocyclic residue is optionally substituted with 1 to 4 substituents $R^1$, wherein each $R^1$ is selected from the group consisting of a $C_{1-30}$-alkyl, a —$Z^{18}$—O—$C_{1-30}$-alkyl, a —$Z^{18}$—S—$C_{1-30}$-alkyl, a —$Z^{18}$—$C_{3-10}$-cycloalkyl, a —$Z^{18}$—$C_{6-14}$-aryl, a —$Z^{18}$-monovalent 3 to 12 membered aliphatic heterocyclic residue and a —$Z^{18}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R'''$, wherein $R'''$ is selected from the group consisting of a halogen, a —CN and a *=O, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents R", wherein R" is selected from the group consisting of a $C_{1-20}$-alkyl, a $C_{1-20}$-alkoxy, and a $C_{1-20}$-haloalkyl, and $Z^{18}$ is $C_{1-6}$-alkylene, $C_{1-6}$-haloalkylene or a covalent bond, and wherein $R^r$ is hydrogen or $C_{1-30}$-alkyl, or L is

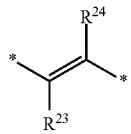

wherein $R^{23}$ and $R^{24}$ are independently H, halogen, —CN, $C_{1-30}$-alkyl, $C_{2-30}$-alkenyl, $C_{1-30}$-haloalkyl, —$X^7$—$R^{25}$, —$X^8$—$Ar^{13}$, —$X^8$—$Ar^{14}$—$Ar^{13}$, —$X^8$—$Ar^{14}$—$R^{26}$ or $X^8$—$Ar^{14}$—$Ar^{15}$—$R^{26}$, wherein $X^7$ is —O—, —$[Z^{19}$—O$]_c$—, —$[O$—$Z^{19}]_c$—O—, —S—, —$[Z^{19}$—S$]_c$— or —$[S$—$Z^{19}]_c$—S—, wherein $Z^{19}$ is $C_{1-6}$-alkylene, $C_{2-6}$-alkenylene or $C_{1-6}$-haloalkylene, and c is an integer of from 1 to 10, $R^{25}$ is $C_{1-30}$-alkyl, $C_{2-30}$-alkenyl or $C_{1-30}$-haloalkyl, $X^8$ is —$Z^{21}$—O—$Z^{22}$—, —$Z^{21}$—S—$Z^{22}$—, $C_{1-30}$-alkylene, $C_{2-30}$-alkenylene, $C_{1-30}$-haloalkylene or a covalent bond, wherein $Z^{21}$ and $Z^{22}$ are independently $C_{1-6}$-alkylene, $C_{2-6}$-alkenylene, $C_{1-6}$-haloalkylene or a covalent bond, $Ar^{13}$ is $C_{6-14}$-aryl or monovalent 5 to 14 membered aromatic hetrocyclic residue, each optionally substituted with 1 to 5 substituents $R^o$, wherein $R^o$ is selected from the group consisting of a halogen, a CN, a $C_{1-6}$-alkyl, a $C_{1-6}$-alkoxy and a $C_{1-6}$-haloalkyl, $Ar^{14}$ and $Ar^{15}$ are independently $C_{6-14}$-arylene or bivalent 5 to 14 membered aromatic heterocyclic residue, each optionally substituted with 1 to 4 substituents $R^p$, wherein $R^p$ is selected from the group consisting of a halogen, a CN, a $C_{1-6}$-alkyl, a $C_{1-6}$-alkoxy and a $C_{1-6}$-haloalkyl, and $R^{26}$ is $C_{1-20}$-alkyl, $C_{2-20}$-alkenyl, $C_{1-20}$-haloalkyl or $C_{1-20}$-alkoxy.

10. The oligomer or polymer of formula (1) of claim 1, wherein

L is

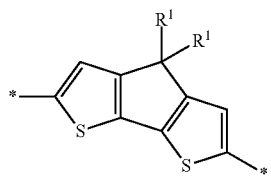

wherein each $R^1$ is selected from the group consisting of a $C_{1-30}$-alkyl, a —$Z^{18}$—O—$C_{1-30}$-alkyl, a —$Z^{18}$—S—$C_{1-30}$-alkyl, a —$Z^{18}$—$C_{3-10}$-cycloalkyl, a —$Z^{18}$—$C_{6-14}$-aryl, a —$Z^{18}$-monovalent 3 to 12 membered aliphatic heterocyclic residue and a —$Z^{18}$-monovalent 5 to 14 membered aromatic heterocyclic residue, wherein $C_{1-30}$-alkyl, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents $R'''$, wherein $R'''$ is selected from the group consisting of a halogen, a —CN and a *=O, $C_{3-10}$-cycloalkyl, $C_{6-14}$-aryl, monovalent 3 to 12 membered aliphatic heterocyclic residue and monovalent 5 to 14 membered aromatic heterocyclic residue is optionally substituted with 1 to 4 substituents R", wherein R" is selected from the group consisting of a $C_{1-20}$-alkyl, a $C_{1-20}$-alkoxy, and a $C_{1-20}$-haloalkyl, and $Z^{18}$ is $C_{1-6}$-alkylene, $C_{1-6}$-haloalkylene or a covalent bond, or L is

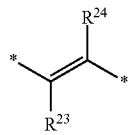

wherein $R^{23}$ and $R^{24}$ independently H, halogen, —CN, $C_{1-30}$-alkyl, $C_{2-30}$-alkenyl, $C_{1-30}$-haloalkyl, —$X^7$—$R^{25}$, —$X^8$—$Ar^{13}$, —$X^8$—$Ar^{14}$—$Ar^{13}$, —$X^8$—$Ar^{14}$—$R^{26}$ or —$X^8$—$Ar^{14}$—$Ar^{15}$—$R^{26}$, wherein $X^7$ is —O—, —$[Z^{19}$—O$]_c$—, —$[O$—$Z^{19}]_c$—, —S—, —$[Z^{19}$—S$]_c$— or —$[S$—$Z^{19}]_c$—S—, wherein $Z^{19}$ is $C_{1-6}$-alkylene, $C_{2-6}$-alkenylene or $C_{1-6}$-haloalkylene, and c is an integer of from 1 to 10, $R^{25}$ is $C_{1-30}$-alkyl, $C_{2-30}$-alkenyl or $C_{1-30}$-haloalkyl, $X^8$ is $Z^{21}$—O—$Z^{22}$—, —$Z^{21}$—S—$Z^{22}$—, $C_{1-30}$-alkylene, $C_{2-30}$-alkenylene, $C_{1-30}$-haloalkylene or a covalent bond, wherein $Z^{21}$ and $Z^{22}$ are independently $C_{1-6}$-alkylene, $C_{2-6}$-alkenylene, $C_{1-6}$-haloalkylene or a covalent bond, $Ar^{13}$ is $C_{6-14}$-aryl or monovalent 5 to 14 membered aromatic hetrocyclic residue, each optionally substituted with 1 to 5 substituents $R^o$, wherein $R^o$ is selected from the group consisting of a halogen, a CN, a $C_{1-6}$-alkyl, a $C_{1-6}$-alkoxy and a $C_{1-6}$-haloalkyl, $Ar^{14}$ and $Ar^{15}$ are independently $C_{6-14}$-arylene or bivalent 5 to 14 membered aromatic heterocyclic residue, each optionally substituted with 1 to 4 substituents $R^p$, wherein $R^p$ is selected from the group consisting of a halogen, a CN, a $C_{1-6}$-alkyl, a $C_{1-6}$-alkoxy and a $C_{1-6}$-haloalkyl, and $R^{26}$ is $C_{1-20}$-alkyl, $C_{2-20}$-alkenyl, $C_{1-20}$-haloalkyl or $C_{1-20}$-alkoxy.

11. The oligomer or polymer of formula (1) of claim 1, wherein q, r and s are 0 or 1, with the proviso that q, r and s are not all 0 at the same time.

12. The oligomer or polymer of formula (1) of claim 1, wherein n is an integer from 2 to 5000.

13. An electronic device comprising the oligomer or polymer of formula (1) of claim 1.

14. The electronic device of claim 13, wherein the electronic device is an organic field effect transistor.

15. The oligomer or polymer of formula (1) of claim 4, wherein $Ar^8$ is phenylene.

16. The oligomer or polymer of formula (1) of claim 1, wherein n is an integer from 2 to 1000.

17. The oligomer or polymer of formula (1) of claim 1, wherein n is an integer from 2 to 100.

18. The oligomer or polymer of formula (1) of claim 1, wherein n is an integer from 2 to 30.

19. The oligomer or polymer of formula (1) of claim 1, wherein $R^3$ is H, halogen, —CN, $C_{2-30}$-alkenyl, $C_{2-20}$-alkynyl, $C_{3-10}$-cycloalkyl, $C_{5-10}$-cycloalkenyl, $C_{8-10}$-cycloalkynyl, $C_{1-30}$-haloalkyl, monovalent 3 to 12 membered aliphatic heterocyclic residue, $-X^4-R^{12}$, $-X^5-Ar^7$, $-X^5-Ar^8-Ar^7$, $-X^5-Ar^8-R^{13}$ or $-X^5-Ar^8-Ar^9-R^{13}$.

20. The oligomer or polymer of formula (1) of claim 1, wherein each $R^i$ is independently n-octyl, n-(2-ethyl)hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$).

21. The oligomer or polymer of formula (1) of claim 1, wherein each $R^i$ is n-dodecyl.

\* \* \* \* \*